(12) United States Patent
Taylor et al.

(10) Patent No.: US 7,919,459 B2
(45) Date of Patent: Apr. 5, 2011

(54) USE OF C5A RECEPTOR ANTAGONIST IN THE TREATMENT OF FIBROSIS

(75) Inventors: Stephen Maxwell Taylor, Bellbird Park (AU); Ian Alexander Shiels, Muirlea (AU); Lindsay Charles Brown, Sinnamon Park (AU); Michael Wellesley Whitehouse, Holland Park (AU)

(73) Assignee: Promics Pty Limited, Macquarie Park, New South Wales (AU)

( * ) Notice: Subject to any disclaimer, the term of this patent is extended or adjusted under 35 U.S.C. 154(b) by 433 days.

(21) Appl. No.: 11/807,651

(22) Filed: May 30, 2007

(65) Prior Publication Data

US 2008/0058252 A1     Mar. 6, 2008

Related U.S. Application Data

(63) Continuation of application No. 10/510,614, filed as application No. PCT/AU03/00415 on Apr. 7, 2003, now abandoned.

(30) Foreign Application Priority Data

Apr. 8, 2002 (AU) .................................... PS 1606

(51) Int. Cl.
    *A61K 38/04*     (2006.01)
    *A61K 38/08*     (2006.01)
(52) U.S. Cl. .............................................. 514/11; 514/9
(58) Field of Classification Search ........................ None
See application file for complete search history.

(56) References Cited

U.S. PATENT DOCUMENTS

| | | | |
|---|---|---|---|
| 4,692,511 A | 9/1987 | Hahn | |
| 5,643,872 A | 7/1997 | Ali et al. | |
| 5,677,426 A | 10/1997 | Fong et al. | |
| 5,767,079 A * | 6/1998 | Glaser et al. | 514/12 |
| 5,789,542 A | 8/1998 | McLaughlin et al. | |
| 5,807,824 A * | 9/1998 | van Oostrum et al. | 514/12 |
| 5,916,898 A * | 6/1999 | Edwards et al. | 514/292 |
| 5,935,796 A | 8/1999 | Fosang et al. | |
| 6,821,950 B1 * | 11/2004 | Fairlie et al. | 514/9 |
| 7,410,945 B2 | 8/2008 | Woodruff et al. | |
| 7,579,432 B2 | 8/2009 | Taylor et al. | |
| 2002/0015957 A1 * | 2/2002 | Hageman et al. | 435/6 |
| 2002/0106732 A1 * | 8/2002 | Miyazono et al. | 435/69.1 |
| 2002/0147302 A1 | 10/2002 | Abdel-Magid et al. | |
| 2005/0119167 A1 | 6/2005 | Abbenante et al. | |
| 2006/0135411 A1 | 6/2006 | Woodruff et al. | |
| 2006/0217530 A1 | 9/2006 | Maxwell et al. | |
| 2006/0234921 A1 | 10/2006 | Shiels | |
| 2007/0021329 A1 | 1/2007 | Shiels et al. | |
| 2007/0054841 A1 | 3/2007 | Shiels et al. | |
| 2007/0249526 A1 | 10/2007 | Abbenante et al. | |
| 2008/0058252 A1 | 3/2008 | Taylor et al. | |
| 2009/0004264 A1 | 1/2009 | Woodruff et al. | |

FOREIGN PATENT DOCUMENTS

| | | |
|---|---|---|
| AU | 199880926 B2 | 6/1997 |
| EP | 1 308 438 A1 | 5/2003 |
| WO | 98/45309 | 10/1998 |
| WO | 98/54180 | 12/1998 |
| WO | 99/00406 | 1/1999 |
| WO | 99/02501 | 1/1999 |
| WO | WO 99/00406 A1 * | 1/1999 |
| WO | 02/14265 A1 | 2/2002 |
| WO | 02/24222 A2 | 3/2002 |
| WO | 03/033528 A1 | 4/2003 |
| WO | 03/086448 A | 10/2003 |
| WO | 2004/035080 A1 | 4/2004 |

OTHER PUBLICATIONS

Anaya et al., "Pulmonary Involvement in Rheumatoid Arthritis," Semin. Arthritis Rheum., 24(4): 242-254, Feb. 1995.
Arumugam et al.,"A Small Molecule C5a Receptor Antagonist Protects Kidneys from Ischemia/Reperfusion Injury in Rats," Kidney International, 63:134-42, Jan. 2003.
Arumugam et al.,"Protective Effect of a New C5a Receptor Antagonist against Ischemia-Reperfusion Injury in the Rat Small Intestine," J. Surg. Res.,103:260-7, Apr. 2002.
Baskaran et al., "Dynamics of Tissue Neutrophil Sequestration After Cutaneous Burns in Rats," J. Surg. Res., 93 (1):88-96, Sep. 2000.
Beames et al., "Studies on Intramolecular Alkylation. IV* The Preparation of Spirodienones from Phenolic Diazoketones" Aus. J. Chem., 27(6):1257-68, Jun. 1974.
Benoition et al., "Studies on Sensitivity to Racemization of Activated Residues in Couplings of N-benzyloxycarbonyldipeptides," Int. J. Pep. Prot. Res., 40(6):559-66, Dec. 1992.
Bernadelli et al., "Section VII. Trends and Perspectives," Ann. Rep. Med. Chem., 37:257-277, Oct. 2002.
Bertrand et al.,"CCR3 Blockade as a New Therapy for Asthma," Exp. Opin. Invents. Drugs 9(1):43-52, Jan. 2000.
Bodansky et al., "Introductions of Amine Protecting Groups," The Practice of Peptide Synthesis; 2nd, rev. ed., Springer-Verlag: Berlin, New York, Jun. 1994.
Brady et al., "Large-Scale Synthesis of a Cyclic Hexapeptide Analogue of Somatostatin," J. Org. Chem., 52(5):764-769, Mar. 1987.
Cain et al., "Modulation of Ligand Selectivity by Mutation of the First Extracellular Loop of the Human C5a Receptor," Biochem. Pharmacol., 61(12):1571-9, Jun. 15, 2001.
Chan et al., "Basic Procedures" in Fmoc Solid Phase Peptide Synthesis: A Practical Approach; Oxford University Press, 2000.
Cheng, "Section VII. Trends and Perspectives," Annual Reports in Medicinal Chemistry, 31:337-355, Feb. 1995.

(Continued)

*Primary Examiner* — Jeffrey E Russel
(74) *Attorney, Agent, or Firm* — Haynes and Boone, LLP

(57) ABSTRACT

This invention relates to the use of an antagonist of a G protein-coupled receptor in the prevention and/or treatment of fibrosis, such as the treatment of fibrosis associated with myocardial infarction or diabetes or certain pulmonary conditions. In a preferred embodiment, the antagonist is a C5a receptor antagonist, more preferably a cyclic peptide antagonist of the C5a receptor. In particular, the invention provides a method of prevention, treatment or alleviation of a fibrotic condition, comprising the step of administering an effective amount of an antagonist of a G protein-coupled receptor to a subject in need of such treatment.

13 Claims, 16 Drawing Sheets

OTHER PUBLICATIONS

Dinarello, "Dissociation of Transcription from Translation of Human IL-1B: Induction of Steady State mRNA by Adherence or Recombinant C5a in the Absence of Translation," Soc. Exp. Biol. Med., 200:228-232, Jun. 1992.

Diop et al. "Pregabalin (CI-1008) Inhibits the Trinitrobenzene Sulfonic Acid-Induced Chronic Colonic Allodynia in the Rat," J. Pharmacol. Exp. Ther., http://jpet.aspetjournals.org, 302(3):1013-1022, Sep. 2002.

Fields et al, "Solid Phase Peptide Synthesis Utilizing 9-fluorenylmethoxycarbonyl Amino Acids," Int. J. Pept. Prot. Res., 35(3):161-214, Mar. 1990.

Fukunaga et al., "A Novel Diamino-Pyridine Derivative (IS-741) Attenuates Rat lieitis Induced by Trinitrobenzene Sulfonic Acid," J. Gastroenterology, Springer-Verlag; 38(5):451-9, May 2003.

Galatis, P., "Section VII. Trends and Perspectives," Annu. Rep. Med. Chem., 32:305-326, 1997.

Gao et al., "Recent Advances in Neurokinin Receptor Antagonists," Curr. Med. Chem., 6(5):375-388, May 1999.

Gaudilliere et al. "Section VII. Trends and Perspectives," Annu. Rep. Med. Chem., 36:293-318, 2001.

Gaudilliere et al., "Section VII. Trends and Perspectives," Annu. Rep. Med. Chem., 35:331-356, 2000.

Harkin et al., "Complement C5a Receptor Antagonist Attenuates Multiple Organ Injury in a Model of Ruptured Abdominal Aortic Aneurysm," J. Vasc. Surg., 39(1):196-206, Jan. 2004.

Haynes et al., "Inhibition of C5a-Induced Neutrophil Chemotaxis and Macrophage Cytokine Production in Vitro by a New C5a Receptor Antagonist," Biochem. Pharmacol., Australia, 60(5):729-33, Sep. 1, 2000.

Heller et al., "Selection of a C5a Receptor Antagonist from Phage Libraries Attenuating the Inflammatory Response in Immune Complex Disease and Ischemia-Reperfusion Injury," J. Immunol. 163(2):985-94, Jul. 15, 1999.

Ikeda et al., Simvastatin Attenuates Trinitrobenzene Sulfonic Acid-Induced Colitis, But Not Oxazalone-Induced Colitis, Dig. Dis. Sci., 53(7):1869-75, Jan. 2008.

Johnson et al.,"Heterotrimeric G Protein Signalling: Role in Asthma and Allergic Inflammation" J. Allergy Clin. Immunol., 109(4):592-602, Apr. 2002.

Makrides, "Therapeutic Inhibition of the Complement System," Pharmacol. Rev., 50(1):59-87, Mar. 1998.

Morikis et al., "Structural Aspects and Design of Low-Molecular-Mass Complement Inhibitors," Biochem. Soc. Trans., 30(Pt. 6):1026-36, Nov. 2002.

Morris et al.,"Hapten-Induced Model of Chronic Inflammation and Ulceration in the Rat Colon," Gastroenterology, 96(3):795-803, Mar. 1989.

Owen et al., "Chemokine Receptors in Airway Disease: Which Receptor to Target?," Pulmonary Pharmacology and Therapeutics, 14(3):193-202, Jun. 2001.

Packowski et al., "Pharmacological Characterization of Antagonists of the C5a Receptor," Brit. J. Pharmacol., 128(7):1461-66, Dec. 1999.

Piccolo et al., "Chemoctactic Mediator Requirements in Lung Injury Following Skin Burns in Rats," Exp. Molec. Pathol., 66(3):220-226, Aug. 1999.

Reid et al., "A Convergent Solution-Phase Syntheis of the Macrocycle Ac-Phe-[Orn-Pro-D-Cha_Trp-Arg], A Potent New Antiinflammatory Drug," J. Org Chem., 68(11):4464-4471, May 30, 2003.

Roschmann et al., "Pulmonary Fibrosis in Rheumatoid Arthritis: A Review of Clinical Features and Therapy," Semin. Arthritis Rheum., 16(3):174-185, Feb. 1987.

Schmid et al., "Requirement for C5a In Lung Vascular Injury Following Thermal Trauma to Rat Skin," Shock, 8(2):119-124, Mar. 31, 1997.

Schuda et al., "A Short and Efficient Synthesis of (3S, 4S)-4-[(tert-Butyloxycarbonyl)amino]-5-cyclohexyl-3-hydroxypentanoic Acid Ethyl Ester," J. Org. Chem., 53:873-875, Feb. 15, 1988.

Short et al., "Effects of New C5a Receptor Antagonist on C5a- and Endotoxin-Induced Neutropenia in the Rat," Br. J. Pharmacol, 126(3):551-4, Feb. 1999.

Smith, Organic Synthesis, "Linear vs. Convergent Synthesis," 997-999, (1994).

Steinauer et al., "Studies on Racemizatino Associated with the Use of Benzotriazol-1-yl-tris (dimethylamino) Phosphonium Hexafluorophosphate (BOP)," Int. J. Pept. Protein Res., 34(4):295-8, Oct. 1989.

Stewart, "Current Therapy for Acromegaly," Trends Endocrinol. Metab., 11(4):128-132, May-Jun. 2000.

Strachan et al., "Inhibition of Immune-Complex Mediated Dermal Inflammation in Rats Following Either Oral or Topical Administration of a Small Molecule C5a Receptor Antagonist," British J. Pharmacol.,134(8):1778-86, Dec. 2001.

Strieter et al., "Effects of Interferon-1 b on Biomarker Expression in Patients with Idiopathic Pulmonary Fibrosis," Am. J. Resp. Crit. Care, 170(2): 133-140, Mar. 24, 2004.

Szebeni et al., "Complement Activation During Hemorrhagic Shock and Resuscitation in Swine," Shock, 20(4):347-355, Oct. 20, 2003.

Taylor et al., "Regulators of the Anaphylatoxin C5a", Exp. Opin. Ther. Patents, 10(4):449-458, Apr. 2000.

Toulouse et al., "Role of Tachykinin NK2 receptors in Normal and Altered Rectal Sensitivity in Rats," Brit. J. Pharmacol.,129(1):193-199, Jan. 2000.

Van Assche, "Emerging Drugs to Treat Crohn's Disease," Exp. Opin. Emerg. Drugs, 12(1):49-59, Mar. 2007.

Wong et al., "Small Molecular Probes for G-Protein-Coupled C5a Receptors: Conformationally Constrained Antagonists Derived from the C Terminus of the Human Plasma Protein C5a," J. Med. Chem., Australia, 41(18):3417-25, Aug. 27,1998.

Woodruff et al., "Species Dependence for Binding of Small Molecule Agonist and Antagonists to the C5a Receptor on Polymorphonuclear Leukocytes," Inflammation, 25(3):171-7, Jun. 2001.

Mita et al., "Levels of Cysteinyl Leukotriene Receptor niRNA in Human Peripheral Leucocytes: Significantly Higher Expression of Cysteinyl Leukotriene Receptor 2mRNA in Eosinophils," Clin. Exp. Allergy, 31(11):1714-1723, Nov. 2001.

Piccolo et al., "Role of Chemomatic factors in Neutrophil Activation After Thermal Injury in Rats," Inflammation, 23(4):371-385, Aug. 1999.

Neumann et al., "Local Production of Complement Proteins in Rheumatoid Arthritis Synovium," Arth. & Rheumat., 46 (4):934-945, Apr. 2002.

Oxford Textbook of Medicine, 3rd Edition, vol. 3, Sections 18-33 and Index, Oxford University Press, New York, NY, 1996.

Younger et al., "Detrimental Effects of Complement Activation in Hemorrhagic Shock," J. Appl Physiol.; 90(2):441-6, Feb. 2001.

Zhang et al., "An Efficient Synthesis of Cyclic RGD Peptides as Antithrombotic Agents" in J. Org. Chem., 61(15):5180-5185, Jul. 26, 1996.

http://www. lung.ca/diseases/pulmonaryfibrosis.html, Sep. 7, 2004.

http://www.clinicaltrials.gov, "Lung Disease Associated with Rheumatoid Arthritis," Study Sponsored by National Heart, Lung and Blood Institute, Sep. 7, 2004.

http://www.avantimmune.com/technology, AVANT Immunotherapeutics, Inc. Complement Inhibitors, 2004.

http://www.medicinenet.com/pulmonaryfibrosis/article.html., Sep. 7, 2004.

PCT/AU02/01427 International Search Report dated Dec. 20, 2002.

EP 02771873 European Search Report dated Nov. 9, 2005.

PCT/AU03/00415 International Search Report dated Jun. 19, 2003.

International Preliminary Examination Report dated Aug. 24, 2004 issued in PCT/AU03/01373.

PCT/AU2003/001365 International Preliminary Examination Report dated Jan. 27, 2005.

PCT/AU2003/001365 International Search Report dated Jan. 13, 2004.

AU2003/269602 Examiner's Report dated Oct. 29, 2007.

PCT/AU2004/000642 International Search Report dated Jul. 9, 2004.

Drapeau et al., "Synthetic C5a Receptor Antagonists," Biochem. Pharmacol., 45(6):1289-1299, 1993.

Shirahase et al., "Endothelium-Dependent Contraction Induced by Substance P In Canine Cerebral Arteries: Involvement of NK1 Receptors and Thromboxane A2," Life Sciences, 64(3):211-219, 1999.

PCT/AU2003/001374 International Search Report dated Jan. 15, 2004.

U.S. Appl. No. 10/510,614, now abandoned., application received Oct. 7, 2004.

Fairlie, D.P., Abbenante, G. and March, D., Curr. Med. Chem., 2:672-705 (1995).

International preliminary Examination Report dated Nov. 25, 2003 issued in PCT/AU02/01427.

Response to Written Opinion dated May 26, 2003, in the matter of PCT/AU02/01427 in the name of the University of Queensland entitled, "Cyclic Peptides as G-Protein-Coupled Receptor Antagonists," filed Oct. 16, 2002.

Woodruff, Trent M. et al., "A Potent Human C5a Receptor Antagonist Protects Against Disease Pathology in a Rat Model of Inflammatory Bowel Disease," Journal of Immunology, Baltimore, MD 171(10):5514-5520 (Nov. 15, 2003).

Supplemental European Search Report dated Jun. 30, 2009 issued in corresponding European Application No. 03750165.7.

Tyndall, J.D. and Fairlie, D.P., "Macrocycles mimic the extended peptide conformation recognized by aspartic, serine, cysteine and metallo proteases," Curr. Med. Chem. 8(8):893-907 (Jul. 2001).

U.S. Appl. No. 11/774,433, now abandoned, application received Jul. 6, 2007.

Fairlie et al., "Towards protein surface mimetics," Curr. Med. Chem. 5(1):29-62 (Feb. 1998).

Gerard C. and Gerard N. P., "C5A anaphylatoxin and its seven transmembrane-segment receptor," Annu. Rev. Immunol. 12:775-808 (1994).

Konteatis et al., "Development of C5a receptor antagonists. Differential loss of functinal responses," J. Immunol. 153(9):4200-4205 (Nov. 1, 1994).

Sanderson et al., "Decapeptide agonists of human C5a: the relationship between conformation and neutrophil response," J. med. Chem. 38(18):3669-3675 (Sep. 1, 1995).

International Preliminary Examination Report dated Jul. 2, 2004 issued in PCT/AU03/00415.

Strachan et al., "A New Small Molecule C65a Receptor Antagonist Inhibits the Reverse-Passive Arthus Reaction and Endotoxic Shock in Rats," J. Immunol. 164:6560-6565 (2000).

Finch et al., "Low-Molecular-Weight Peptidic and Cyclic Antagonists of the Receptor for the complement Factor C5a," J. Med. Chem., 42:1965-1974 (1999).

Kivitz et al., "Randomized placebo-controlled trial comparing efficacy and safety of valdecoxib with naproxen in patients with osteoarthritis," J. Fam. Prac. 51:530-7 (2002).

* cited by examiner

USE OF C5A RECEPTOR ANTAGONIST IN THE TREATMENT OF FIBROSIS

The present application is a continuation of U.S. utility patent application Ser. No. 10/510,614, filed Oct. 7, 2004 (now abandoned), which was a U.S. nationalization of PCT International Patent Application Serial No. PCT/AU03/00415, filed Apr. 7, 2003, which claims priority to Australian Provisional Application No. PS1606, filed Apr. 8, 2002 (now abandoned), each of which is specifically incorporated herein by reference in its entirety without disclaimer.

FIELD OF THE INVENTION

This invention relates to the use of an antagonist of a G protein-coupled receptor in the prevention and/or treatment of fibrosis, such as the treatment of fibrosis associated with myocardial infarction, diabetes, or certain pulmonary conditions. In a preferred embodiment the antagonist is a C5a receptor antagonist, more preferably a cyclic peptide antagonist of the C5a receptor.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

G protein-coupled receptors are prevalent throughout the human body, comprising approximately 60% of known cellular receptor types. They mediate signal transduction across the cell membrane for a very wide range of endogenous ligands and consequently participate in a diverse array of physiological and pathophysiological processes, including, but not limited to, those associated with cardiovascular, central and peripheral nervous system reproductive, metabolic, digestive, immunoinflammatory, and growth disorders, as well as other cell regulatory and proliferative disorders. Agents which selectively modulate functions of G protein-coupled receptcs have the potential for therapeutic applications. These receptors are becoming increasingly recognised as important drug targets, due to their crucial roles in signal transduction (G protein-coupled receptors, IBC Biomedical Library Series, 1996)

One of the most intensively studied G protein-coupled receptors is the receptor for C5a. C5a is one of the most potent chemotactic agents known, recruiting neutrophils and macrophages to sites of injury, altering their morphology; inducing degranulation; increasing calcium mobilisation, vascular permeability (oedema) and neutrophil adhesiveness; contracting smooth muscle; stimulating the release of inflammatory mediators, including histamine, TNF-α, IL-1, IL-6, IL-8, prostaglandins, and leukotrienes, and of lysosomal enzymes; promoting the formation of oxygen radicals; and enhancing antibody production (Gerard and Gerard, 1994).

Overexpression or underregulation of C5a is implicated in the pathogenesis of immune system-mediated inflammatory conditions, such as rheumatoid arthritis, adult respiratory distress syndrome (ARDS), systemic lupus erythematosus, tissue graft rejection, ischaemic heart disease, reperfusion injury, septic shock, psoriasis, gingivitis, atherosclerosis, Alzheimer's disease, lung injury and extracorporeal post-dialysis syndrome, and in a variety of other conditions (Whaley 1987; Sim 1993).

Agents which limit the pro-inflammatory actions of C5a have potential for inhibiting chronic inflammation, and its accompanying pain and tissue damage. For these reasons, molecules which prevent C5a from binding to its receptors are useful for treating chronic inflammatory disorders driven by complement activation. Such compounds also provide valuable new insights into the mechanisms of complement-mediated immunity.

In our previous applications No. PCT/AU98/00490 and Australian provisional No. PR8334, the entire disclosures of which are incorporated herein by this reference, we described the three-dimensional structure of some analogues of the C-terminus of human C5a, and used this information to design novel compounds which bind to the human C5a receptor (C5aR), behaving as either agonists or antagonists of C5a. It had previously been thought that a putative antagonist might require both a C-terminal arginine and a C-terminal carboxylate for receptor binding and antagonist activity (Konteatis et al, 1994). In PCT/AU98/00490 we showed that in fact a terminal carboxylate group is not generally required either for high affinity binding to C5aR or for antagonist activity. Instead we found that a hitherto unrecognised structural feature, a turn conformation, was the key recognition feature for high affinity binding to the human C5a receptor on neutrophils. As described in our Australian provisional application No. PR8334, filed on 17th Oct. 2001, we used these findings to design constrained structural templates which enable hydrophobic groups to be assembled into a hydrophobic array for interaction with a C5a receptor. We have subsequently found that preferred compounds of this class are able to inhibit inflammatory bowel disease, osteoarthritis, and hypersensitivity states, and this is described in our Australian provisional applications No. 2002952084, filed on 16th Oct. 2002, No. 2002952086, filed on 16th Oct. 2002, and No. 2002952129, filed on 17th Oct. 2002 respectively. The entire disclosures of these specifications are incorporated herein by this reference.

Fibrosis, the ingrowth of fibroblasts and the production of extracellular matrix to form abnormal scarring, can result from many causes, including trauma, surgical interventions, infections and pathological conditions. Fibrosis is a sequel of conditions such as chronic inflammation, including inflammation arising from diabetes and hypertension, but can arise in the absence of inflammation. It can occur in a variety of tissues, including but not limited to the lung, kidney, liver and heart. Fibrosis contributes to the loss of function experienced in such conditions, through the formation of abnormal quantities of extracellular matrix which change the physical properties of the scarred tissue. Diabetes- or hypertension-induced fibrosis of the heart, for instance, produces stiffening of the ventricle walls which contributes to decreased cardiac output.

It is estimated that 45% percent of deaths in the USA are attributable to disorders exhibiting proliferative fibrosis. Although fibrosis is debilitating and may be life-threatening, and the number of individuals who may benefit from an effective antifibrotic therapy is large, currently there are no effective treatments available. Both acute and chronic diseases which induce inflammation in the lung can lead to an irreversible process characterized by pulmonary fibrosis (PF). Pulmonary fibrosis may also occur as a side-effect of treatment with chemotherapeutic agents such as bleomycin. Pulmonary fibrosis is a severe disease, which leads to functional impairment and death. Cardiac fibrosis is associated with chronic hypertension, and both cardiac and renal fibrosis are long-term sequelae of diabetes.

Fibrosis is a dynamic process, and is considered to be potentially reversible. The extracellular matrix laid down during fibrosis may be resorbed after the withdrawal of the fibrotic stimuli. In many cases, however, the presence of fibrosis is only identified after loss of function has already taken place, for instance where decreased cardiac output is a sign of otherwise undetected cardiac fibrosis. Consequently, while it is desirable in certain circumstances to be able to prevent fibrosis from occurring, it is also desirable to be able to reverse existing fibrosis once it is detected. However, current therapeutic options for the treatment of fibrotic conditions are limited and relatively ineffective (el-Nahas et al. 1997).

The effects of drug-induced ad hypertension-induced pulmonary and renal fibrosis in animal models can be prevented or partially reversed by compounds which act by suppressing inflammatory events and down-regulating lung pro-collagen I over-expression (Iyer et al., 1999a,b).

We have shown that the administration of pirfenidone or spironolactone can prevent and partially reverse cardiac fibrosis and the increase in cardiac stiffness which occurs in streptozotocin-induced diabetes in rats (Miric G, et al., 2001) It is thought that pirfenidone acts by inhibiting increased TGF-β mRNA expression, allowing an increase in expression of metalloproteases which degrade the collagen I laid down during fibrosis. The mode of action of spironolactone is at present unknown. Spironolactone is a steroid analogue which is primarily used as a diuretic; pirfenidone (5-methyl-1-phenyl-2-(1H)-pyridone), an investigational compound being investigated as an anti-fibrotic agent in a number of indications.

It would be highly desirable to identify other therapeutically or prophylactically active agents for use in the treatment or prevention of fibrosis.

The overexpression or underregulation of a G-protein-coupled receptor, the C5a receptor, has been implicated in immune-system mediated events such as inflammation. Agents which influence C5a receptor activity, such as C5a receptor antagonists, have the potential to mediate inflammatory events, and may provide a means of therapeutic or prophylactic intervention, but have not previously been suggested as potential agents in the treatment or prevention of fibrosis.

We have now surprisingly found that a cyclic peptide with C5a receptor antagonist has the ability to ameliorate cardiac fibrosis in an animal model of this condition.

SUMMARY OF THE INVENTION

According to a first aspect, the invention provides a method of prevention, treatment or alleviation of a fibrotic condition, comprising the step of administering an effective amount of an antagonist of a G protein-coupled receptor to a subject in need of such treatment.

The use of any compound having activity as an antagonist of a G protein-coupled receptor, and particularly as a C5a receptor antagonist, is contemplated, including but not limited to those disclosed in our earlier International patent applications No.PCT/AU98/00490 or No. PCT/AU02/01427 or in International patent applications No. PCT/US00/11187 by Neurogen Corporation and No. PCT/JP01/06902 by Welfide Corporation, or antibody antagonists such as those disclosed in PCT/US00/24219 or U.S. Pat. No. 6,355,245. The entire disclosures of all of these specifications are incorporated herein by this cross-reference.

More preferably the C5a receptor antagonist is a peptide or a peptidometic compound, and more preferably is a cyclic peptide or a cyclic peptidometic compound. Even more preferably the compound is a cyclic peptide or a cyclic peptidometic compound of PCT/AU98/00490 or PCT/AU02/01427.

Still more preferably the antagonist is a compound which
(a) is an antagonist of a G protein-coupled receptor,
(b) has substantially no agonist activity, and
(c) is a cyclic peptide or peptidomimetic compound of formula I

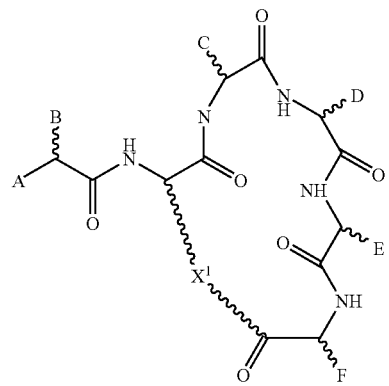

where A is H, alkyl, aryl, $NH_2$, NH-alkyl, $N(alkyl)_2$, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or the side chain of a D- or L-amino acid such as L-phenylalanine or L-phenylglycine, but is not the side chain of glycine, D-phenylalanine, L-homophenylalanine, L-tryptophan, L-homotryptophan, L-tyrosine, or L-homotyrosine;

C is a small substituent, such as the side chain of a D-, L- or homo-amino acid such as glycine, alanine, leucine, valine, proline, hydroxyproline, or thioproline, but is preferably not a bulky substituent such as isoleucine, phenylalanine, or cyclohexylalanine;

D is the side chain of a neutral D-amino acid such as D-Leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine, but is preferably not a small substituent such as the side chain of glycine or D-alanine, a bulky planar side chain such as D-tryptophan, or a bulky charged side chain such as D-arginine or D-Lysine;

E is a bulky substituent, such as the side chain of an amino acid selected from the group consisting of L-phenylalanine, L-tryptophan and L-homotryptophan, or is L-1-napthyl or L-3-benzothienyl alanine, but is not the side chain of D-tryptophan, L-N-methyltryptophan, L-homophenylalanine, L-2-naphthyl L-tetrahydroisoquinoline, L-cyclohexylalanine, D-leucine, L-fluorenylalanine, or L-histidine;

F is the side chain of L-arginine, L-homoarginine, L-citrulline, or L-canavanine, or a bioisostere thereof, ie. a side chain in which the terminal guanidine or urea group is retained, but the carbon backbone is replaced by a group which has different structure but is such that the side chain as a whole reacts with the target protein in the same way as the parent group; and X is —(CH$_2$)$_n$NH— or (CH$_2$)$_n$—S—, where n is an integer of from 1 to 4, preferably 2 or 3; —(CH$_2$)$_2$O—; —(CH$_2$)$_3$O—; —(CH$_2$)$_3$—; —(CH$_2$)$_4$—; —CH$_2$COCHRNH—; or —CH$_2$—CHCOCHRNH—, where R is the side chain of any common or uncommon amino acid.

In C, both the cis and trans forms of hydroxyproline and thioproline may be used.

Preferably A is an acetamide group, an aminomethyl group, or a substituted or unsubstituted sulphonamide group.

Preferably where A is a substituted sulphonamide, the substituent is an alkyl chain of 1 to 6, preferably 1 to 4 carbon atoms, or a phenyl or toluoyl group.

Preferably the antagonist is a C5a receptor antagonist. In a particularly preferred embodiment, the compound has antagonist activity against C5aR, and has no C5a agonist activity.

The compound is preferably an antagonist of C5a receptors on human and mammalian cells including, but not limited to, human polymorphonuclear leukocytes and human macrophages. The compound preferably binds potently and selectively to C5a receptors, and more preferably has potent antagonist activity at sub-micromolar concentrations. Even more preferably the compound has a receptor affinity IC50<25 μM, and an antagonist potency IC50<1 μM.

In particularly preferred embodiments the compound is selected from the group consisting of compounds I to 6, 10 to 15, 17, 19, 20, 22, 25, 26, 28, 30, 31, 33 to 37, 39 to 45, 56 to 58, and 60 to 64 described in PCT International patent application No. PCT/AU02/01427 (which gave rise to U.S. patent application Ser. No. 10/493,117, published Sep. 28, 2006 as 20060217530), including the following compounds:

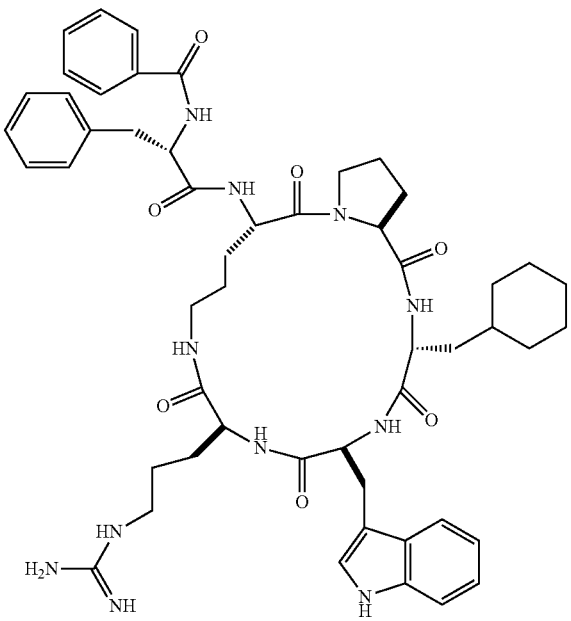

2

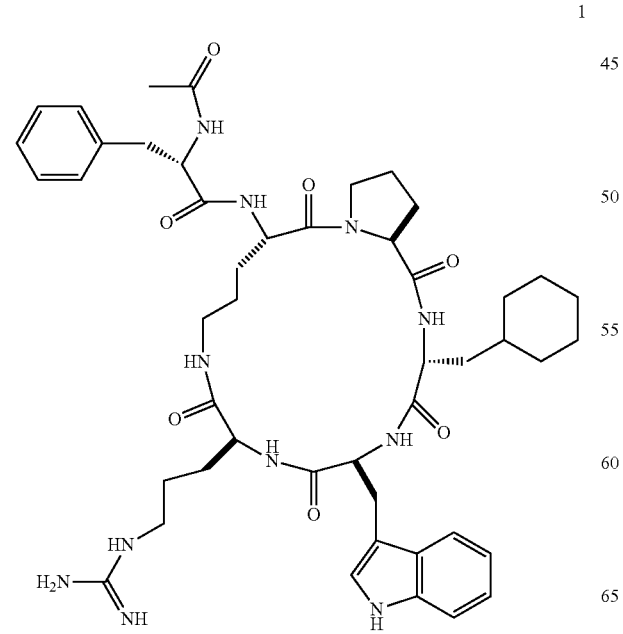

1

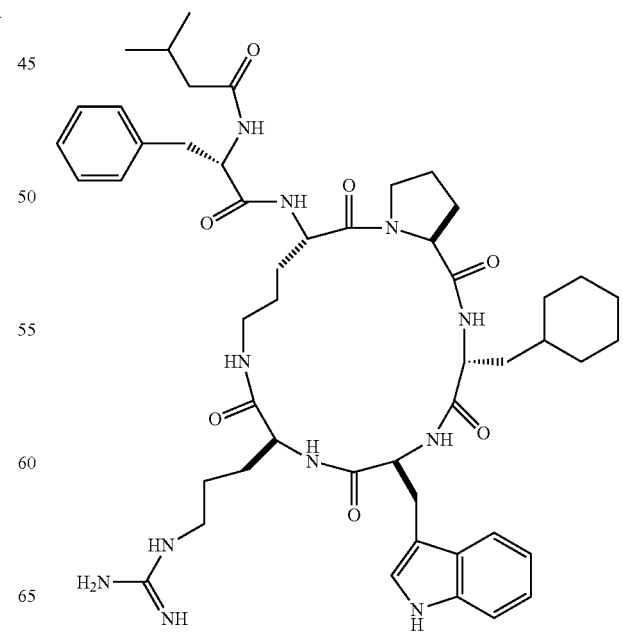

3

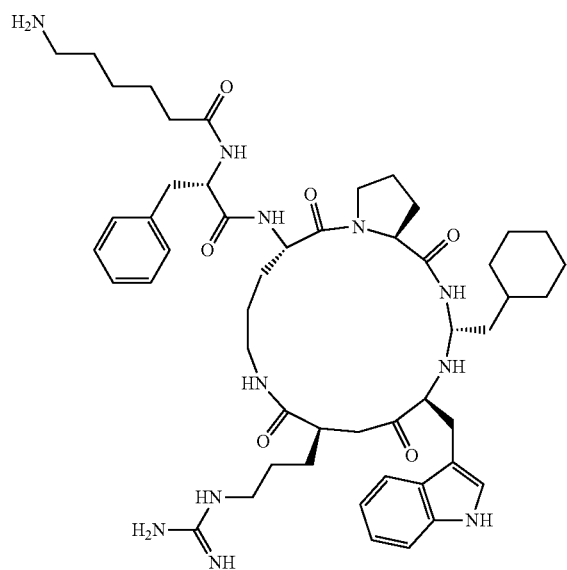
4
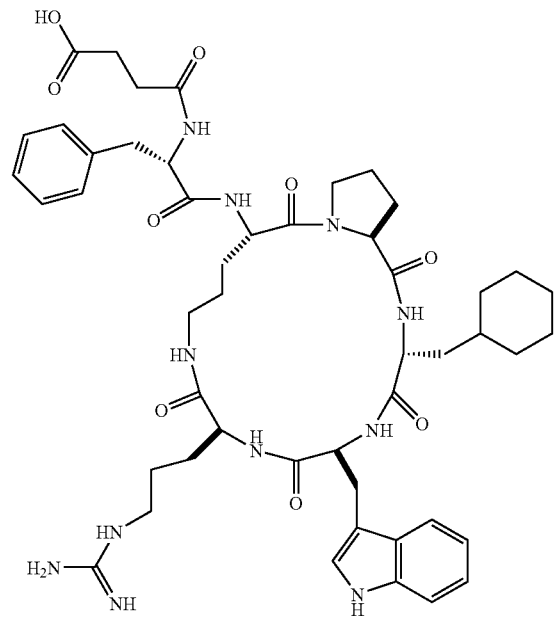
6
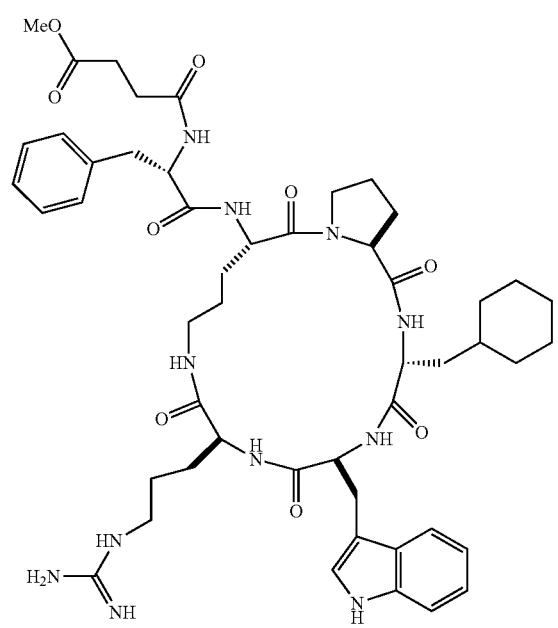
5
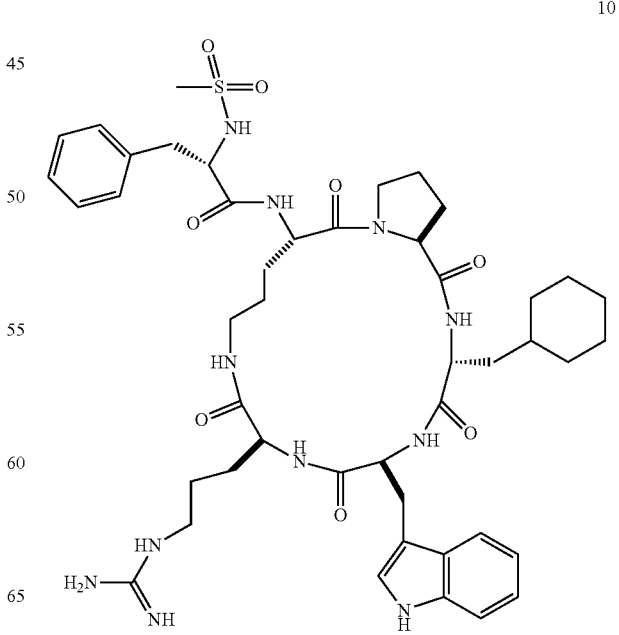
10

11
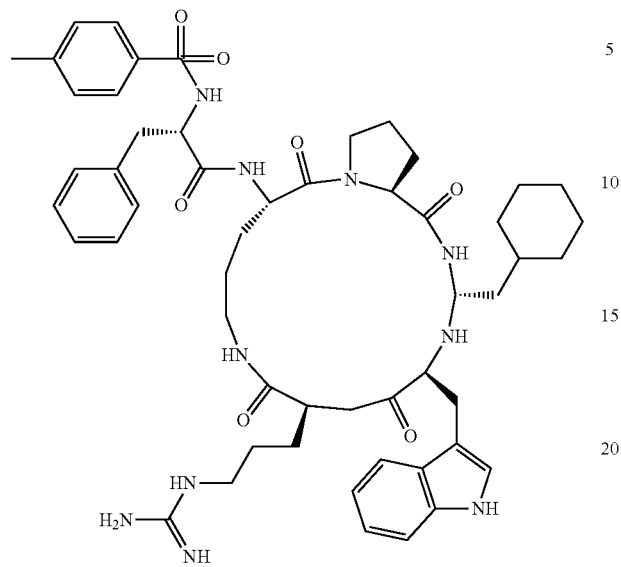
12
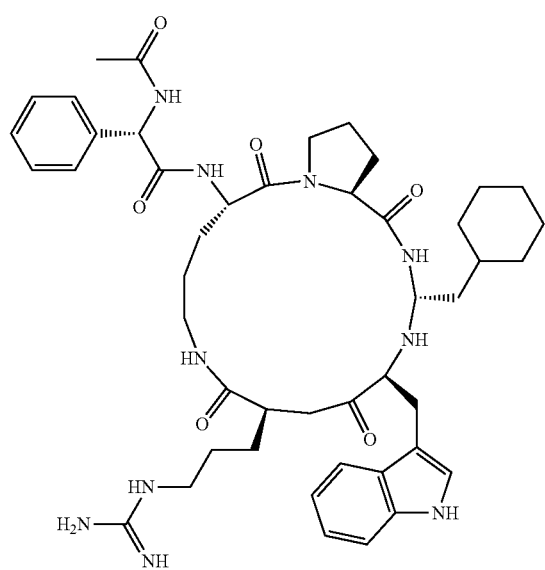
13
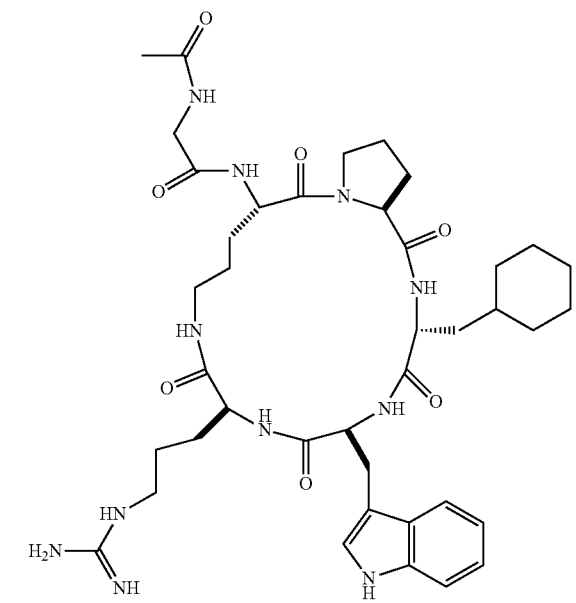
14
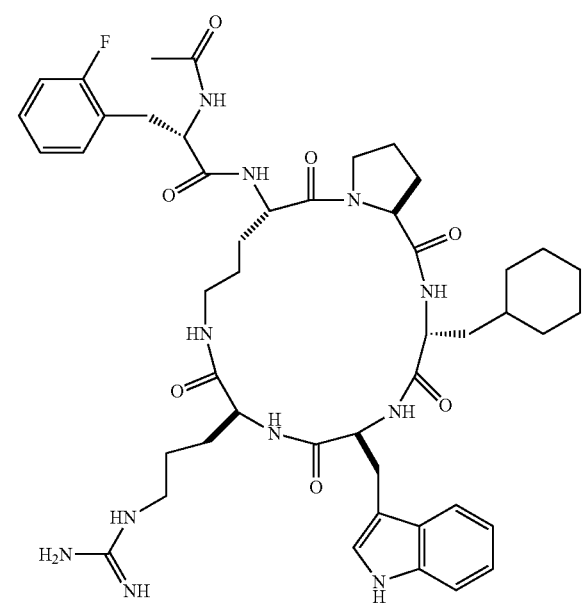

15
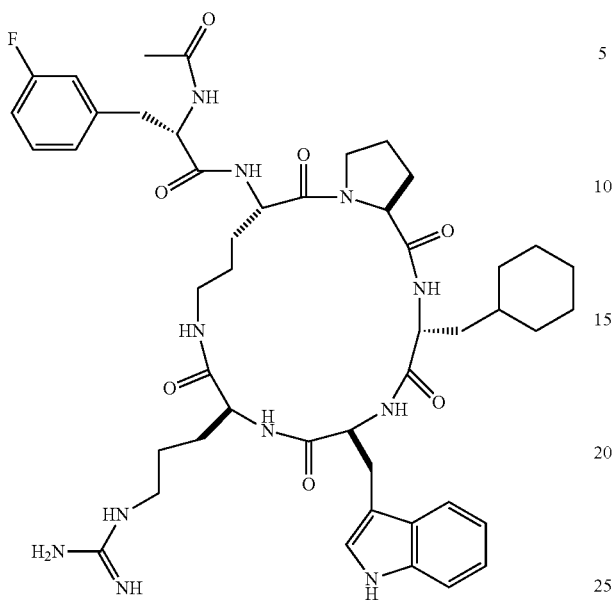
17
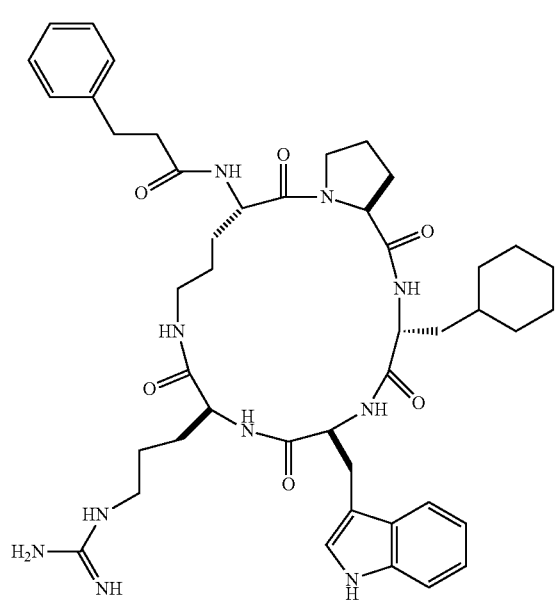
19
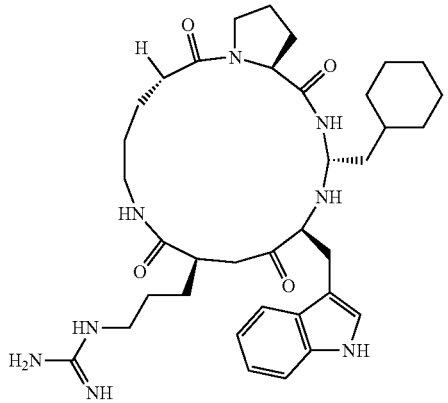
20
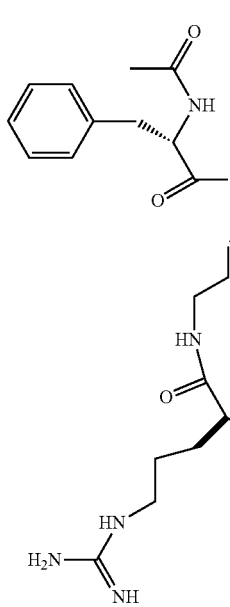
22
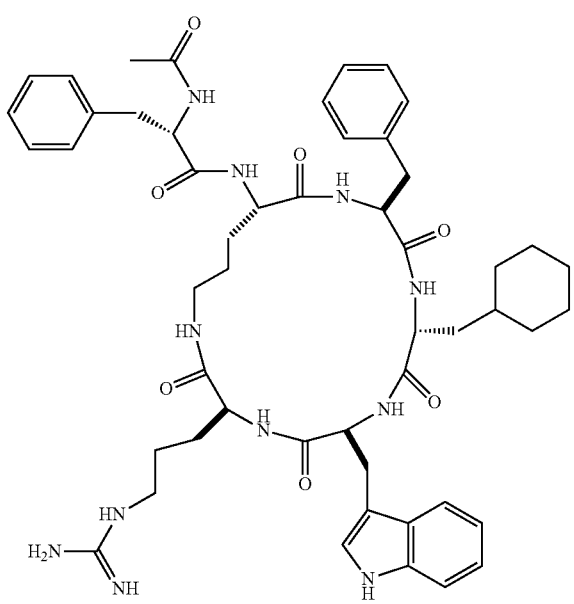

25
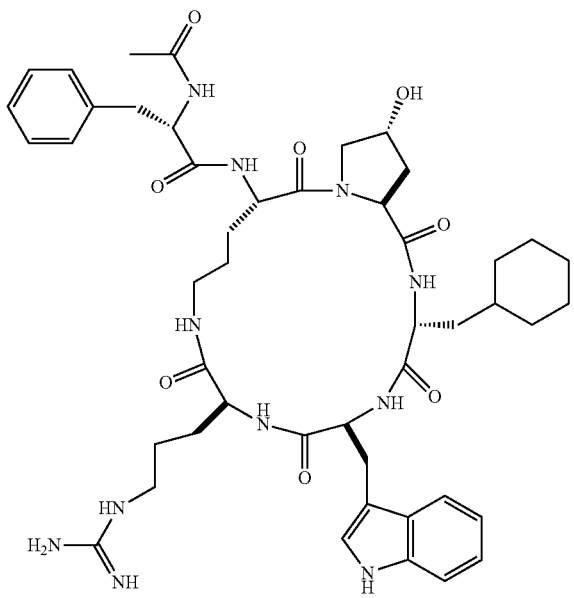
28
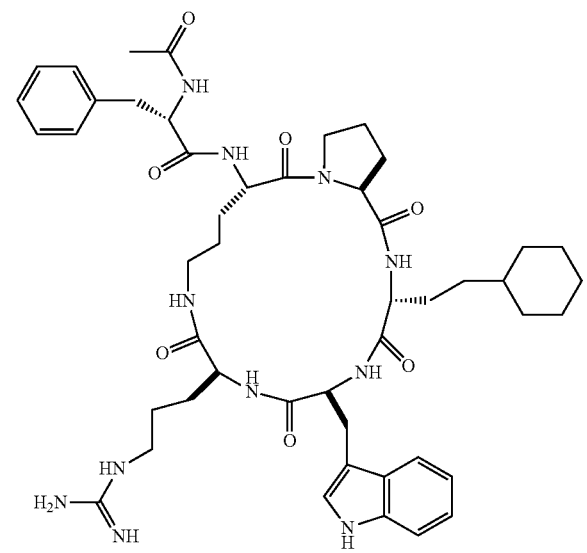
26
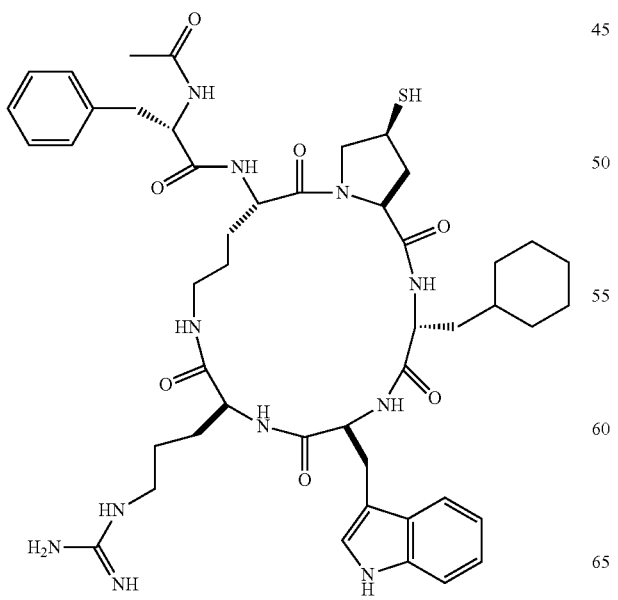
30
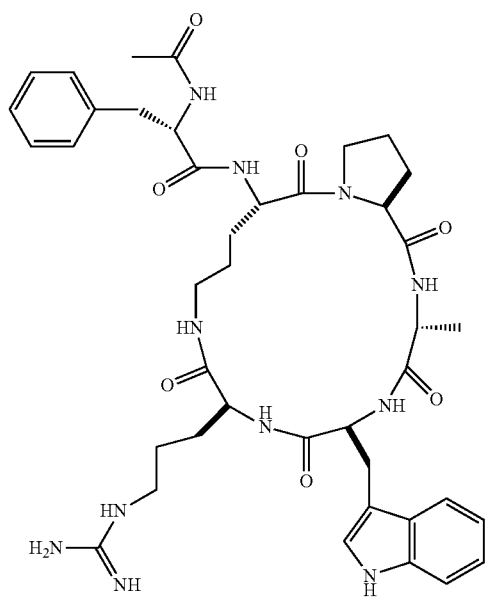

31
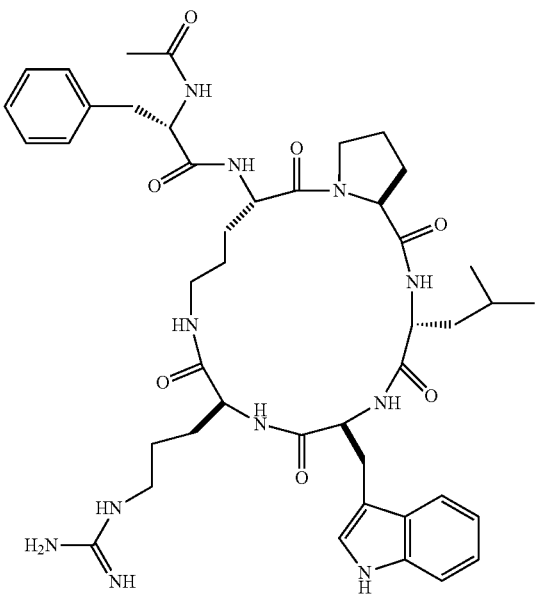
33
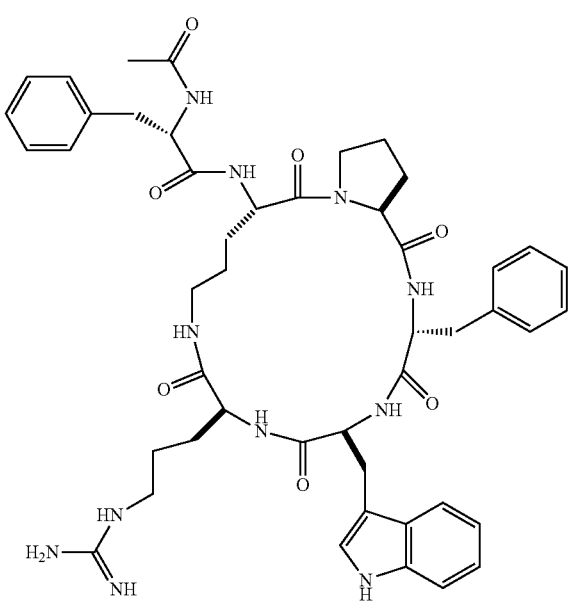
34
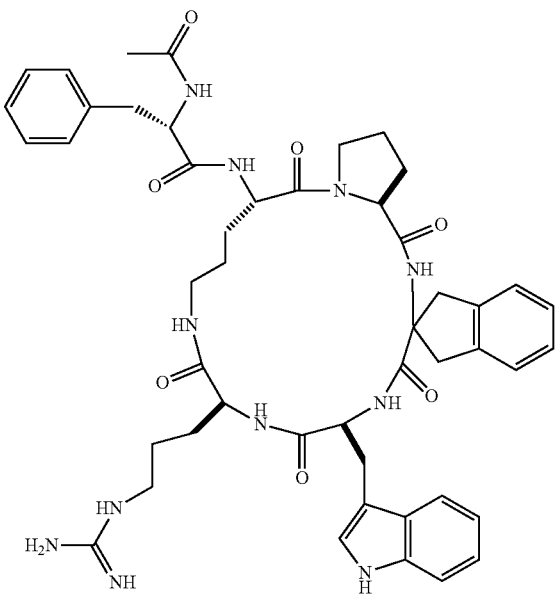
35
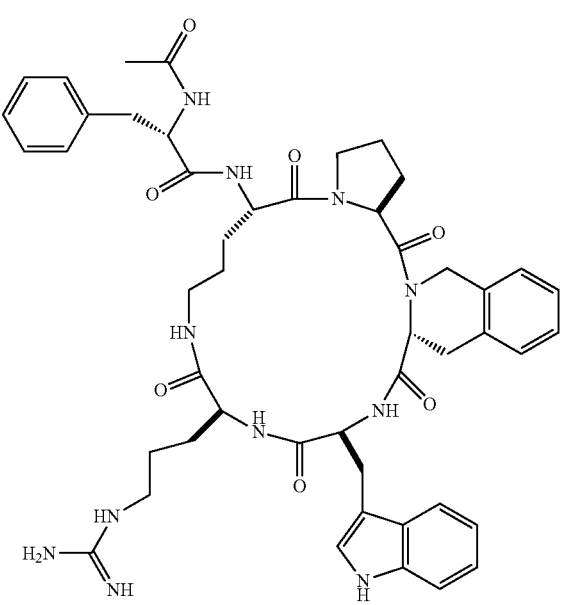

36
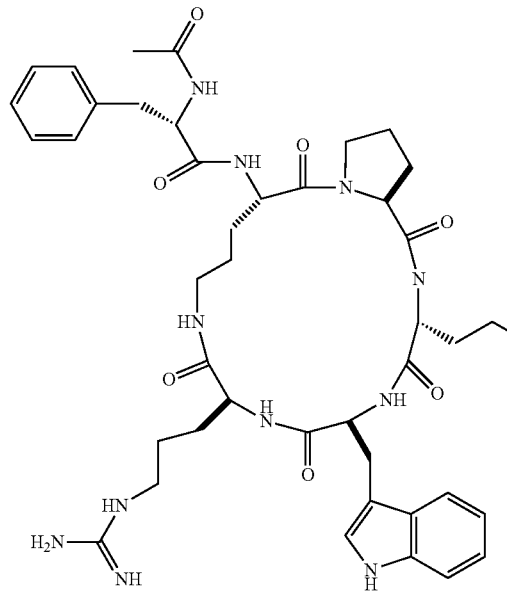
37
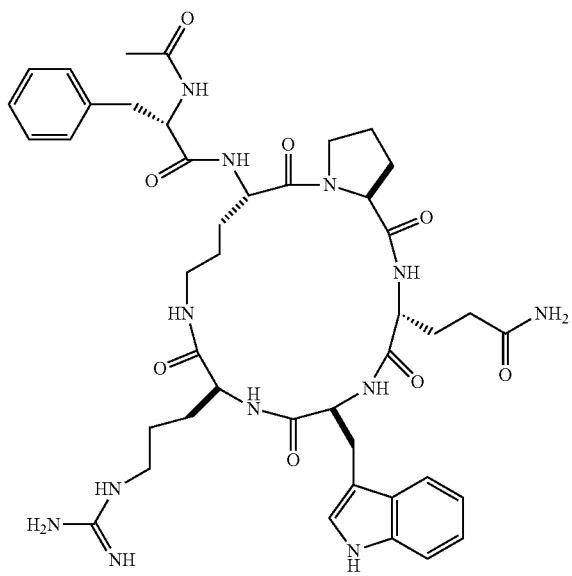
39
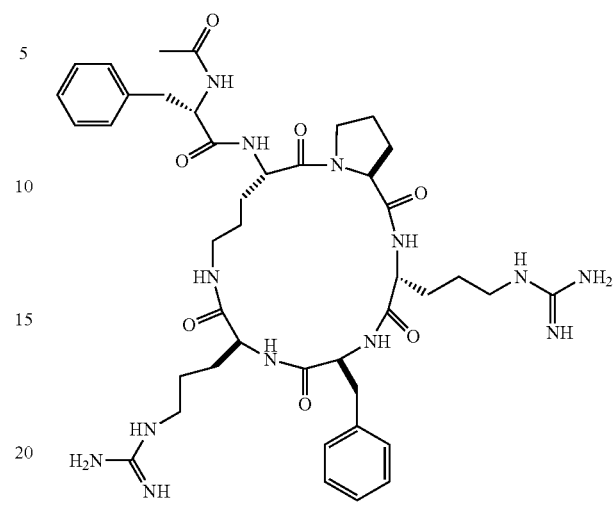
40
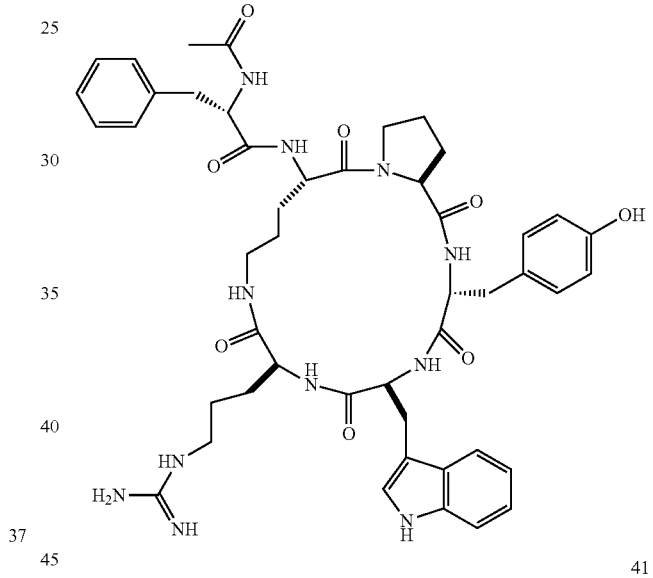
41
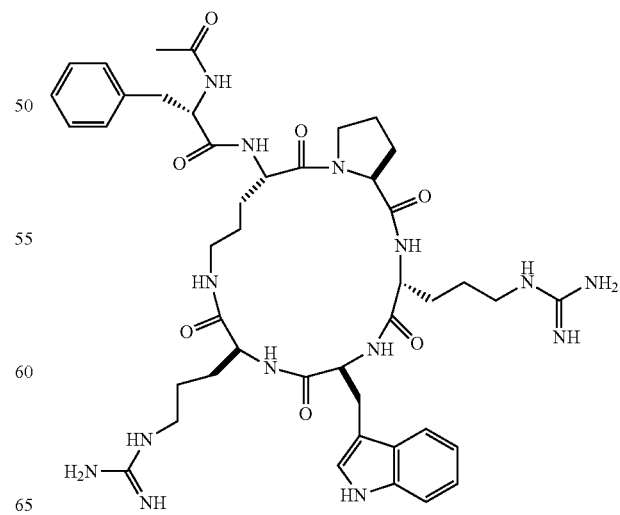

42
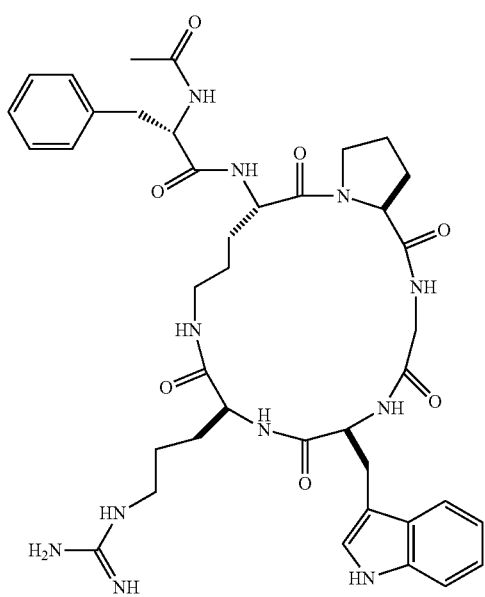
44
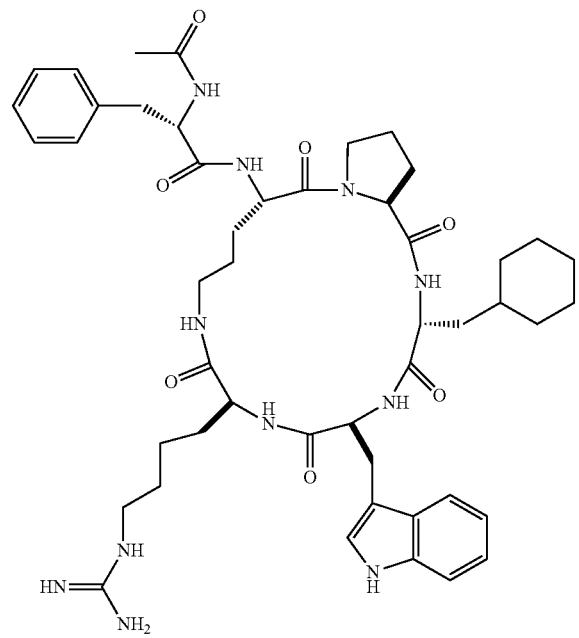
43
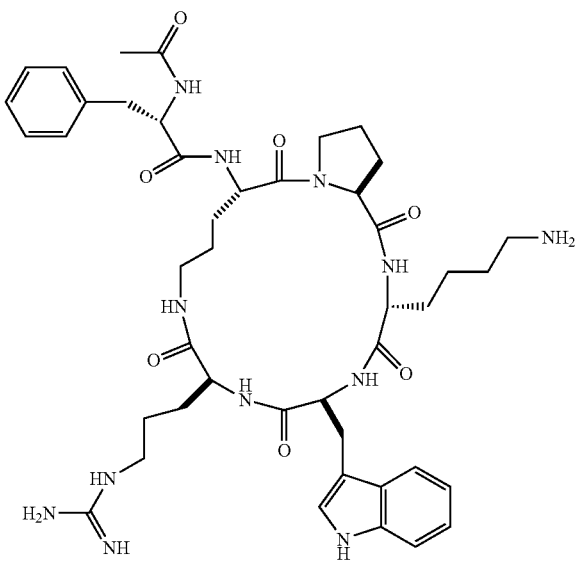
45
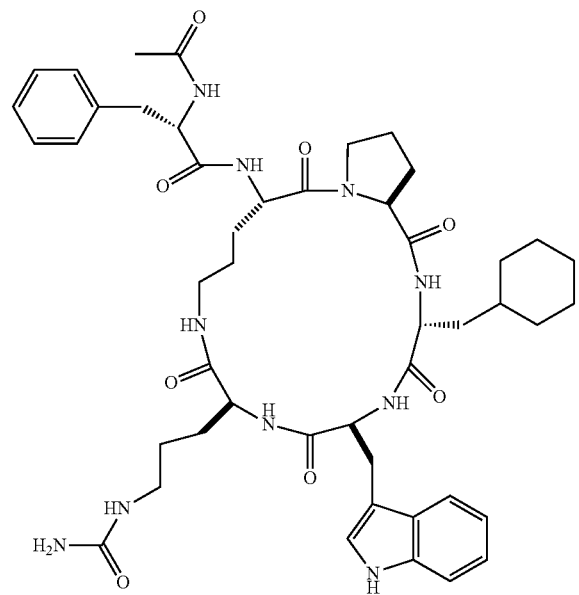

56
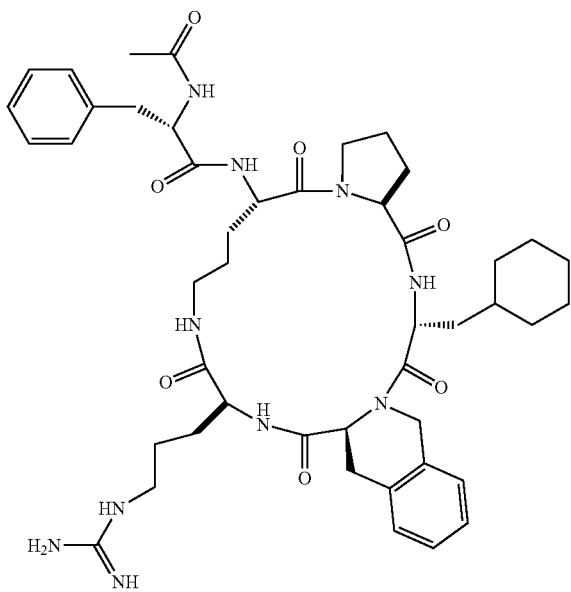
58
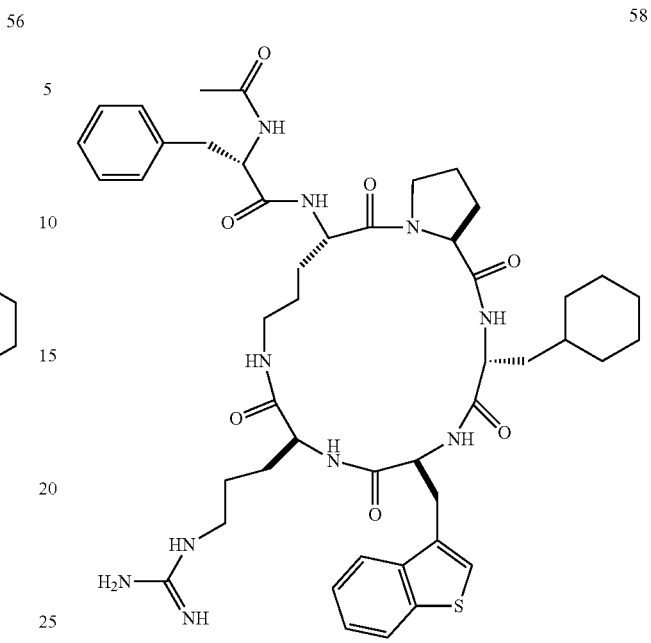
57
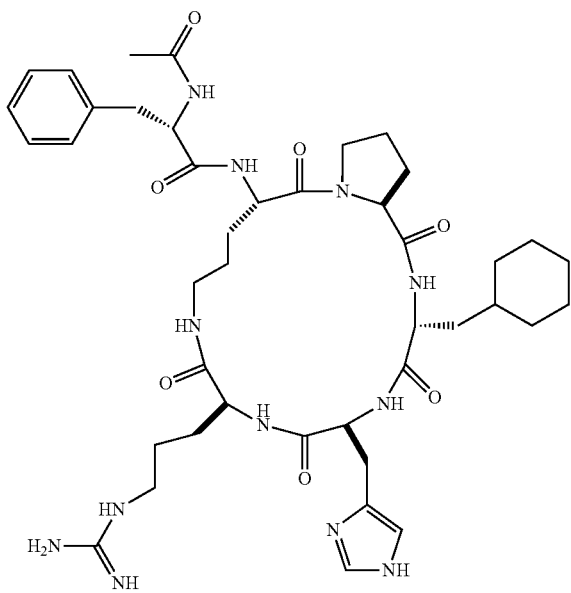
60
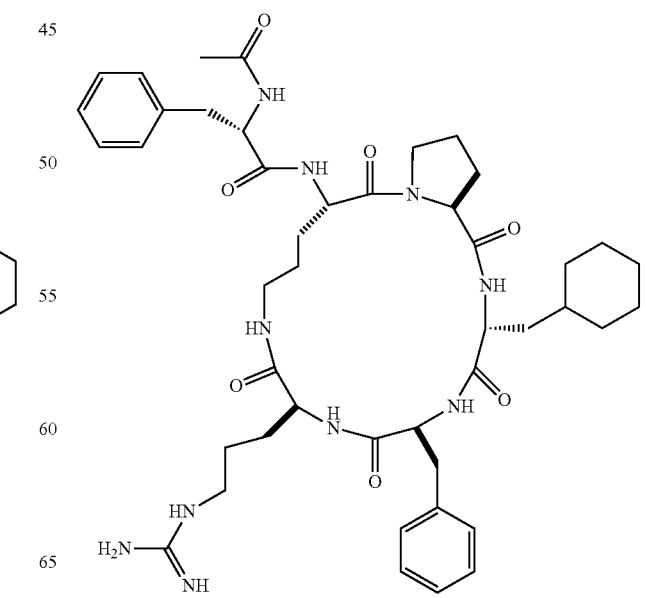

61
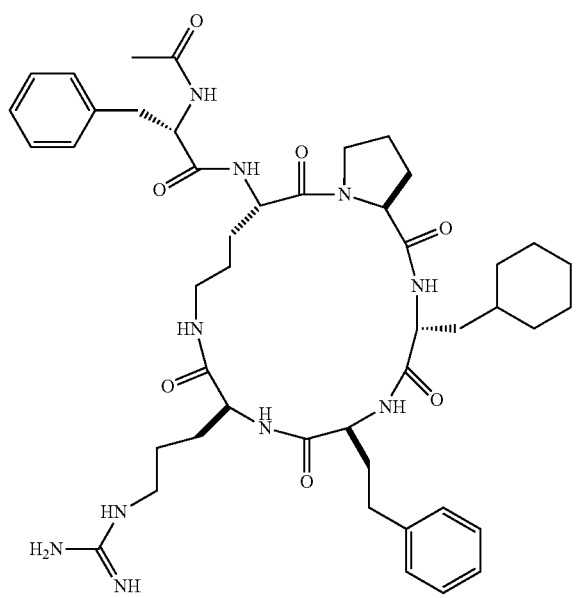
62
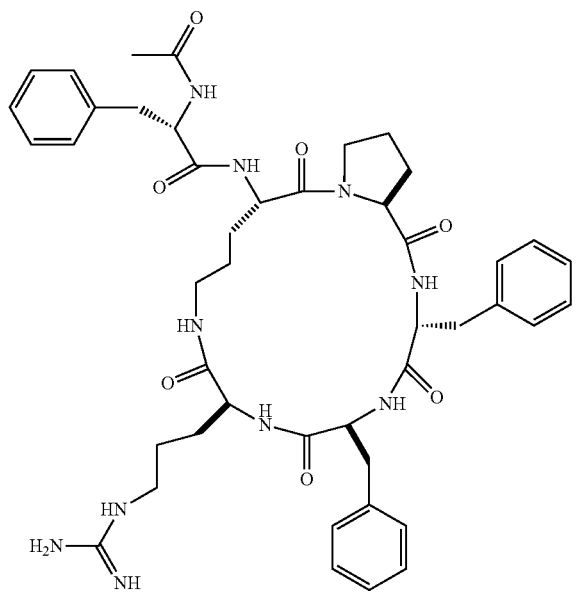
63
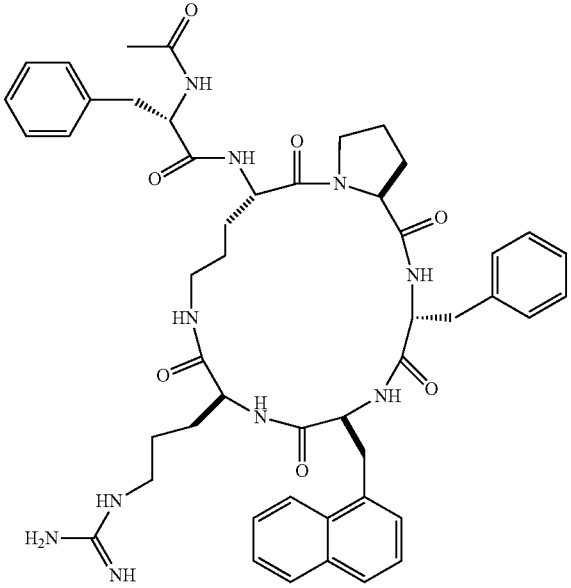
and
64
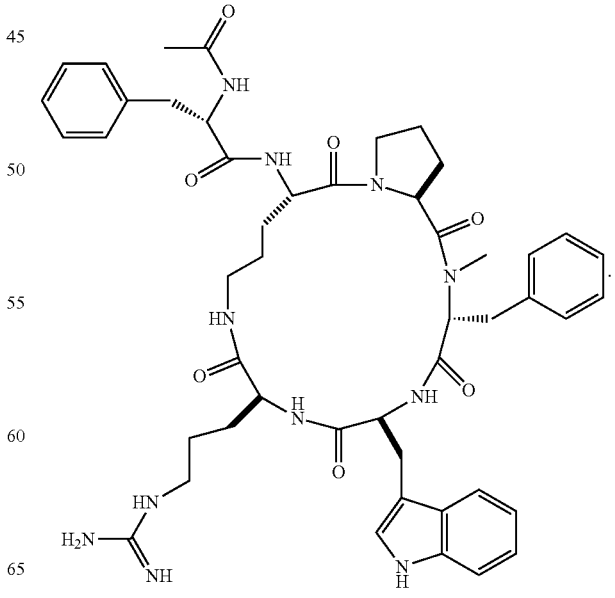

In a particularly preferred embodiment, the compound is PMX53 (compound 1), compound 33, compound 60 or compound 45 illustrated supra.

Most preferably the compound is the compound designated PMX53, disclosed in PCT/AU98/00490, which has the formula

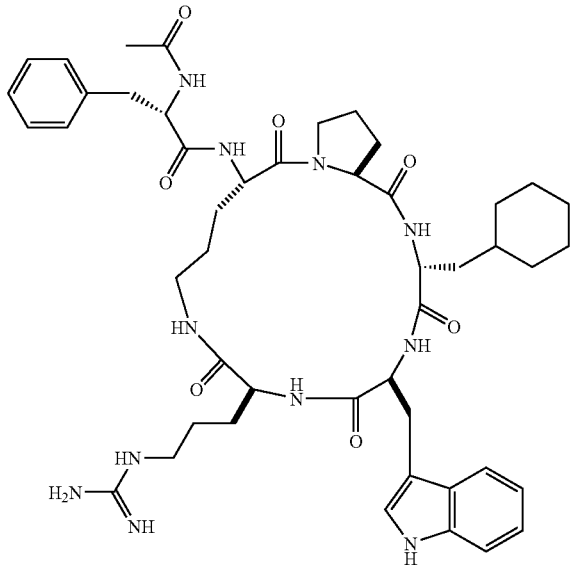

In a second aspect, the invention provides the use of a C5a receptor antagonist for the manufacture of a medicament for use in the treatment of a fibrotic condition.

For the purposes of this specification, the term "C5a receptor antagonist" includes any compound which can reduce or inhibit effects mediated by the interaction between C5a and C5R receptor. Thus the term includes polyclonal or monoclonal antibodies, peptides, peptidomimetics, and non-peptide compounds.

Methods and pharmaceutical carriers for preparation of suitable formulations for administration by any desired route may be prepared by standard methods, for example by reference to well-known textbooks such as Remington: The Science and Practice of Pharmacy, Vol. II, 1995 ($19^{th}$ edition), A. R. Gennaro (ed), Mack Publishing Company, Easton, Pa., or Australian Prescription Products Guide, Vol. 1, 1995 ($24^{th}$ edition) J. Thomas (ed), Australian Pharmaceutical Publishing Company Ltd, Victoria, Australia.

The compounds may be administered at any suitable dose and by any suitable route. Oral, transdermal or intranasal administration is preferred, because of the greater convenience and acceptability of these routes. The effective dose will depend on the nature of the condition to be treated, and the age, weight, and underlying state of health of the individual being treated. This will be at the discretion of the attending physician or veterinarian. Suitable dosage levels may readily be determined by trial and error experimentation, using methods which are well known in the art.

The carrier or diluent, and other excipients, will depend on the route of administration, and again the person skilled in the art will readily be able to determine the most suitable formulation for each particular case.

While it is particularly contemplated that the subject for treatment by the method of the invention is human, the treatment is also applicable to veterinary treatment, including treatment of companion animals such as dogs and cats, and domestic animals such as horses, cattle and sheep, or zoo animals such as felids, canids, bovids, and ungulates.

BRIEF DESCRIPTION OF THE FIGURES

(FIG. 5A) interstitial (FIG. 5B) perivascular

(FIG. 6A) left ventricle (FIG. 6B) right ventricle

(FIG. 7A) tubulointerstitial (FIG. 7B) glomerular

(FIG. 8A) left ventricle (FIG. 8B) right ventricle

(FIG. 9A) Left ventricular wall thickness in diastole.

(FIG. 9B) Left ventricular internal diameter in diastole.

(FIG. 9C) E/A flow ratio.

(FIG. 9D) Diastolic volume.

(FIG. 9E) Cardiac output.

FIG. 12A and FIG. 2B show haematoxylin and eosin-stained sections of rat lung at ×40 magnification.

(FIG. 12A) Normal lung.

(FIG. 17A) Alveolar macrophages (arrows) in the alveolar space.

(FIG. 17B) Increase in alveolar wall thickness, with some collagen deposition (arrow) in the alveolar septa.

FIG. 18A, FIG. 8B, and FIG. 18C show collagen as detected by Picro Sirius Red staining in rat lung (×40).

(FIG. 18A) Normal rat.

(FIG. 18C) Non-drug treated bleomycin instilled rat, showing typical fibrous foci in the alveolar space.

DETAILED DESCRIPTION OF THE INVENTION

Figure 1A:
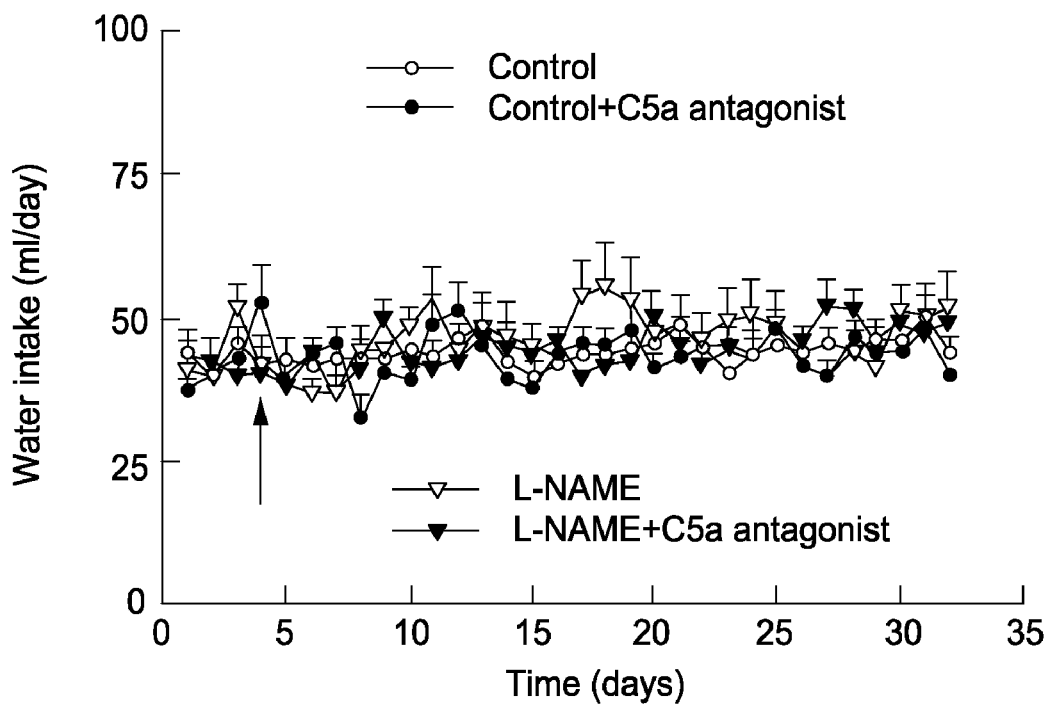
FIG. 1a shows a comparison of the daily water intake for control, control+C5a antagonist, L-NAME and L-NAME+C5a antagonist treated rats. Values are expressed as mean±SEM. The arrow indicates initiation of L-NAME treatment.

For the purposes of this specification, the term "fibrotic condition" is to be taken to mean any fibrotic disorder, such as multiple sclerosis, retinal disorders including proliferative vitroretinopathy and macular degeneration, scleroderma, sclerosing peritonitis, fibrosis arising from trauma, burns, chemotherapy, radiation, infection or surgery and fibrosis of major organs such as the kidney, liver, heart or lungs.

The term "C5a receptor antagonist" includes any compound which can reduce or inhibit effects mediated by the interaction between C5a and C5a receptor. Thus the term includes polyclonal or monoclonal antibodies, peptides, peptidomimetics, and non-peptide compounds.

The terms "treating," "treatment," and "therapy" as used herein refer to curative therapy, prophylactic therapy, and preventative therapy.

For the purposes of this specification it will be clearly understood that the word "comprising" means "including but not limited to", and that the word "comprises" has a corresponding meaning.

As used herein, the singular forms "a", "an", and "the" include plural reference unless the context clearly dictates otherwise. Thus, for example a reference to "an enzyme" includes a plurality of such enzymes, and a reference to "an amino acid" is a reference to one or more amino acids.

Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

For the purposes of this specification, the term "alkyl" is to be taken to mean a straight, branched, or cyclic, substituted or unsubstituted alkyl chain of 1 to 6, preferably 1 to 4 carbons. Most preferably the alkyl group is a methyl group. The term "acyl" is to be taken to mean a substituted or unsubstituted acyl of 1 to 6, preferably 1 to 4 carbon atoms. Most preferably the acyl group is acetyl. The term "aryl" is to be understood to mean a substituted or unsubstituted homocyclic or heterocyclic aryl group, in which the ring preferably has 5 or 6 members.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine.

An "uncommon" amino acid includes, but is not restricted to, D-amino acids, homo-amino acids, N-alkyl amino acids, dehydroamino acids, aromatic amino acids other than phenylalanine, tyrosine and tryptophan, ortho-, meta- or para-aminobenzoic acid, ornithine, citrulline, canavanine, norleucine, γ-glutamic acid, aminobutyric acid, L-fluorenylalanine, L-3-benzothienylalaine, and α,α-disubstituted amino acids.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease.

"Treating" as used herein covers any treatment of, or prevention of disease in a vertebrate, a mammal, particularly a human, and includes: preventing the disease from occurring in a subject who may be predisposed to the disease, but has not yet been diagnosed as having it; inhibiting the disease, i.e., arresting its development; or relieving or ameliorating the effects of the disease, i.e., cause regression of the effects of the disease.

The invention includes the use of various pharmaceutical compositions useful for ameliorating disease. The pharmaceutical compositions according to one embodiment of the invention are prepared by bringing a compound of formula I, analogue, derivatives or salts thereof and one or more pharmaceutically-active agents or combinations of compound of formula I and one or more pharmaceutically-active agents into a form suitable for administration to a subject using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g. in L anger, Science, 249 1527, (1990). Formulations for or al use may be in the form of hard gelatin capsules, in which the active ingredient is mixed with an inert solid diluent, for example, calcium carbonate, calcium phosphate or kaolin. They may also be in the form of soft gelatin capsules, in which the active ingredient is mixed with water or an oil medium, such as peanut oil, liquid paraffin or olive oil.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodiumchloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

Agents useful in the invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compounds of the present invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the invention may form solvates with water or common organic solvents. Such solvates are encompassed within the scope of the invention.

The compounds of the invention may additionally be combined with other therapeutic compounds to provide an operative combination. It is intended to include any chemically compatible combination of pharmaceutically-active agents, as long as the combination does not eliminate the activity of the compound of this invention. For example, spironolactone, pirfenidone, *Gingko biloba* extract (Welt et al, 1999), and tocopherol acetate (Rosen et al, 1995) are known in the art for treatment of fibrosis. Inhibitors of prolyl hydroxylase, procollagen C-proteinase, also known as bone morphogenetic protein-1 (BMP-1), or connective tissue growth factor 02450, WO00/are being investigated for this purpose by FibroGen, Inc. See for example WO/01/56996, WO/01/15729, WO00/02450, WO00/50390, WO00/27868, WO00/13706, and WO/9921860. These compounds include prostacyclin and phenanthroline derivatives. The invention includes within its scope combinations of C5a inhibitors and such known agents.

General Methods
Peptide Synthesis

Cyclic peptide compounds of formula I are prepared according to methods described in detail in our earlier applications No. PCT/AU98/00490 and No. PCT/AU02/01427, the entire disclosures of which are incorporated herein by this reference. While the invention is specifically illustrated with reference to the compound AcF-[OPdChaWR] (PMX53), whose corresponding linear peptide is Ac-Phe-Orn-Pro-dCha-Trp-Arg, it will be clearly understood that the invention is not limited to this compound.

Compounds 1-6, 17, 20, 28, 30, 31, 36 and 44, shown above (and also disclosed in International Patent Application No. PCT/AU98/00490) and compounds 10-12, 14, 15, 25, 33, 35, 40, 45, 58 and 60, also shown above and disclosed for the first time in PCT International Patent Application No. PCT/AU02/01427 have appreciable antagonist potency ($IC_{50} < 1$ µM) against the C5a receptor on human neutrophils. PMX53 and compounds 33, 45 and 60 illustrated infra (and also disclosed in International Patent Application No. PCT/AU02/01427) are most preferred:

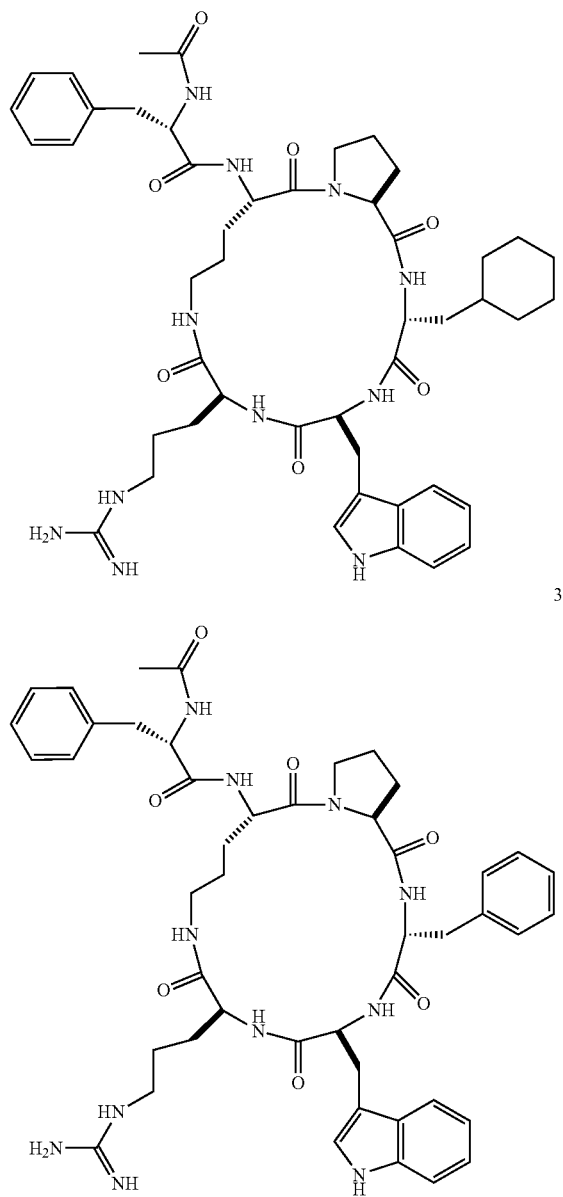

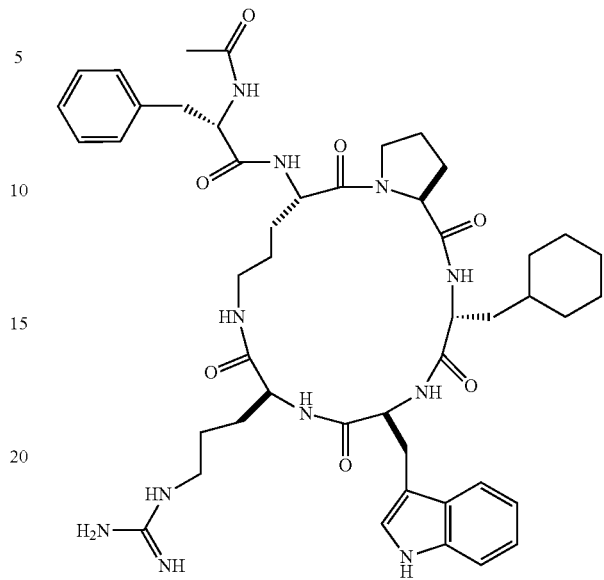

and

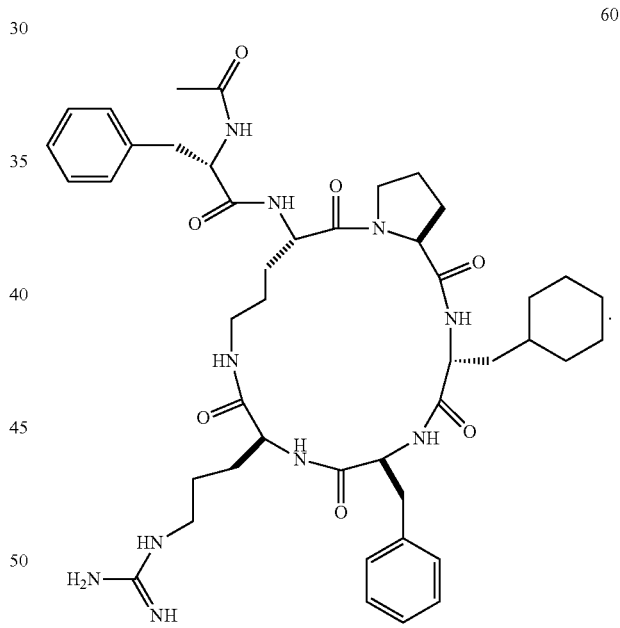

We have found that all of the compounds of formula I which have so far been tested have broadly similar pharmacological activities, although the physicochemical properties, potency, and bioavailability of the individual compounds varies somewhat, depending on the specific substituents.

The general tests described in PCT/AU98/00490 and PCT/AU02/01427 may be used for initial screening of candidate inhibitor of G protein-coupled receptors, and especially of C5a receptors.

The invention will now be described in detail by way of reference only to the following non-limiting examples and figures.

Example 1

Effect of a C5A Receptor Antagonist on L-Name-Induced Cardiac Fibrosis

Male Wistar rats (8 weeks old) were obtained from the Central Animal Breeding House of The University of Queensland. The rats were administered a C5a receptor antagonist designated PMX53, which has the formula:

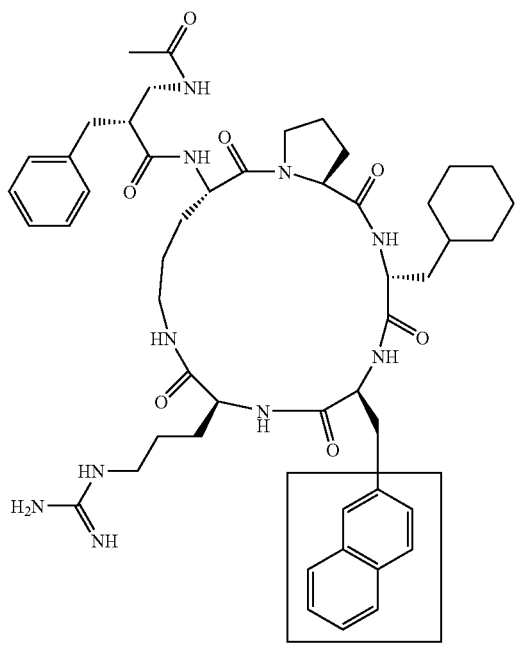

This agent was administered at a dosage of 1 mg/kg/day orally for 4 days before rats were additionally treated with nitro-L-arginine methyl ester (L-NAME) for 4 weeks, i.e. a total duration of treatment of antagonist of 32 days. L-NAME administration produces hypertension and cardiac remodelling as a result of inhibition of the production of nitric oxide (NO).

L-NAME was administered at a concentration of 400 mg/l in the drinking water for 4 weeks to give a mean daily intake of 18.7±0.4 mg L-NAME (41.4±0.8 mg/kg mean body weight). Body weight and food and water intakes were measured daily.

Figure 1B:
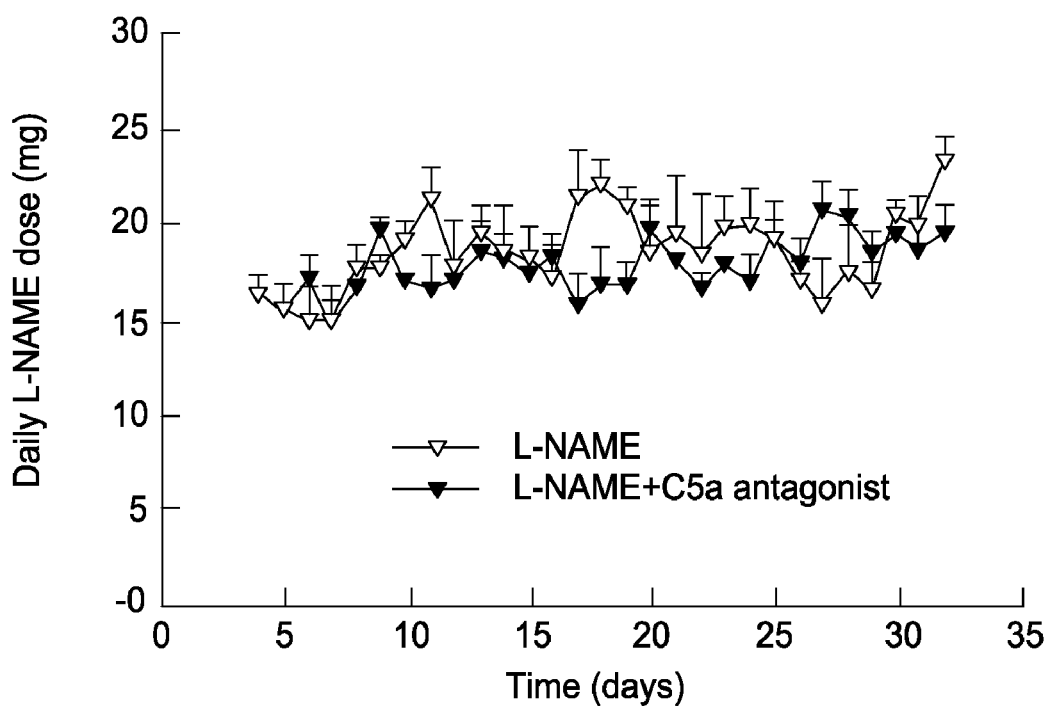
FIG. 1b shows a comparison of the daily L-NAME intake for L-NAME and L-NAME+C5a receptor antagonist treated rats.
Figure 2:
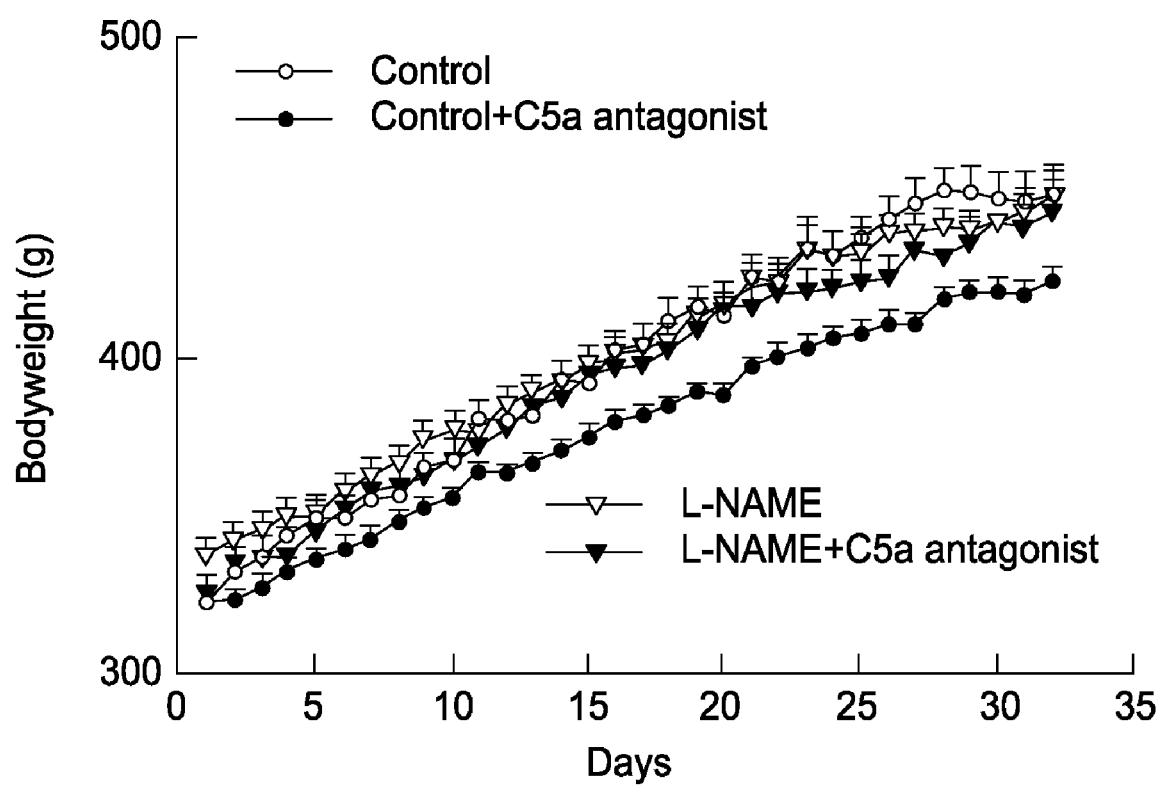
FIG. 2 shows a comparison of the body weight of control rats and rats treated with control agent+C5a antagonist, L-NAME and L-NAME+CSa antagonist. Values are expressed as mean±SEM. The arrow indicates initiation of L-NAME treatment.

Neither L-NAME nor C5a receptor antagonist treatment altered water intake or growth rate, as shown in FIGS. 1 and 2.

Figure 3:
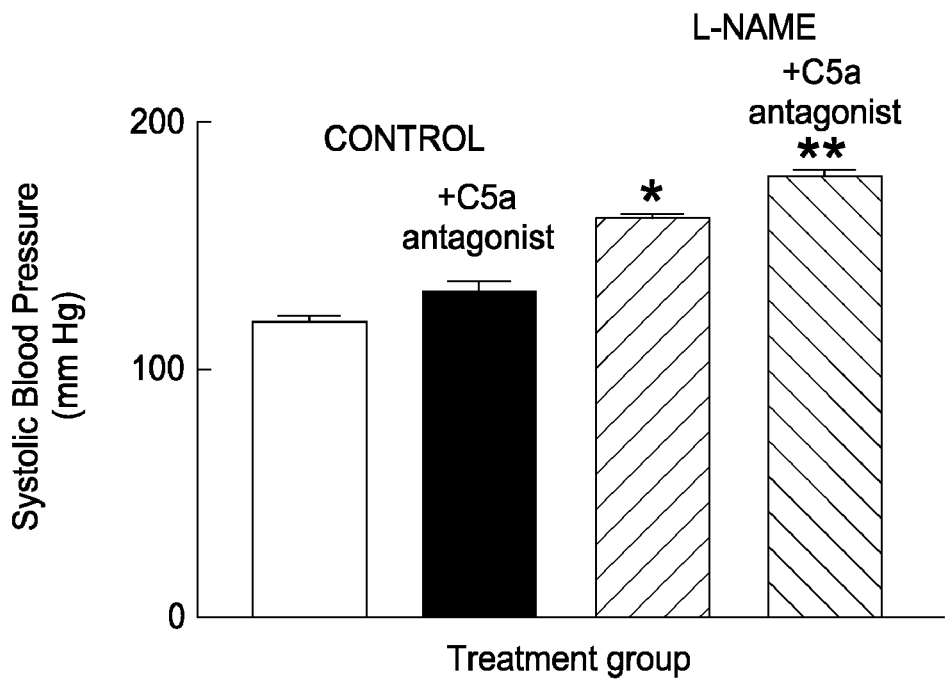
FIG. 3 shows a comparison of systolic blood pressure measurements of control, control+C5a antagonist, L-NAME and L-NAME+C5a antagonist treated rats at day 32. Values expressed as mean±SEM. *$p<0.05$ compared to control. **$p<0.05$ compared to L-NAME.
Figure 4:
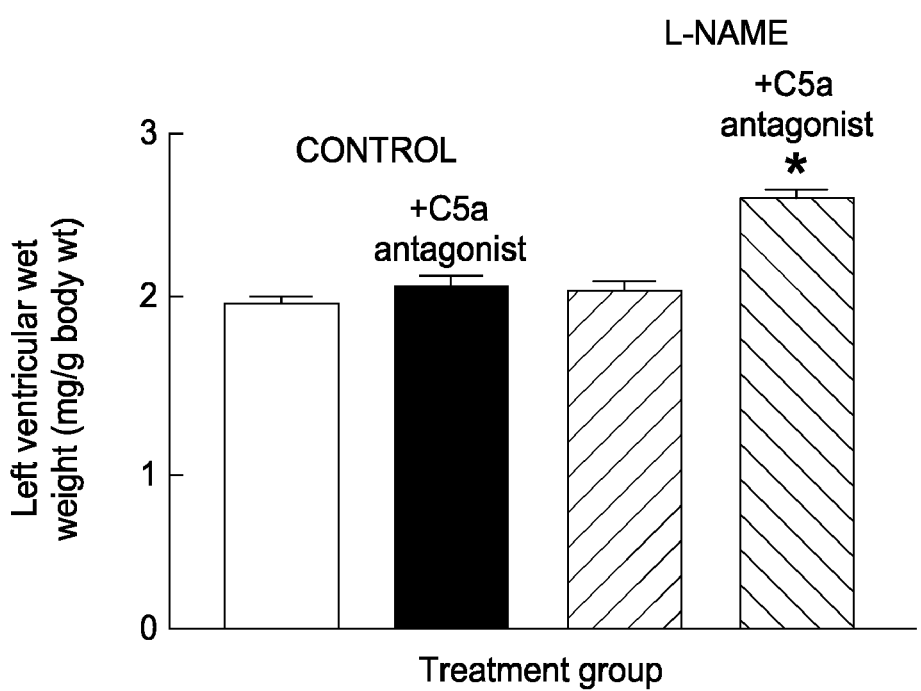
FIG. 4 shows a comparison of the left ventricular wet weight of control, control+C5a antagonist, L-NAME and L-NAME+C5a antagonist treated rats. Values expressed as mean±SEM. *$p<0.05$ compared to control.

Systolic blood pressure was measured in selected unanaesthetised rats, using a tail-cuff method. As illustrated in FIG. 3, systolic blood pressure increased from 118±3 mmHg to 160±2 mmHg in L-NAME-treated rats without significantly altering heart rate or increasing left ventricular weight, as determined by echocardiograph or post-mortem examination, when compared to control rats. These results are shown in FIG. 4.

Similarly, right ventricular and other major organ weights were not significantly altered with L-NAME treatment.

C5a receptor antagonist treatment of L-NAME rats significantly increased systolic blood pressure by 16 mmHg to 176±3 mmHg, resulting in an increased left ventricular wet weight. Additionally, C5a receptor antagonist treatment of control rats induced a non-significant increase in blood pressure. These results are summarised in FIGS. 3 and 4. C5a receptor antagonist treatment of both control and L-NAME rats did not significantly alter wet weights of the remaining major organs.

After 4 weeks of L-NAME treatment, heart function was determined in vivo by echocardiography and in vitro using the isolated Langendorff heart preparation described below. Collagen deposition was measured by image analysis using laser confocal microscopy of picrosirius red-stained cardiac slices, as described below.

Rats were euthanased with pentobarbitone (100 mg/kg ip). Blood was taken from the abdominal vena cava, centrifuged and the plasma frozen. Plasma glucose was measured by Precision Plus Blood Glucose Electrodes (Medisense, Abbott Laboratories); plasma $Na^+$ and $K^+$ were measured by flame photometry.

a) Collagen Distribution

Figure 5A:
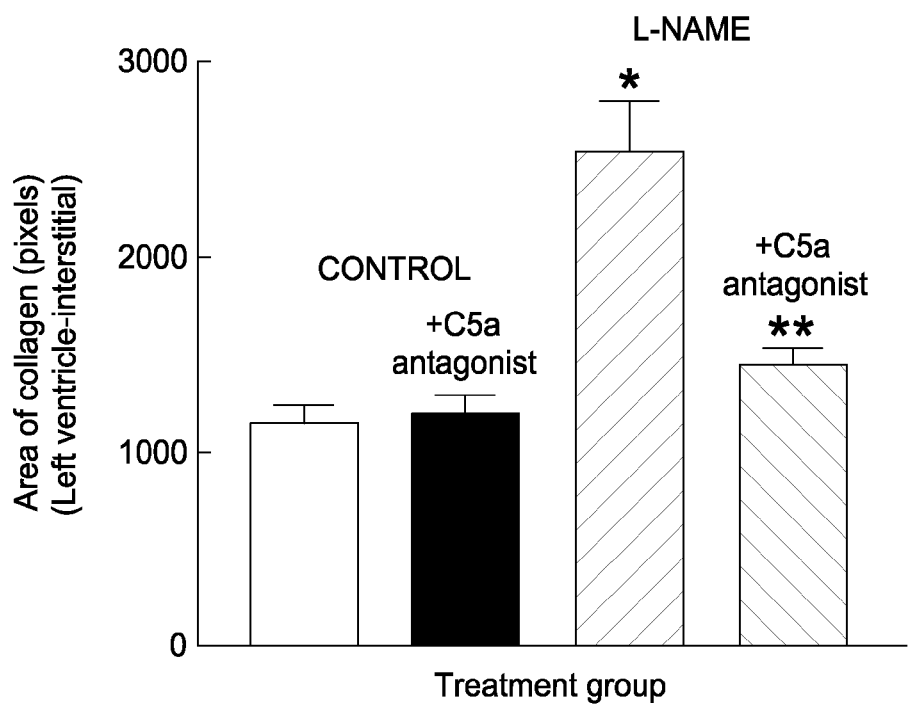
FIG. 5A and FIG. 5B show a comparison of the interstitial collagen deposition in the left ventricle of control, control+C5a antagonist, L-NAME and L-NAME+C5a antagonist treated rats. Values are expressed as mean±SEM. *$p<0.05$ compared to control; ** $p<0.05$ compared to L-NAME.
Figure 5B:
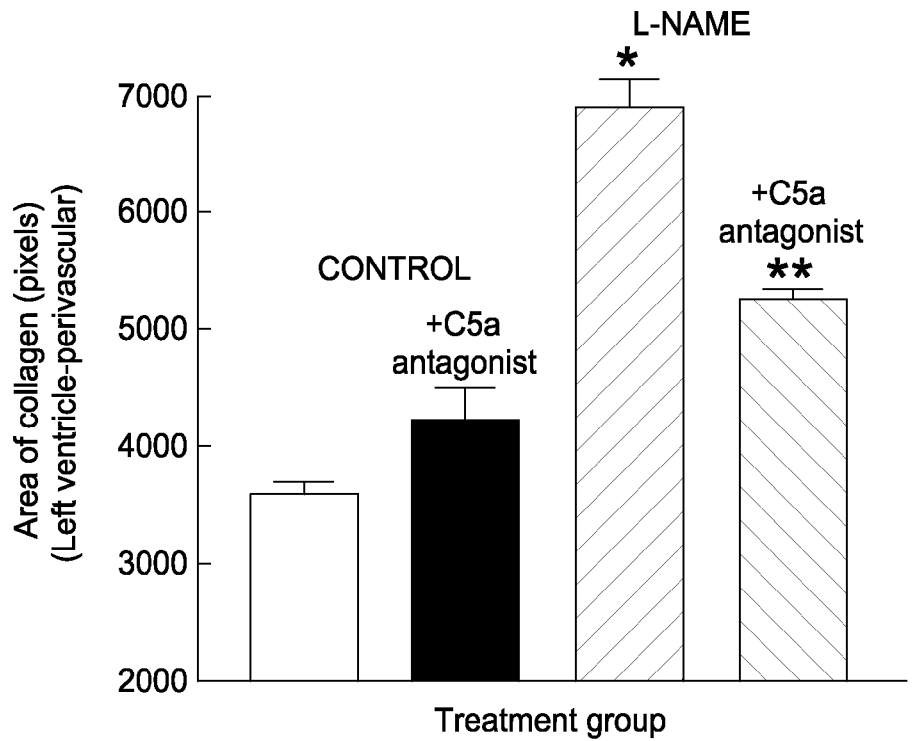
Figure 6A:
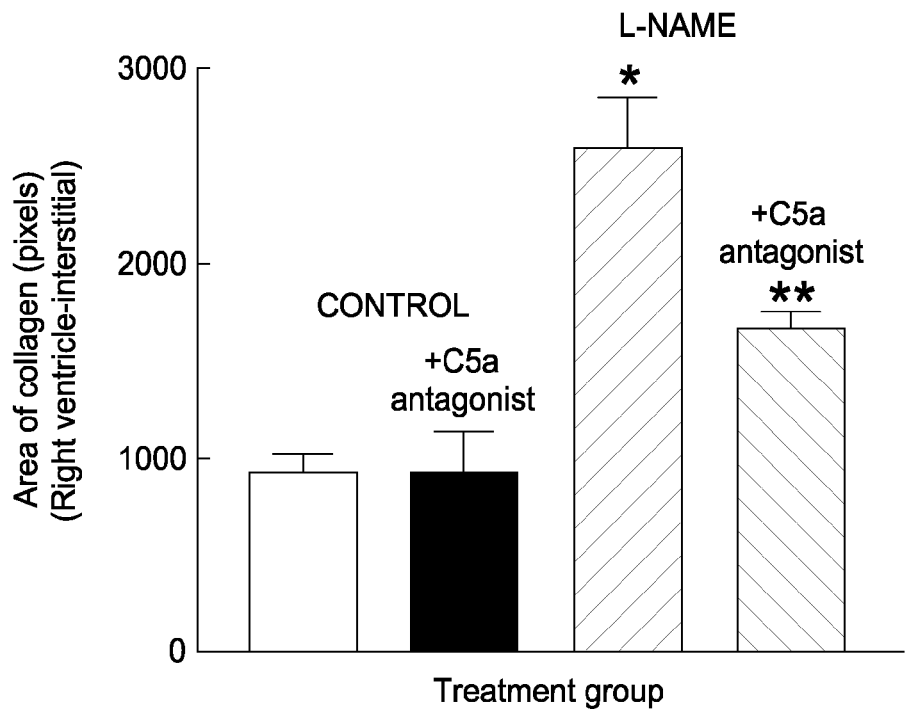
FIG. 6A and FIG. 6B show a comparison of interstitial collagen deposition in the heart ventricles of control, control+C5a antagonist, L-NAME and L-NAME+C5a antagonist treated rats. Values are expressed as mean I SEM. *$p<0.05$ compared to control; ** $p<0.05$ compared to L-NAME.
Figure 6B:
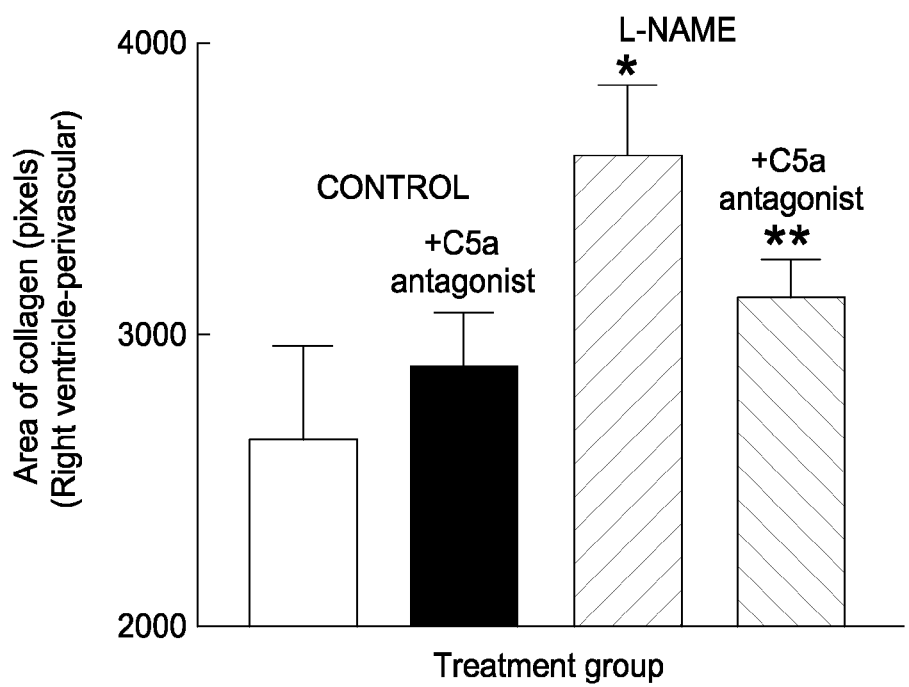
Figure 7A:
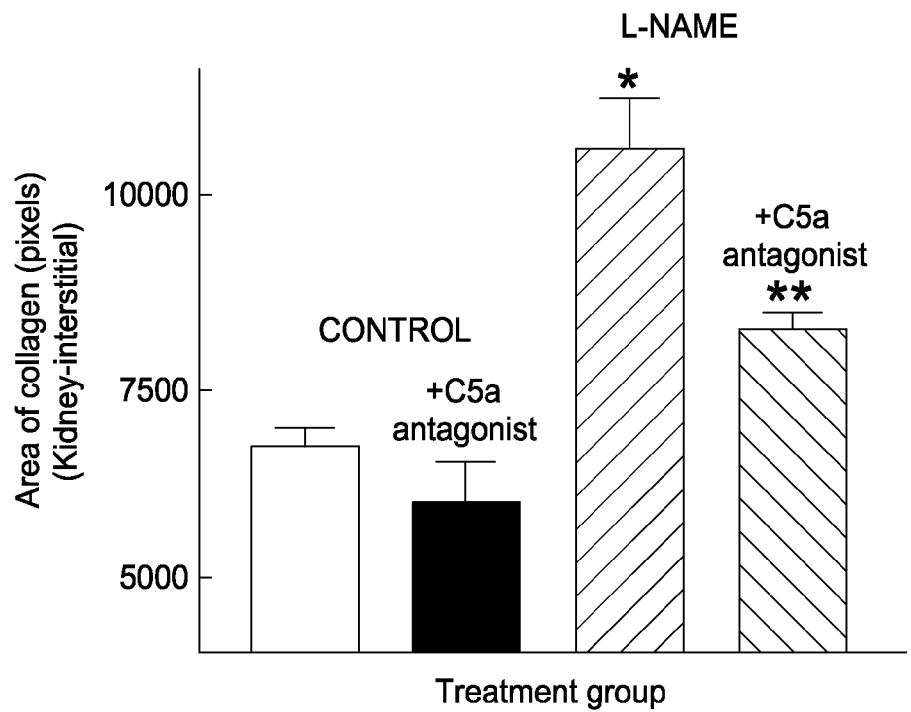
FIG. 7A and FIG. 7B show a comparison of collagen deposition in the kidneys of control, control+C5a antagonist, L-NAME and L-NAME+C5a antagonist treated rats. Values are expressed as mean I SEM. *$p<0.05$ compared to control; ** $p<0.05$ compared to L-NAME.
Figure 7B:
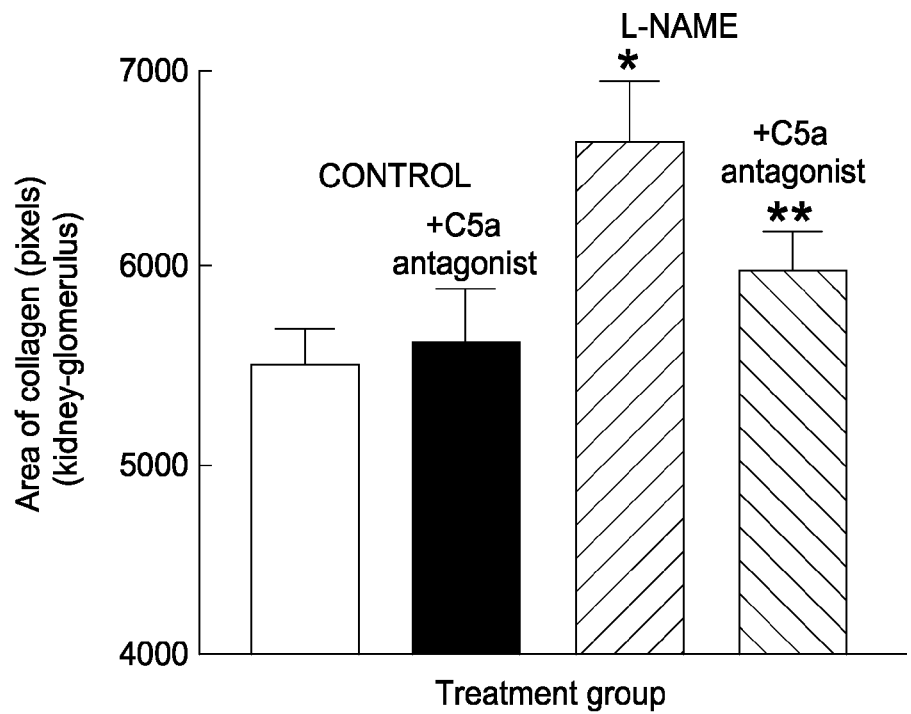
Figure 8A:
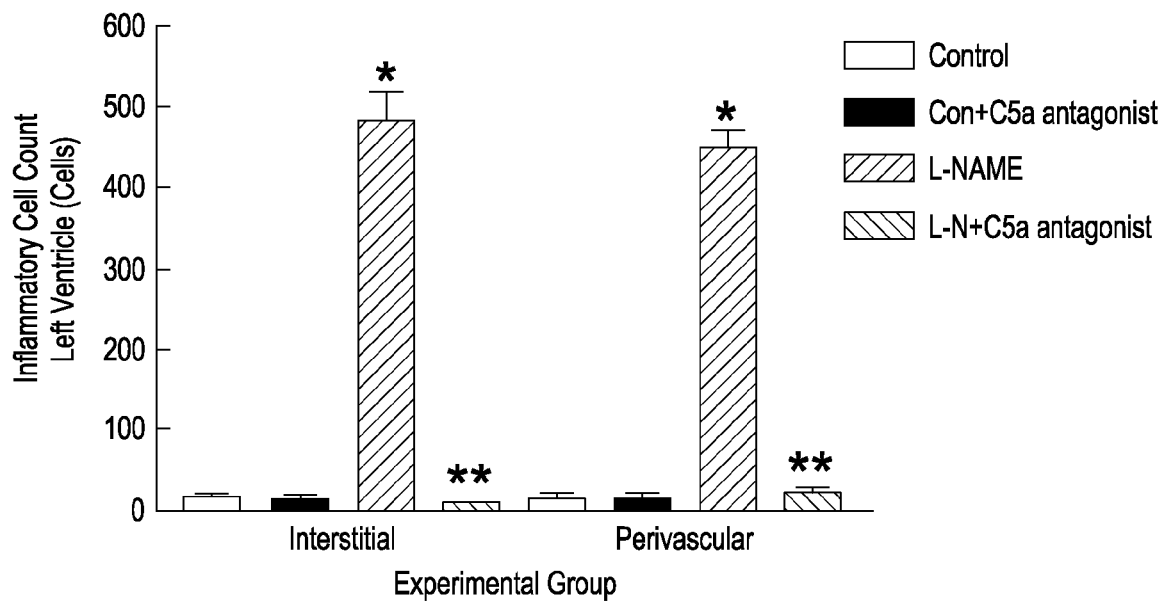
FIG. 8A and FIG. 8B show a comparison of inflammatory cell count in the heart ventricles of control, control+C5a antagonist, L-NAME and L-NAME+C5a antagonist treated rats. Values are expressed as mean±SEM. *$p<0.05$ compared to control; ** $p<0.05$ compared to L-NAME.
Figure 8B:
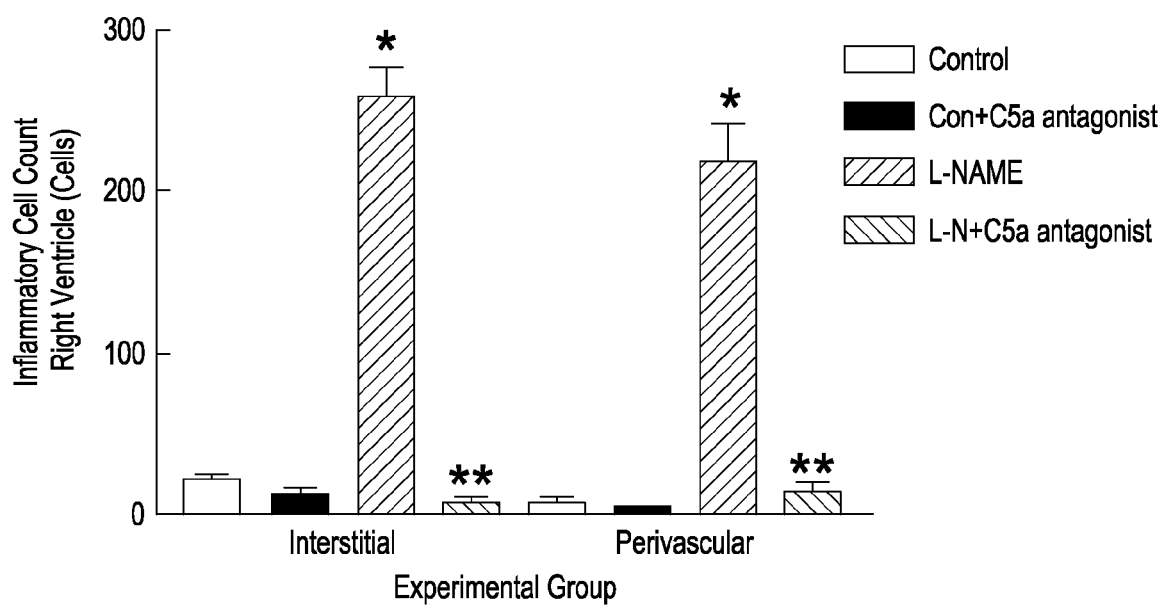
Figure 9A:
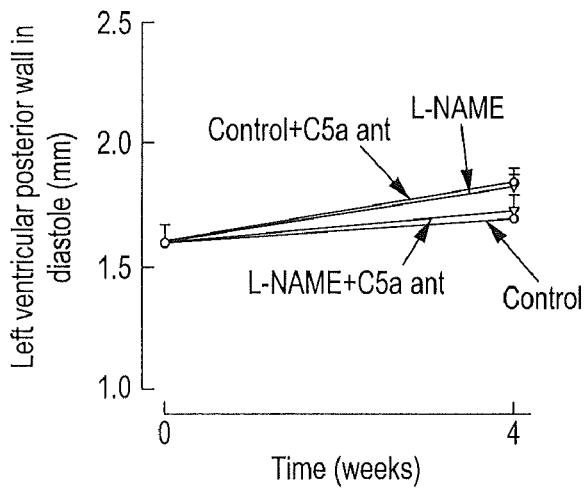
FIG. 9A, FIG. 9B, FIG. 9C, FIG. 9D and FIG. 9E summarize echocardiographic data for control, control+C5a antagonist, L-NAME and L-NAME+CSa receptor antagonist treated rats. Values are expressed as mean±SEM. *$p<0.05$ compared to control; ** $p<0.05$ compared to L-NAME.
Figure 9B:
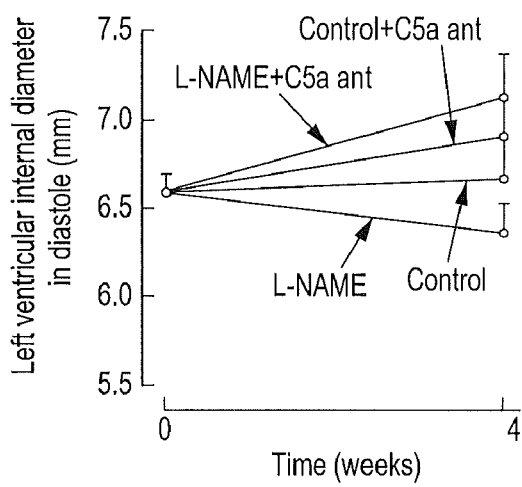
Figure 9C:
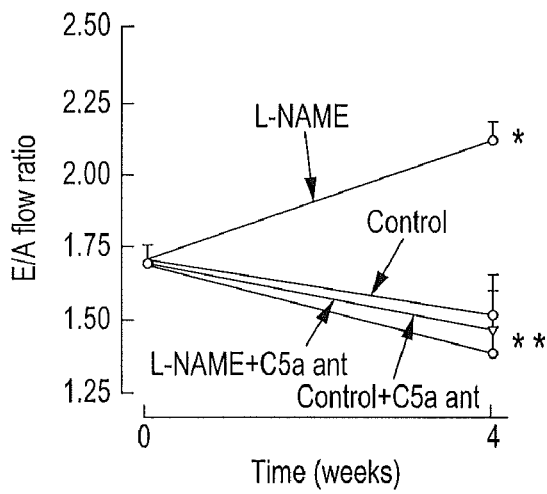
Figure 9D:
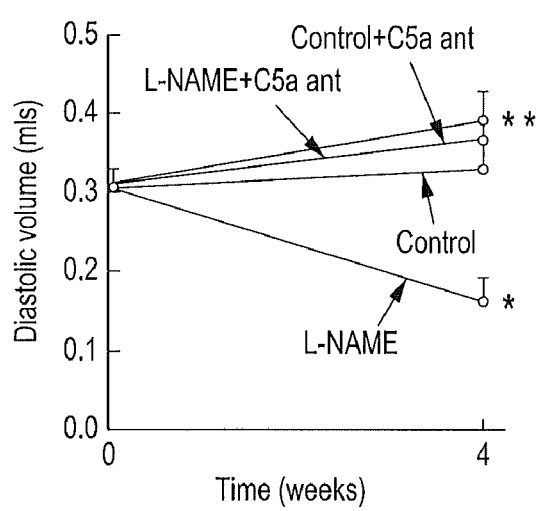
Figure 9E:
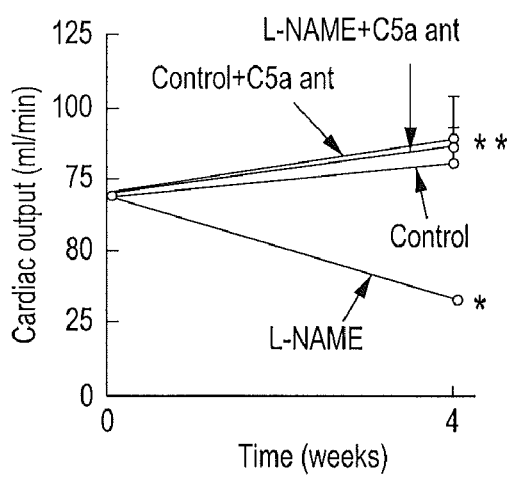

Collagen distribution was determined by image analysis of sections of heart and kidney stained with picrosirius red (0.1% Sirius Red F3BA in picric acid), which selectively stains fibrillar collagen. Slides were left in 0.2% phosphomolybdic acid for 5 minutes, washed, and left in picrosirius red for 90 minutes, then in 1 mM HCl for 2 minutes and 70% ethanol for 45 seconds. The stained sections were analyzed with an Image Pro plus analysis program using an Olympus BH2 microscope, with results expressed as a percentage of red area in each screen. At least 4 areas were examine in each heart. The results are presented in FIGS. 5, 6 and 7.

Image analysis showed an increase of 108% in interstitial collagen and an 87% increase in perivascular collagen in the left ventricle of L-NAME treated rats when compared to controls. Similarly, a significant increase in collagen levels was observed in the right ventricle, where a 175% increase in interstitial and a 37% increase in perivascular collagen content occurred. L-NAME treatment also significantly increased the collagen content by 55% in the tubulointerstitial areas of the kidneys with a smaller increase in glomerular spaces.

C5a receptor antagonist treatment attenuated the increased collagen deposition. In C5a antagonist treated rats, L-NAME treatment produced 23% and 43% of the increase observed in rats treated with L-NAME only when comparing the left ventricular interstitial and perivascular areas respectively. Similar results were observed in the right ventricle, where C5a receptor antagonist treatment of L-NAME restricted collagen deposition to 44 and 37% in the interstitial and perivascular areas respectively. In the kidneys, C5a antagonist administration to L-NAME rats restricted collagen deposition to 30% in the interstitium and normalized the increase in glomerular collagen concentrations observed in L-NAME treated rats.

As illustrated in FIG. 9, L-NAME treatment resulted in a large inflammatory cell infiltration in both the left and right ventricles. A 30-fold increase in inflammatory cell population was observed in the both left and right ventricular interstitial and perivascular areas following L-NAME treatment. C5a receptor antagonist treatment totally prevented inflammatory cell infiltration into left or right ventricles following L-NAME treatment. No information is so far available on inflammatory cell type or kidney infiltration.

b) Echocardiographic Analysis

Cardiac function was estimated in vivo using echocardiography, using conventional methods.

Although L-NAME treatment did not significantly increase left ventricular weight, echocardiographic M-mode measurements showed that L-NAME treatment had triggered cardiac remodelling, increasing the left ventricular wall thickness and decreasing the left ventricular internal diameter in diastole. Further L-NAME treatment significantly increased the ratio of early (E) to atrial (A) mitral valve inflow rates (E/A ratio), and significantly decreased diastolic volume and cardiac output. Fractional shortening and ascending aortic flow rates were not significantly altered by L-NAME treatment. Thus L-NAME treatment induces cardiac remodelling, with minor changes in systolic function and an improved diastolic function.

C5a receptor antagonist treatment of control rats did not significantly alter any parameter measured by echocardiographic analysis. C5a receptor antagonist treatment of L-NAME rats normalised the increase in left ventricular wall thickness and decreased left ventricular internal dimensions. This treatment also significantly normalised the E/A ratio, diastolic volume and cardiac output. These results are presented in FIG. 9.

c) Isolated Langendorff Heart Preparation

The Langendorff isolated heart preparation was used to determine the diastolic stiffness of the left ventricles ex vivo.

Rats were anaesthetised with sodium pentobarbitone (100 mg/kg ip) and heparin (2000 IU) was administered via the femoral vein. After allowing 2 minutes for the heparin to fully circulate, the heart was excised and placed in cooled (0° C.) crystalloid perfusate (Krebs-Henseleit solution of the following composition in mM: NaCl 118, KCl 4.7, $MgSO_4$ 1.2, $KH_2PO_4$ 1.2, $CaCl_2$ 2.3, $NaHCO_3$ 25.0 glucose 11.0). The heart was then attached to the cannula with the tip of the cannula positioned immediately above the coronary ostia of the aortic stump, and perfused in a non-recirculating Langendorff fashion at 100 cm of hydrostatic pressure. The buffer temperature was maintained at 35° C. The hearts were punctured at the apex to facilitate thebesian drainage and paced at 250 bpm.

A balloon catheter was inserted in the left ventricle via the mitral orifice for measurement of left ventricular developed pressure. The catheter was connected via a three-way tap to a micrometer syringe and to a Statham P23 pressure transducer. The outer diameter of the catheter was similar to the mitral annulus to prevent ejection of the balloon during the systolic phase. After a 10 minute stabilisation period, steady-state left ventricular pressure was recorded from isovolumetrically beating hearts. Increments in balloon volume were applied to the heart until left ventricular end-diastolic pressure reached approximately 30 mmHg.

To assess myocardial stiffness in isolated Langendorff hearts, stress ($\sigma$, dyne/cm2) and tangent elastic modulus (E, dyne/cm2) for the midwall at the equator of the left ventricle were calculated by assuming spherical geometry of the ventricle and considering the midwall equatorial region as representative of the remaining myocardium:

$$\sigma = \frac{VP}{W}\left(1 + \frac{4(V+W)}{[V^{1/3} + (V+W)^{1/3}]^3}\right)$$

$$E = 3\left\{\frac{VP}{W} - \sigma + \frac{\left[\frac{\sigma}{V} + \frac{(W\sigma - VP)}{W(V+W)} + \frac{\sigma \cdot dP}{P \cdot dV}\right] \times [V^{1/3} + (V+W)^{1/3}]}{[V^{-2/3} + (V+W)^{-2/3}]}\right\}$$

where V is chamber volume (ml), W is left ventricular wall volume (0.943 ml/g ventricular weight) and P is end diastolic pressure (dyne/cm2=7.5×10−4 mmHg). Myocardial diastolic stiffness is calculated as the diastolic stiffness constant (k, dimensionless), the slope of the linear relation between E and $\sigma$ (Mirsky and Parmley, 1973). To assess contractile function, maximal +dP/dt was calculated at a diastolic pressure of 5 mmHg.

Figure 10:
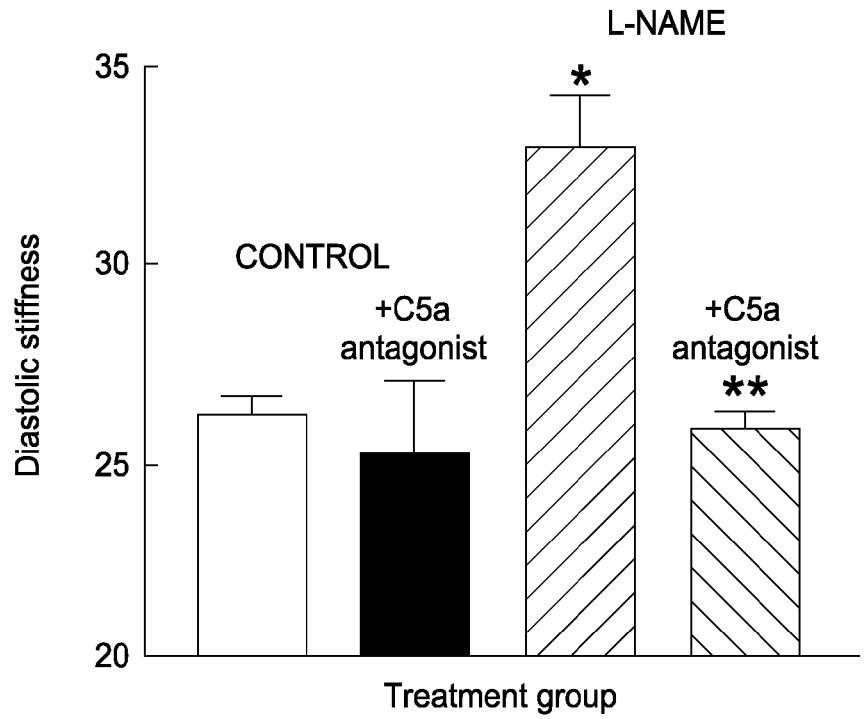
FIG. 10 shows a comparison of diastolic stiffness constants for control, control+C5a antagonist, L-NAME and L-NAME+C5a antagonist treated rats. Values expressed as mean±SEM. *p<0.05 compared to control; **p<0.05 compared to L-NAME.

The results are shown in FIG. 10. All results are given as mean±SEM of at least 6 experiments. The negative log EC50 of the increase in either force of contraction in mN or rate of contraction in beats/min was determined from the concentration giving half-maximal responses in individual concentration-response curves. Renal function results were corrected for kidney wet weight measured at the end of the experiment. These results were analysed by two-way analysis of variance followed by the Duncan test to determine differences between treatment groups and by paired or unpaired t-tests as appropriate; p<0.05 was considered significant.

At the end of the experiment, the atria and right ventricle were dissected away and the weight of the left ventricle plus septum was recorded.

Figure 11:
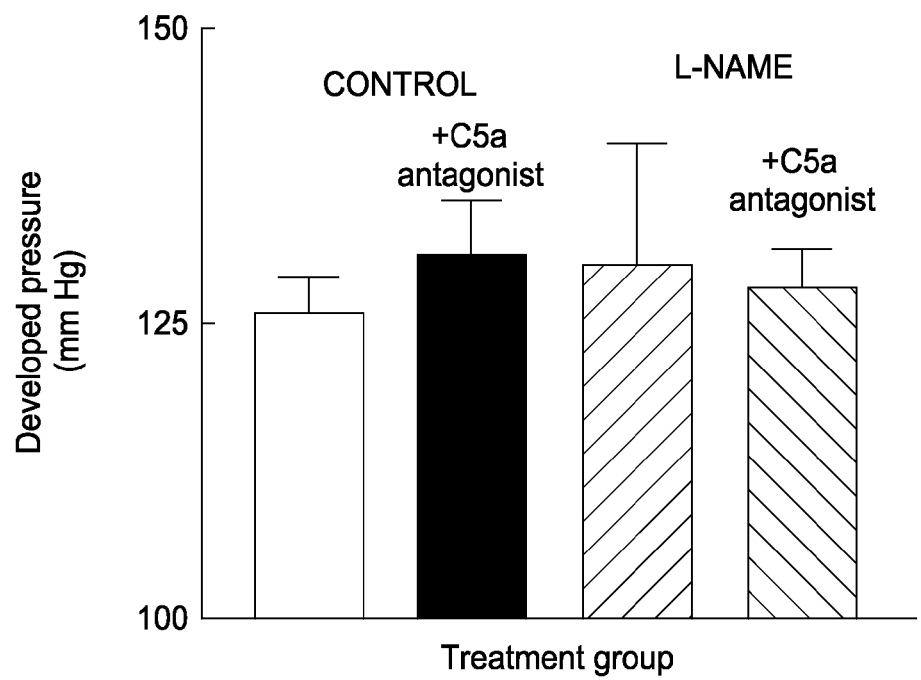
FIG. 11 shows a comparison of developed pressure for control, control+C5a antagonist, L-NAME and L-NAME+C5a antagonist treated rats. Values are expressed as mean±SEM.

L-NAME treatment markedly increased the diastolic stiffness constant of the ventricles when compared to controls. Developed pressure and contractility were not altered by L-NAME treatment. C5a receptor antagonist treatment prevented the increased diastolic stiffness constant of L-NAME rats without altering contractility or developed pressure. These results are presented in FIGS. 10 and 11.

d) Isolated Cardiac Muscles and Thoracic Aortic Rings

The heart is removed under anaesthesia. The right atria and papillary muscles from the left ventricle are removed and suspended in organ baths a arresting tension of 5-10 mN adjusted to give the maximum twitch response. Tissues are bathed in a modified Tyrode's solution, containing the following concentrations of salts in mM: NaCl 136.9, KCl 5.4, $MgCl_2$ 1.05, $CaCl_2$ 1.8, $NaHCO_3$ 22.6, $NaH_2PO_4$ 0.42, glucose 5.5, ascorbic acid 0.28, sodium edetate 0.05, bubbled with 95% $O_2$/5% $CO_2$, and stimulated at 1 Hz at 35° C. as previously described (Brown et al, 1991a). Cumulative concentration-response curves are measured for noradrenaline and, following washout and re-equilibration, for calcium chloride. At the end of the experiment, papillary muscle dimensions are measured under the loading conditions of the experiment; all tissues are blotted and weighed.

Thoracic aortic rings (approximately 4 mm in length) are suspended with a resting tension of 10 mN (Brown et al, 1991b) and contracted twice with isotonic KCl (100 mM). The presence of endothelium is demonstrated by addition of acetylcholine ($1 \times 10^{-5}$ M). Cumulative contraction responses to noradrenaline are measured. Separate thoracic aortic rings are perfused with 10% neutral buffered formalin, embedded in wax and stained with haemotoxylin and eosin. Image analysis using a Wild-Leitz MD30+ system is used to calculate the wall area of the thoracic aorta.

Example 2

Effect of PMX53 on Bleomycin-Induced Pulmonary Fibrosis

Both acute and chronic diseases which induce inflammation in the lung can lead to an irreversible process characterized by pulmonary fibrosis. The effect of PMX-53 on a rat model of pulmonary fibrosis was assessed, using methods were adapted from Taylor et al (2002).

Bleomycin is an antineoplastic agent which is a well-known cause of pulmonary fibrosis in humans (Thrall et al, 1978). Bleomycin-induced pulmonary fibrosis in rats is a well-established model, which has a short experimental period and high success rates. Bleomycn induces toxic injury to Type I alveolar epithelial cells (AEC), which causes release of TGF-β, PGE$_2$, granulocyte-macrophage colony stimulating factor (GM-CSF), and insulin-like growth factors etc. This induces a massive activation of inflammatory cells such as PMNs, macrophages and mesenchymal cells such as fibroblasts, which contribute to an overaggressive repair process, leading to fibrosis in the lung. PMX53 is a C5a receptor antagonist, which effectively inhibits the infiltration and the activation of inflammatory cells, such as PMNs, monocytes, macrophages, and therefore reduces the release of reactive oxygen species and inflammatory mediators such as IL-1 and PLA$_2$. As a result, local tissue damage is prevented by a reduction of release of several factors, such as leukotrienes, and prostaglandins. We investigated whether PMX53 antagonists had any inhibitory effect on bleomycin-induced pulmonary fibrosis.

Male Wistar rats, 6 weeks of age, were used. The rats were divided into 5 groups:

Group 1: bleomycin instillation only (n=9)
Group 2: saline instillation only (n=3)
Group 3: PMX53 at a dose rate of 10 mg/kg in 200 µl water p.o. (gavage daily) and bleomycin instillation (n=9)
Group 4: PMX53 (dose as for Group 3) p.o. and saline instillation (n=3).
Group 5: Untreated rats maintained in the same environment as the other groups (n=3).

Drug-treated rats were given drug for 3 days before bleomycin administration.

One intra-tracheal instillation of bleomycin at a dose of 0.5 mg/100 g (0.7 U/100 g) in 200 µl of saline was performed on Day 1, as described by Taylor et al., (2002). Rats were anaesthetized by inhalation of 5% or less halothane via a vaporizer. After a local spray of Xylocalne to prevent airway spasm, the rats were intubated and a slow injection of bleomycin or sline control was completed. The rats were then rotated gently for about 1-2 minutes to allow the solution to diffuse evenly into both lungs (Christensen et al 2000). Rats were kept in the fume cupboard until totally recovered, and then monitored for up to 18 days. Body weight, food and water intake, and respiration were monitored daily.

Respiration was elevated as follows: Score 0, normal respiration; Score 1, increased rate of breathing; and Score 2, mouth open respiration. Rats were euthanased before the end of the experimental period, if they consistently lost more than 10% bodyweight for 48 hours, had Score 2 respiration or had Score 1 respiration for 48 hours.

At the end of this period the rats were killed by exsanguination under anaesthesia, so that the lungs were clear of blood. For each rat, the left lung was immediately frozen in liquid nitrogen and stored at −20° C. for quantitative collagen analysis using hydroxyproline assay. The right lung was fully inflated and fixed with 10% formulated formalin by airway gravity fixation at a pressure of 30 cm water for 1 minute. Haematoxylin and eosin (H&E) and Picro Sirius Red (PR) staining for collagen were performed to assess collagen deposition in the lung. For quantitation of collagen stained with PR, polarized light images were converted to grey scale, and the total number of white pixels (specific for collagen) per image was determined as a percentage of the total pixel area. The procedure was applied to a total of four fields in the alveolar area and two fields in the peribronchial area and blood vessels per sample (Wang et al, 2000). The largest lobe of the right lung (from 4 lobes) in each rat was chosen. The data was analysed using the program "Sion Image".

Hydroxyproline assay was performed by the method of Christensen et al 1 (2000). Lung tissue was excised, trimmed free of surrounding conducting airways, and homogenized in 2 mls saline. A 1 ml aliquot of lung homogenate was hydrolysed in 6N HCl (0.5 ml of homogenate and 0.5 ml of 12N HCl) at 110° C. for 12 hours; 50 µl aliquots were added to 1 ml of 14% chloramine T, 10% n-propanol, and 0.5M sodium acetate, pH 6.0. After 20 min at 22° C., 1 ml of Ehrlich's solution (1M p-dimethylaminobenzaldehyde in 70% n-propanol and 20% perchloric acid) was added and allowed to incubate at 65° C. for 15 min. Absorbance was measured at 550 nm, and the amount of hydroxyproline was determined against a standard curve generated with the use of known concentrations of reagent-grade hydroxyproline.

Data were compiled as the means±SE in the study. Tests of significance were obtained by ANOVA followed by Student-Newman-Keuls post analysis. There were two stages involved in the bleomycin-induced pulmonary fibrosis in rat model.

Figure 12A:
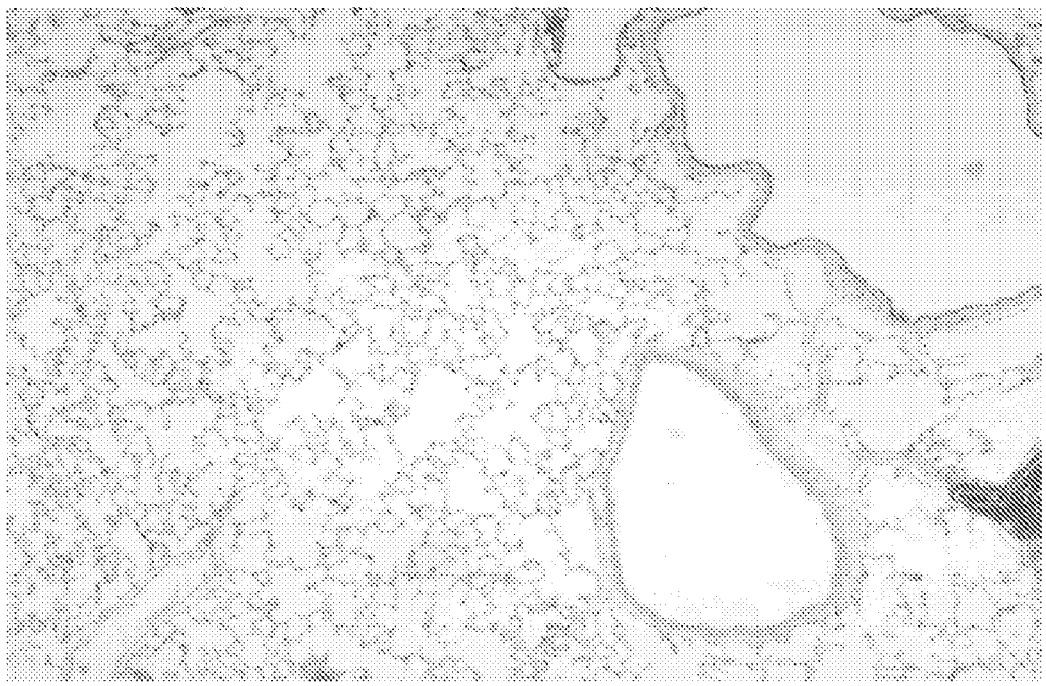
Figure 12B:
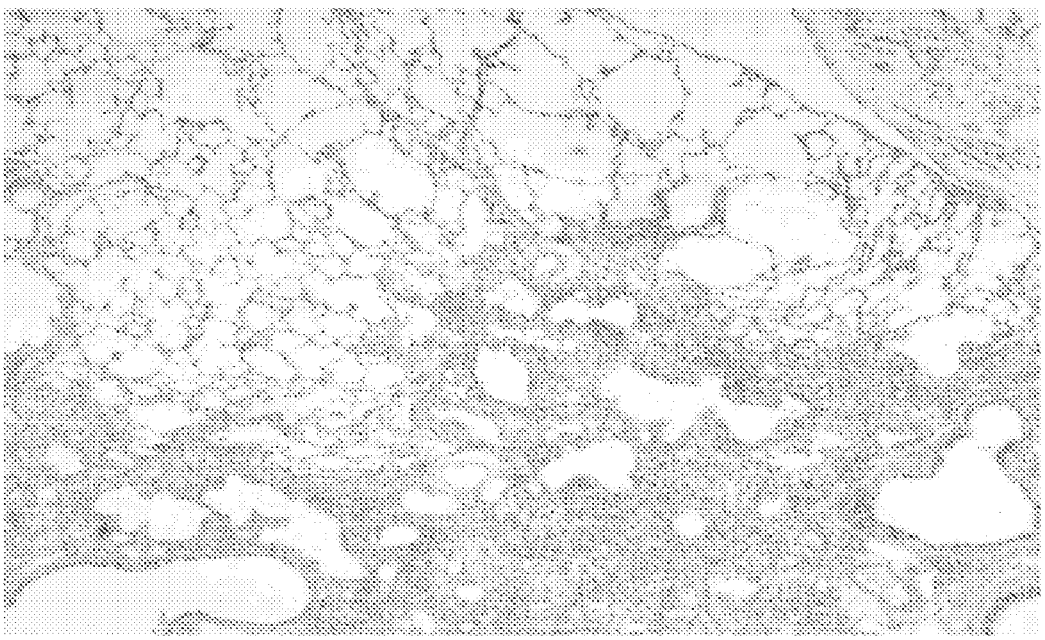
(FIG. 12B) Lung 7-9 days after intra-tracheal bleomycin instillation, showing severe patchy lesions around the airways. There was no significant difference between PMX53-treated rats and non-treated rats (n=4 in each group).

1. Acute Lung Inflammation:

Intra-tracheal instillation of bleomycin induced an acute lung inflammation in the rats, evident on Day 2-Day 3. Four of the rats from the drug-treated group and four from the non-treated group were very ill, and had to be euthanased after 7-9 days. The lungs appeared swollen, with spreading white patchy lesions, as shown in FIGS. 12 and 13. The lung weight to body weight ratio was significantly increased in bleomycin-treated rats, regardless of whether the rats were drug-treated or non-treated. The results are summarised in Table 1.

TABLE 1

Lung weight and body weight in bleomycin-induced pulmonary fibrosis (7-9 days)

| Condition | Left lung weight (g) | Body weight (g) | Ratio ×10$^{-3}$ |
|---|---|---|---|
| Normal | 0.507 ± 0.003 | 240.6 + 4.667 | 1.9 ± 0.36 |
| Bleomycin | 1.004 ± 0.04 | 226 + 8.083 | 4.47 ± 0.46** |
| Bleomycin + PMX53 | 0.974 ± 0.132 | 228 + 7.583 | 4.25 ± 1.07** |

**$P < 0.001$, n = 3, compared to normal rats.

Figure 13A:
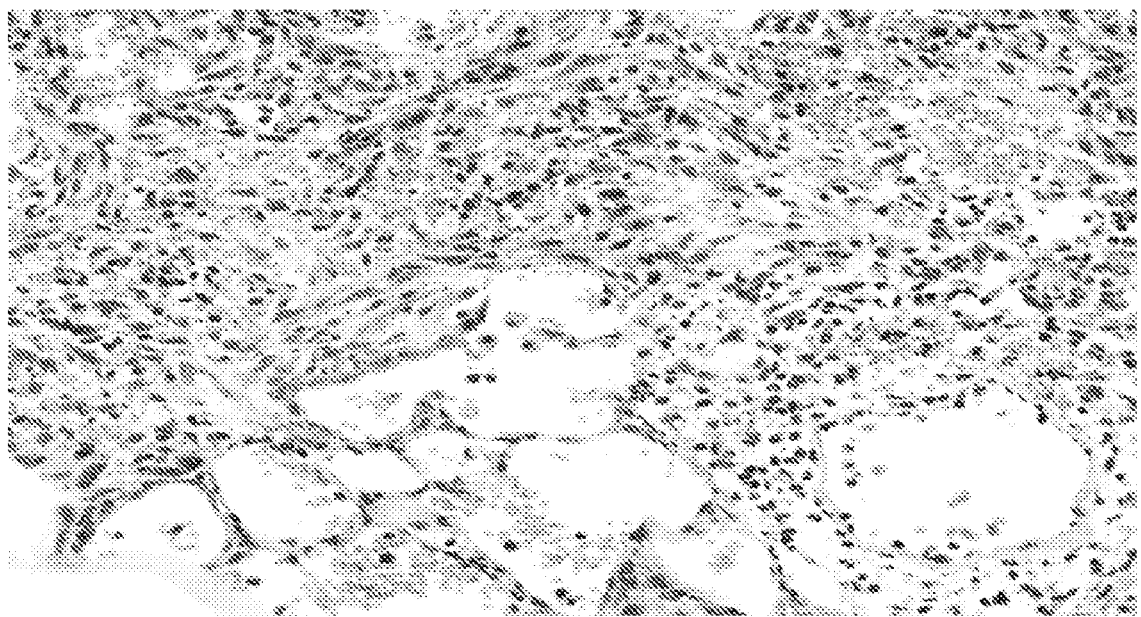
FIG. 13a shows a higher magnification view of a patchy lesion (×200) showing inflammatory cells in the alveolar space and alveolar septa, with leakage of red cells and plasma.
Figure 13B:
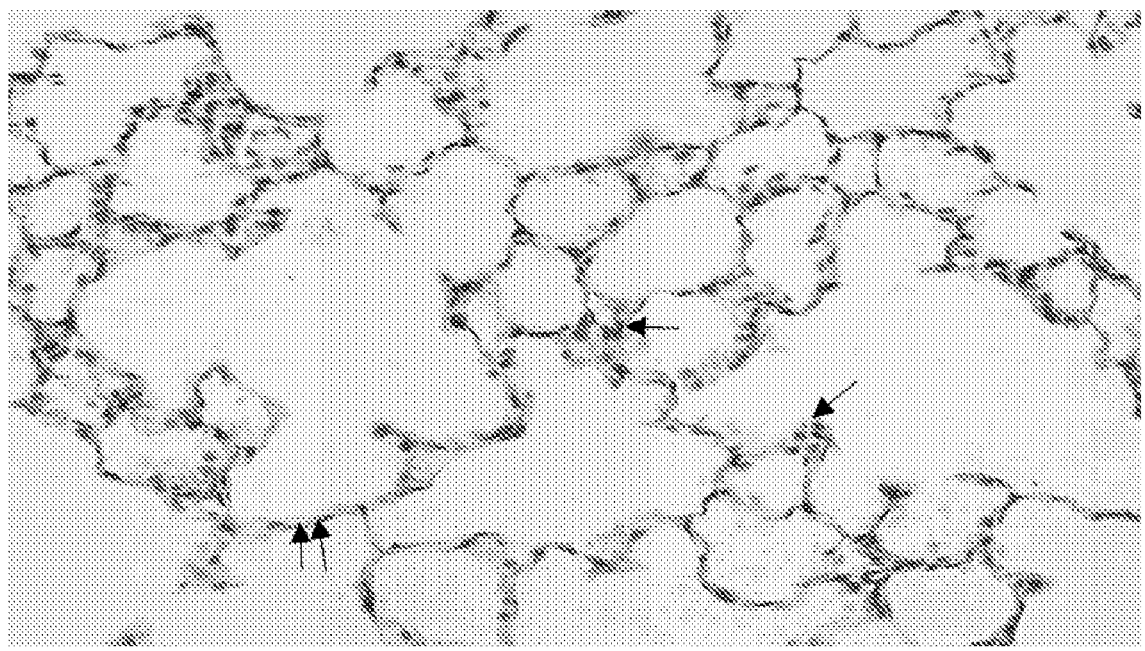
FIG. 13b shows a higher magnification view of normal lung (×200), showing the two types of alveolar epithelial cells (AECs): type I AECs (40%) are flat cells, and form 90% of the surface lining of the alveolar sacs and alveoli (double arrows). Type II AECs (60%) are rounded cells which are commonly located in obtuse angles in the polygonal alveolus (arrows) rather than the surface region. When the alveolar epithelium is exposed to certain toxic agents, particularly if there is extensive destruction of the sensitive type I AECs, type II AECs increase in size and number.
Figure 14:
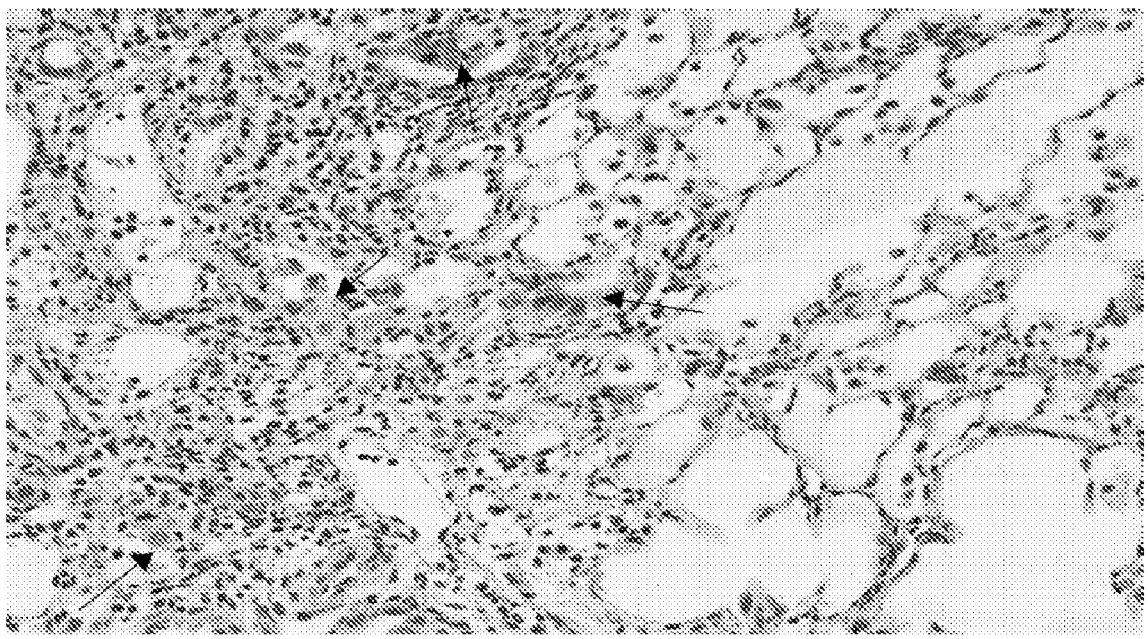
FIG. 14 shows the increased size and number of Type II alveolar epithelial cells in lungs of bleomycin-treated rats (arrows) (×200).

Under the microscope, numbers of inflammatory cells, including PMNs, macrophages, lymphocytes etc. were observed in the alveolar spaces, with massive leakage of plasma and red blood cells; this is illustrated in FIG. 13*a*. The size and number of type II AECs in the alveolar spaces was clearly increased, as shown in FIG. 13*b*, while in normal lung, the type II AECs covered only 5-10% of the surface area of the alveoli, as shown in FIG. 14.

Figure 15:
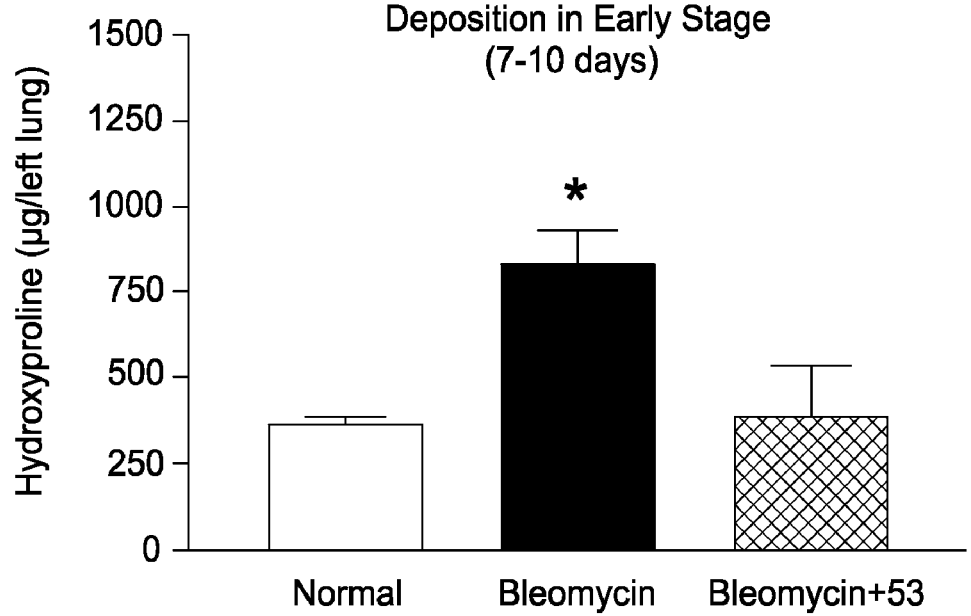
FIG. 15 shows the effect of PMX53 on bleomycin-induced collagen deposition in acute lung inflammation (7-9 days).

There was no significant difference in histology between drug-treated and non-treated groups. Collagen deposition in bleomycin instillation lungs showed a significant increase compared to normal lungs ($P<0.01$, n=3); saline instillation lungs ($P<0.01$, n=3); and saline instillation with PMX53-treated lungs ($P<0.01$, n=3). However, there was no significant difference between the drug-treated group and non-treated group ($P>0.01$, n=4). These results are summarised in FIG. 15.

2. Pulmonary Fibrosis

Figure 16:
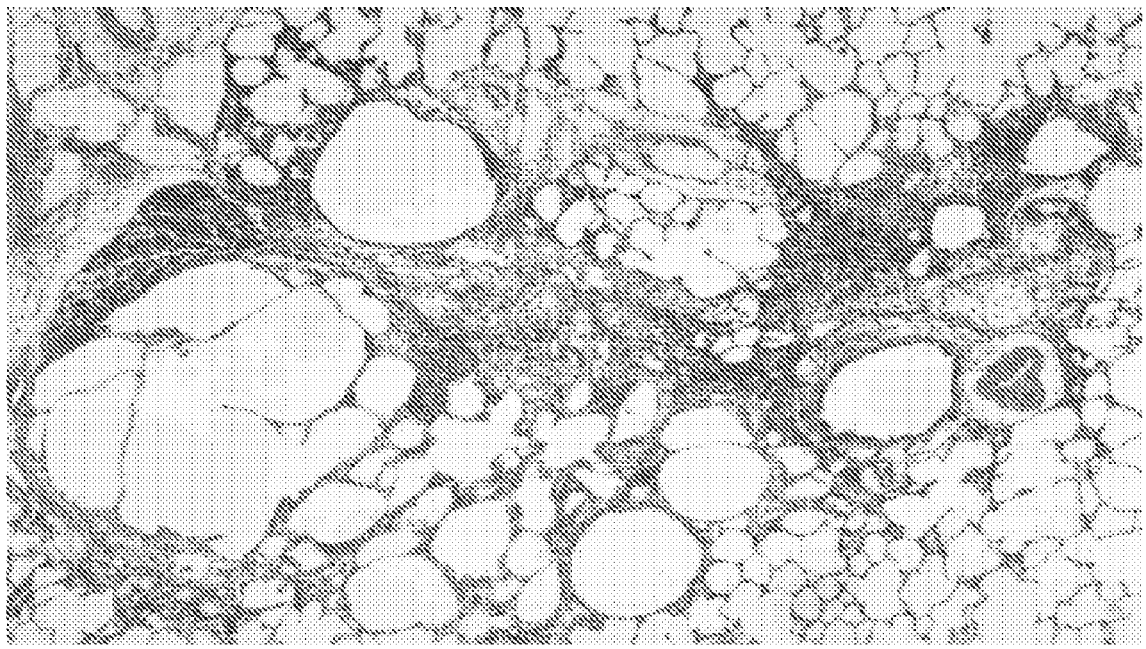
FIG. 16 shows lung tissue from a bleomycin-instilled, PMX53-treated rat 18 days after instillation, illustrating the decrease in size of patchy lesions around the airways compared to the acute inflammatory stage illustrated in FIG. 12b (×40).
Figure 17A:
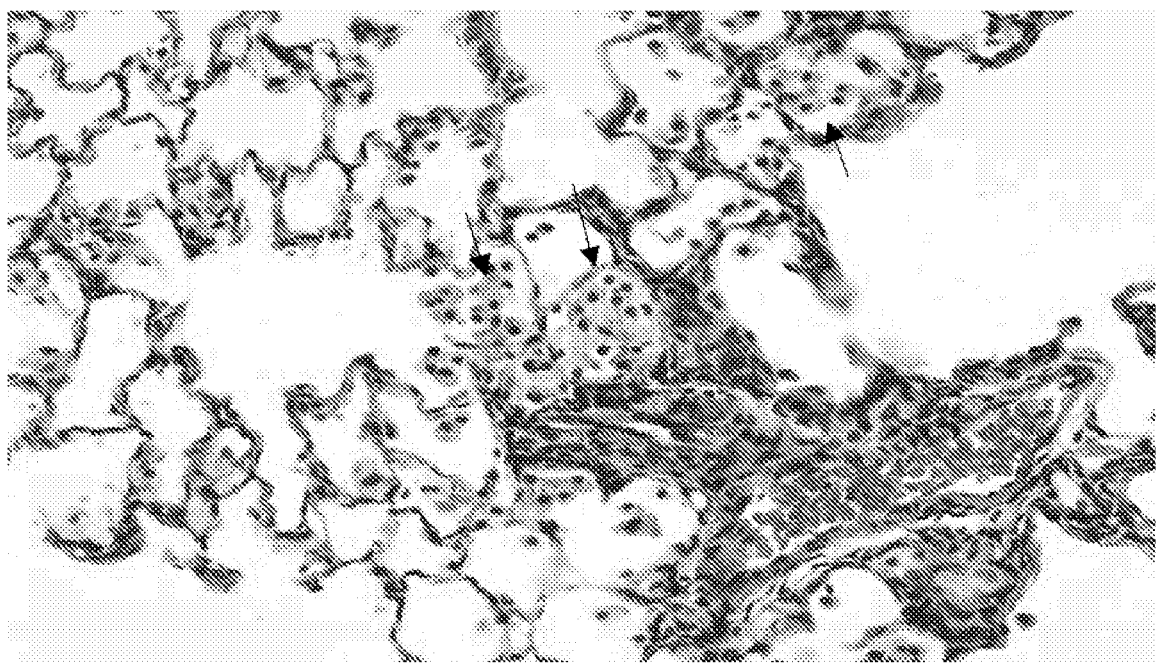
FIG. 17A and FIG. 17B show a higher magnification view (×200) of lung tissue from a non-drug treated bleomycin-instilled rat.
Figure 17B:
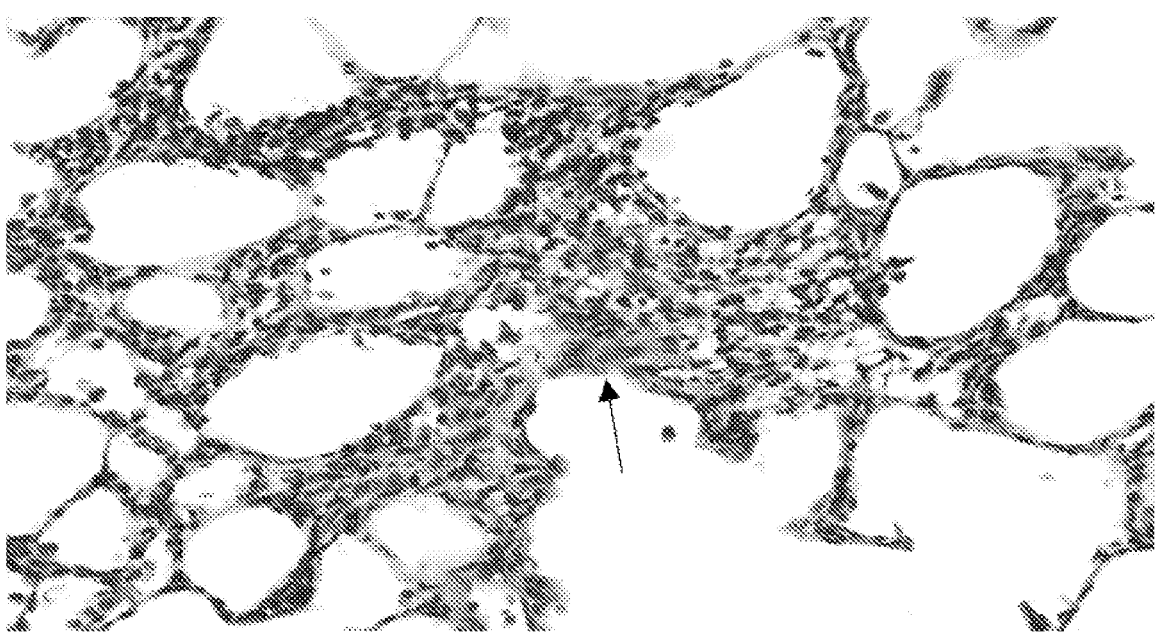
Figure 18A:
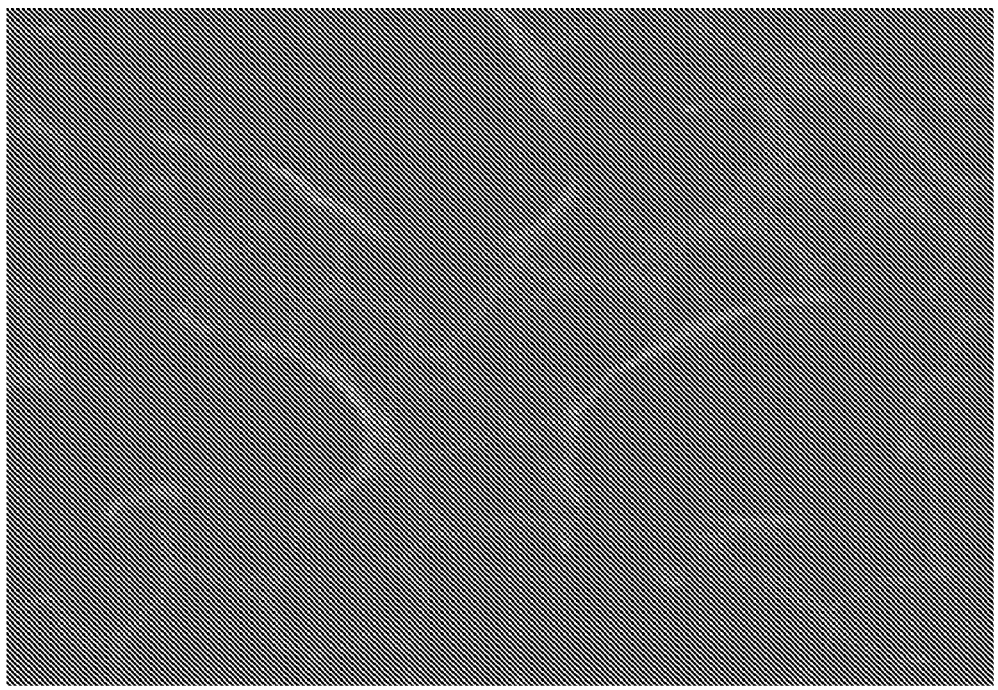
Figure 18B:
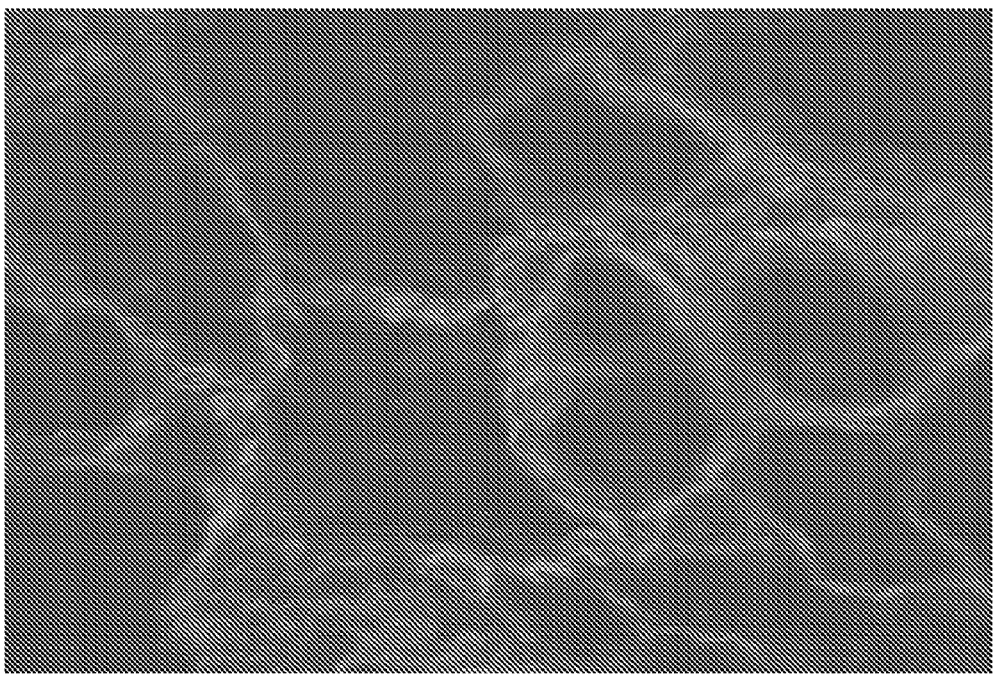
(FIG. 18B) Non-treated bleomycin-instilled rat, showing increased collagen in thickened alveolar wall.
Figure 18C:
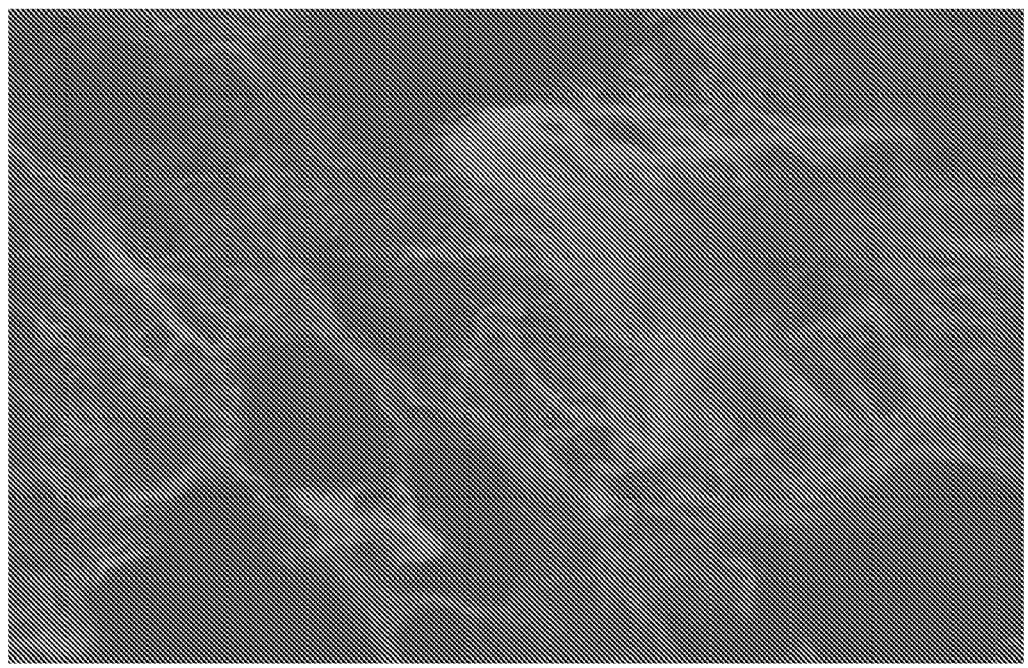

Eighteen days after intra-tracheal instillation of bleomycin, the degree of oedema was reduced in bleomycin-instilled lungs, and the lung/body weight ratio did not show a significant difference between either the bleomycin group and the non-bleomycin group, or between the drug-treated group and non-drug group (data not shown). As illustrated in FIG. 16, the inflammatory lesions in the lung became smaller and less dense in most of the rats compared with the acute inflammatory stage, whether or not the rats had received drug treatment. There were still numbers of inflammatory cells, many of which were alveolar macrophages, and red blood cells in the lung lesions, as shown in FIG. 17a. The thickness of the alveolar walls was increased, and there was some fibrinogen depositions in alveolar septa in some of the lungs, as shown in FIG. 17b. One drug-treated rat and one non-drug treated rat still had some obvious lung inflammatory lesions mixed with marked lung fibrosis lesions. It was difficult to assess the quantity of collagen deposition in the lung tissues from the H&E stained slides, because the amount of collagen and the spread of the collagen varied in each individual rat, and the number of the lesions in each lung was different. PR staining was more useful than H&E staining for assessment of collagen deposition in the lungs, as illustrated in FIGS. 21 to 30 and as summarised in Table 2.

TABLE 2

PR staining in bleomycin-induced pulmonary fibrosis (% of the total pixel area, n = 3-4)

| Saline | Bleomycin | Bleo + PMX53 |
|---|---|---|
| 0.01 | 0.01 | 1.43 |
| 0.04 | 0.21 | 0.06 |
| 0.007 | 0.78 | 0.01 |
|  | 1.73 | 0.77 |

Figure 19:
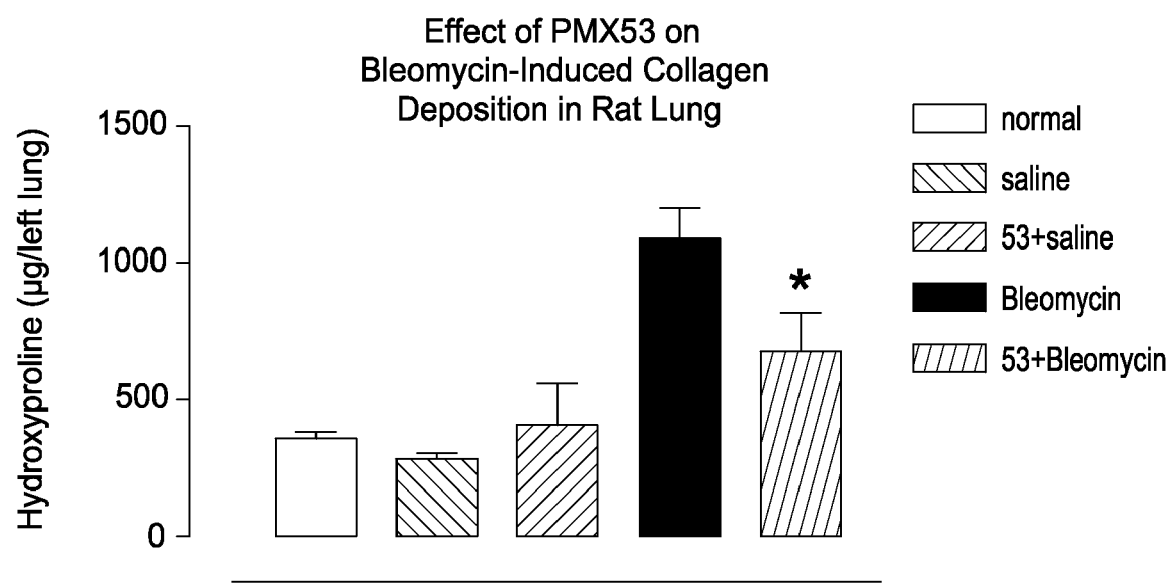
FIG. 19 shows the effect of PMX53 on bleomycin-induced collagen deposition in rat lung at 18 days after bleomycin instillation.

However, for the same reasons it was not an accurate measurement for comparison analysis of the collagen content. The hydroxyproline essay results are summarised in FIG. 19. Bleomycin instillation significantly increased hydroxyproline levels in the rat lungs (P<0.01, n=3, compared to normal rats; P<0.01, n=3, compared to saline instilled rats; P<0.01, n=3, compared to saline instilled with drug treated rats). PMX53 significantly reduced the bleomycin-induced hydroxyproline levels (P<0.05, n=4, compared to the rats with bleomycin instillation).

The failure of PMX53 to inhibit the toxic lung inflammation induced by bleomycin may indicate that the bleomycin-induced toxic inflammation was initiated through a different pathway or via a complicated inter-cellular reaction, rather than by a simple activation of the complement system. Type I AEC injury, type II AEC proliferation, fibroblast proliferation, and release of several cytokines, such as $PGE_2$, $TGF-\beta_1$, and GM-CSF, are considered to play major roles in PF.

After 18 days, the lungs with bleomycin instillation showed some fibrosis, as demonstrated by the significantly increased hydroxyproline levels and collagen deposition as indicated by PR staining. We found that PMX53 significantly reduced the hydroxyproline levels, although this was difficult to confirm by histology or PR staining. It is possible that 18 days is too early for the histological changes to be evident, because most studies demonstrated that the DNA and hydroxyproline changes occur between 14-21 days after bleomycin instillation, while histological evidence was present after 4 weeks.

Nevertheless, the significant reduction by PMX53 of bleomycin-induced hydroxyproline deposition indicates that the activation of the C5a cascade may be involved in the progression of fibrosis, although the role of C5a in bleomycin-induced PF is not fully understood. It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Brown L, Sernia C, Newling R, Fletcher P: Comparison of inotropic and chronotropic responses in rat isolated atria and ventricles. *Clin Exp Pharmacol Physiol* 1991a; 18:753-60.

Brown L, Cragoe E J Jn, Abel K C, Manley S W, Bourke J R: Amiloride analogues induce responses in isolated rat cardiovascular tissues by inhibition of Na+/Ca2+ exchange. *Naunyn-Schmiedeberg's Arch Pharmacol* 1991b; 344:220-4.

Christensen P J, et. al. Role of diminished epithelial GM-CSF in the pathogenesis of bleomycin-induced pulmonary fibrosis. *Am J Physiol Lung Cell Mol Physiol.* 2000; 279: L487-95.

Iyer S N, Gurujeyalakshmi G, Giri S N. Effects of pirfenidone on procollagen gene expression at the transcriptional level in bleomycin hamster model of lung fibrosis. J. Pharmacol. Exp. Ther. 1999a; 289: 211-8.

Iyer S N, Gurujeyalakshmi G, Giri S N. Effects of pirfenidone on transforming growth factor-b gene expression at the transcriptional level in bleomycin hamster model of lung fibrosis. J. Pharmacol. Exp. Ther. 1999b; 291: 367-73.

Konteatis, Z. D., Siciliano, S. J., Van Riper, G., Molineaux, C. J., Pandya, S., Fischer, P., Rosen, H., Mumford, R. A., and Springer, M. S. *J. Immunol.*, 1994 153 4200-4204.

Miric G, Dallemagne C, Endre Z, Margolin S, Taylor S M, Brown L: Reversal of cardiac and renal fibrosis by pirfenidone and spironolactone in streptozotocin-diabetic rats. *Br J Pharmacol* 2001; 133:687-694

Marchant C, Brown L, Sernia C: Renin-angiotensin system in thyroid dysfunction in rats. *J Cardiovasc Pharmacol* 1993; 22:449-55.

Mirsky I, Parmley W W, Assessment of passive elastic stiffness for isolated heart muscle and the intact heart. *Circ Res* 1973; 33:233-243.

el-Nahas A M, Muchaneta-Kubara E C, Essawy M, Soylemezoglu O. Renal fibrosis: Insights into pathogenesis and treatment. International *Journal of Biochemistry and Cellular Biology* 1997; 29:55-62.

Rosen P, Balhausen T, Bloch W, Addicks K: Endothelial relaxation is disturbed by oxidative stress in the diabetic rat heart: influence of tocopherol as antioxidant. Diabetologia 1995; 38:1157-68.

Taylor M D, Roberts J R, Hubbs A F, Reasor M J, Antonini J M. Quantitative image analysis of drug-induced lung fibrosis using laser scanning confocal microscopy. Toxicol Sci. 2002; 67:295-302.

Thrall R S, McCormick J R, Jack R M, McReynolds R A, Ward P A. Bleomycin-induced pulmonary fibrosis in the rat: inhibition by indomethacin. Am J Pathol. 1979; 95:117-30

Wang R, Ibarra-Sunga O, Verlinski L, Pick R, Uhal BD. Abrogation of bleomycin-induced epithelial apoptosis and lung fibrosis by captopril or by a caspase inhibitor. *Am J Physiol Lung Cell Mol Physiol.* 2000; 279:L143-51.

Welt K, Weiss J, Koch S, Fitzl G: Protective effects of *Ginkgo biloba* extract EGb 761 on the myocardium of experimentally diabetic rats. II. Ultrastructural and immunohistochemical investigation on microvessels and interstitium. Exp Toxicol Pathol 1999; 51:213-222.

The invention claimed is:

1. A method of treatment or alleviation of a retinal disorder, comprising the step of administering an effective amount of an antagonist of a G protein-coupled receptor to a subject in need of such treatment, wherein the retinal disorder is proliferative vitroretinopathy or macular degeneration.

2. A method according to claim 1, in which the antagonist is a C5a receptor antagonist.

3. A method according to claim 1, in which the antagonist is a peptide or a peptidomimetic compound.

4. A method according to claim 3, in which the antagonist is a cyclic peptide or a cyclic peptidomimetic compound.

5. A method according to claim 1, in which the antagonist (a) is an antagonist of a G protein-coupled receptor, (b) has substantially no agonist activity, and (c) is a cyclic peptide or peptidomimetic compound of formula I

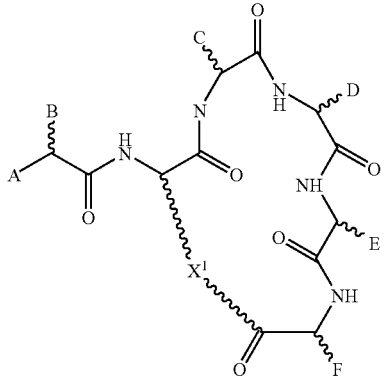

where A is H, alkyl, aryl, $NH_2$, NH-alkyl, $N(alkyl)_2$, NH-aryl, NH-acyl, NH-benzoyl, $NHSO_3H$, $NHSO_2$-alkyl, $NHSO_2$-aryl, OH, O-alkyl, or O-aryl;

B is an alkyl, aryl, phenyl, benzyl, naphthyl or indole group, or the side chain of L-phenylalanine or L-phenylglycine;

C is a substituent selected from the side chain of an amino acid selected from the group consisting of glycine, alanine, leucine, and valine, and wherein a hydrogen atom is covalently attached to the adjacent N atom, or C is bonded to the adjacent N atom to form a proline, hydroxyproline, or thioproline-cyclic side chain;

D is the side chain of a D-amino acid selected from the group consisting of D-Leucine, D-homoleucine, D-cyclohexylalanine, D-homocyclohexylalanine, D-valine, D-norleucine, D-homo-norleucine, D-phenylalanine, D-glutamine, D-glutamate, and D-tyrosine;

E is L-1-naphthyl or is the side chain of an amino acid selected from the group consisting of L-phenylalanine, L-tryptophan, L-homotryptophan, and 3-benzothienyl alanine;

F is the side chain of L-arginine, L-homoarginine, L-citrulline, or L-canavanine, or a bioisostere thereof, i.e., a side chain in which the terminal guanidine or urea group is retained, but the carbon backbone is replaced by a group which has a different structure but is such that the side chain as a whole reacts with the target protein in the same way as the parent group; and $X^1$ is —$(CH_2)_n$NH— or —$(CH_2)_n$—S—, where n is an integer of from 1 to 4; —$(CH_2)_2O$—; —$(CH_2)_3O$—; —$(CHO_3)$—; —$(CH_2)_4$—; —$CH_2COCHRNH$—; or —$CH_2$—CHCOCHRNH—, where R is the side chain of any common or uncommon amino acid.

6. A method according to claim 5, in which A is an acetamide group, or an aminomethyl group.

7. A method according to claim 1, in which the antagonist is a C5a receptor antagonist which has antagonist activity against C5aR, and has no C5a agonist activity.

8. A method according to claim 1, in which the antagonist has a receptor affinity $IC_{50} < 25$ μM, and an antagonist potency $IC_{50} < 1$ μM.

9. A method according to claim 1, in which the antagonist is selected from the group consisting of compounds 1 to 6, 10 to 15, 17, 19, 20, 22, 25, 26, 28, 30, 31, 33 to 37, 39 to 45, 56 to 58 and 60 to 64, wherein the compounds have the following chemical structures:

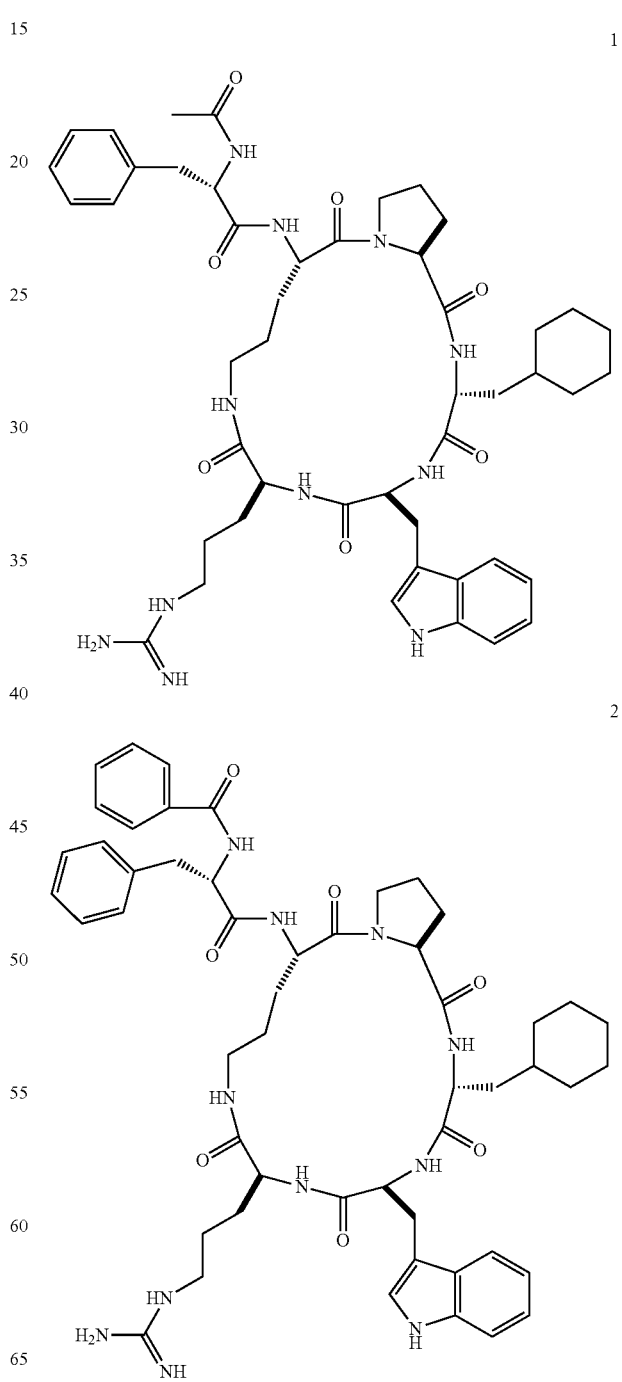

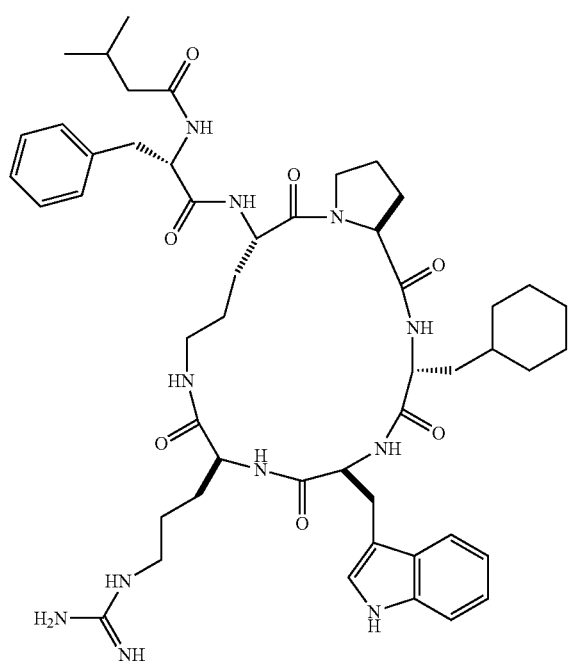
3
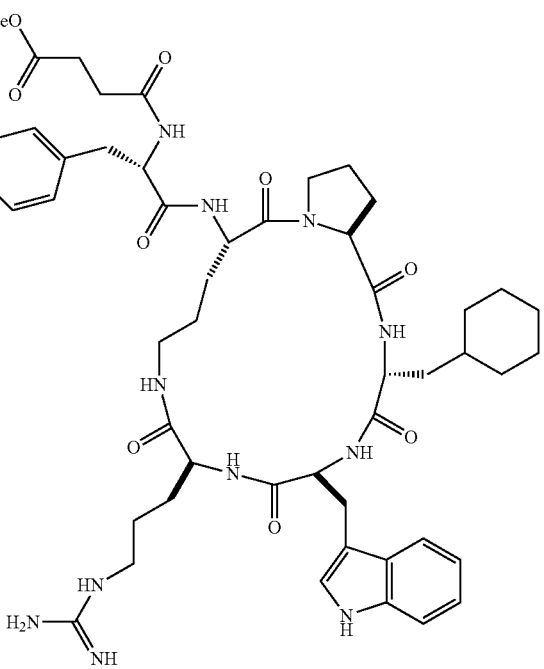
5
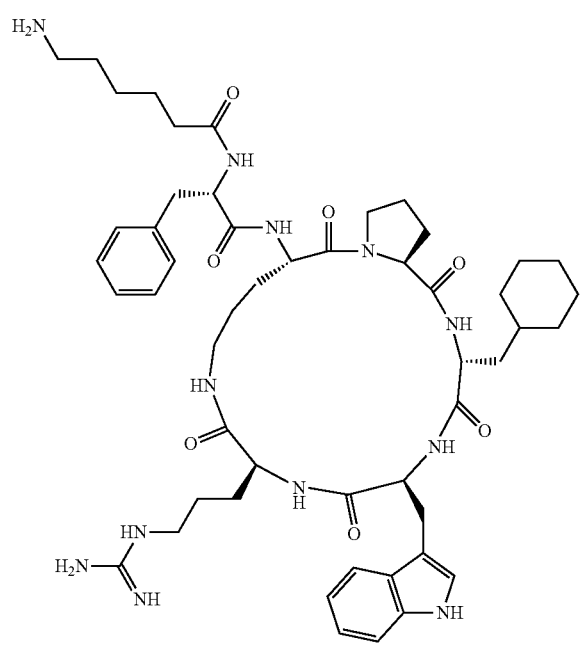
4
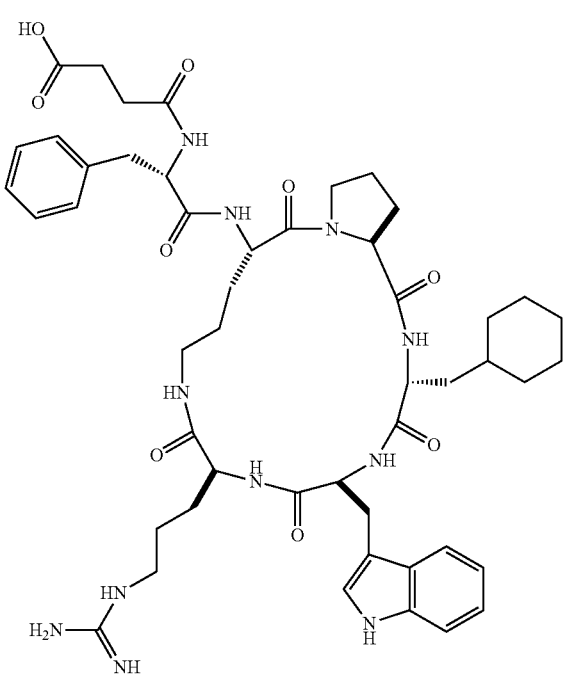
6

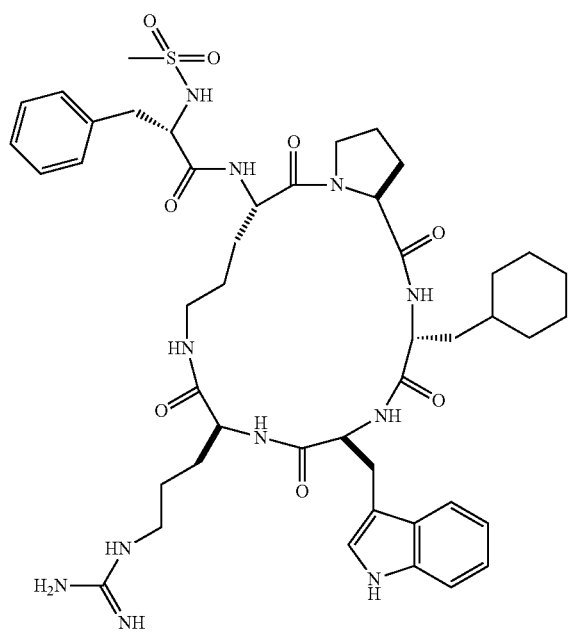
10
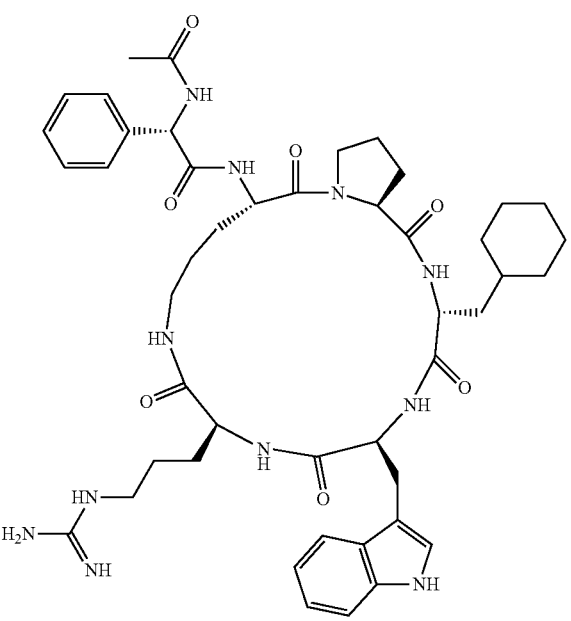
12
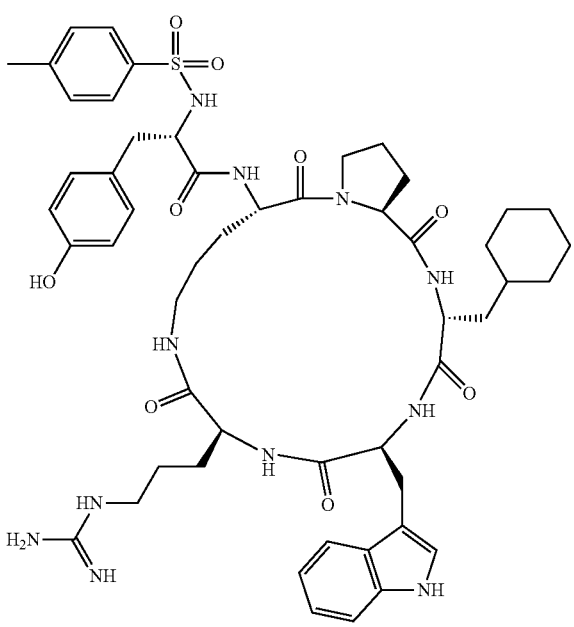
11
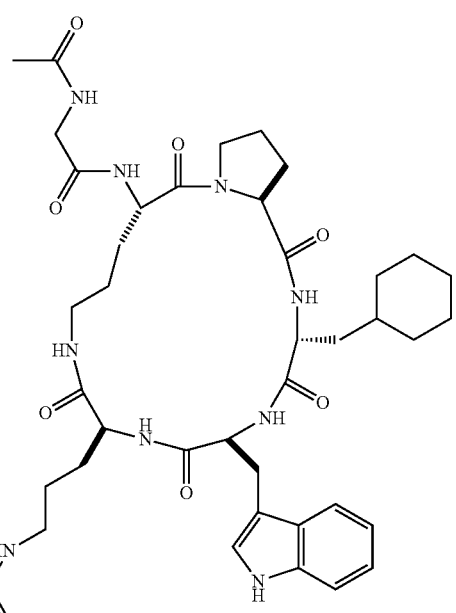
13

14
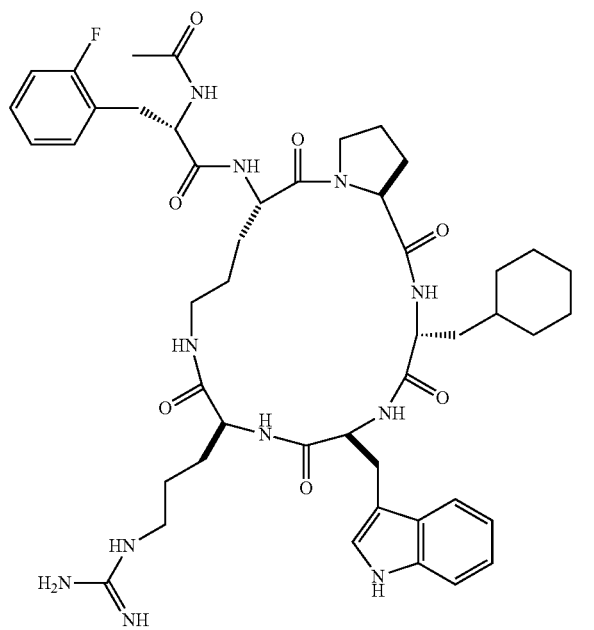
17
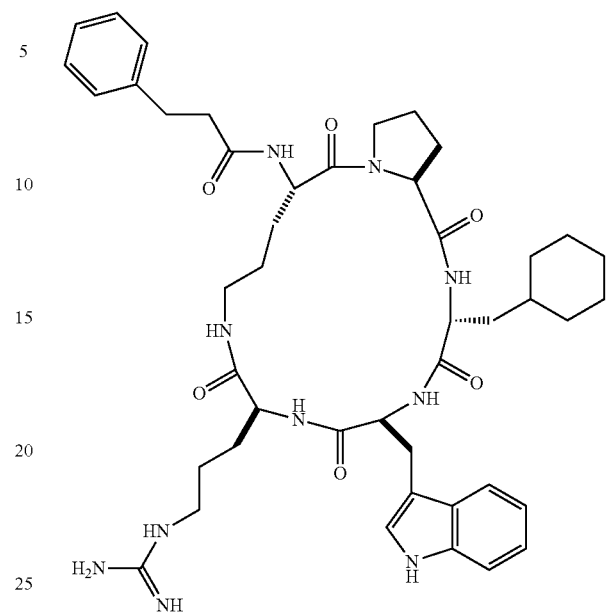
15
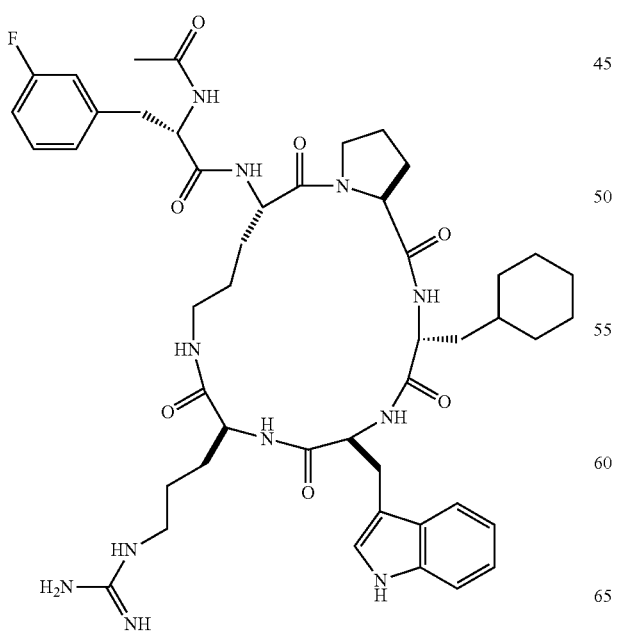
19
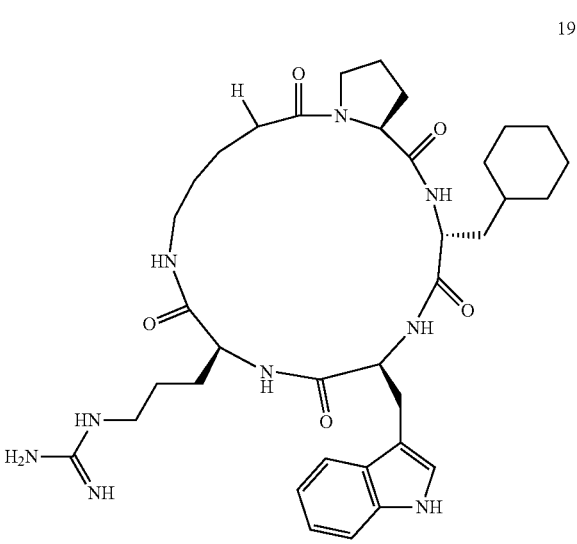

49
-continued
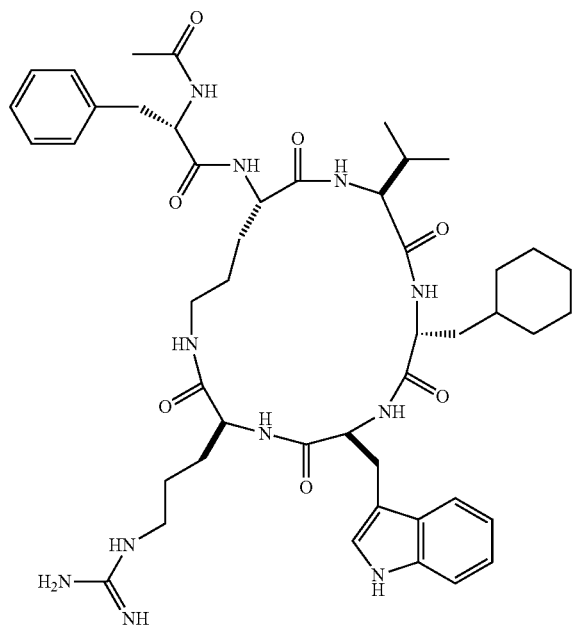
50
-continued
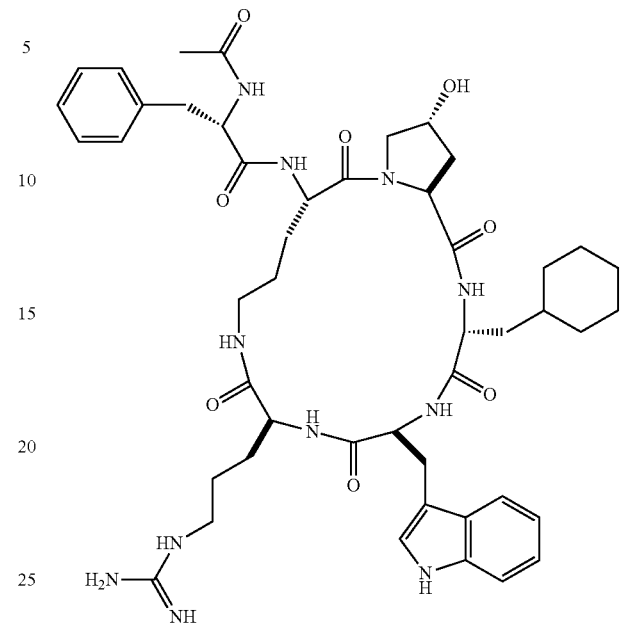
22
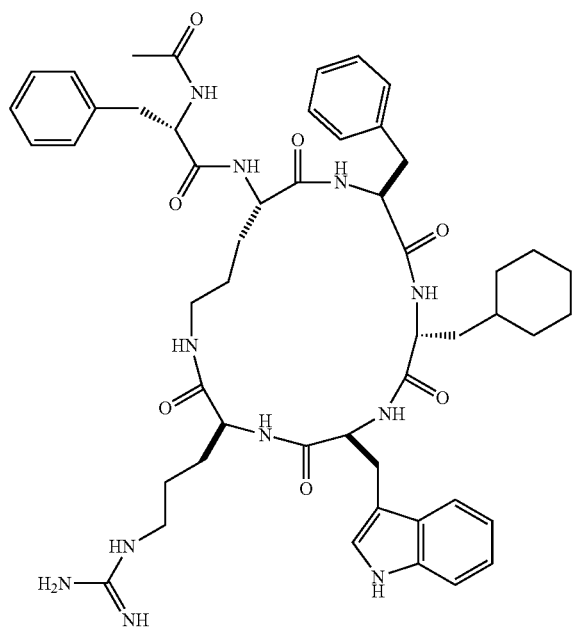
26
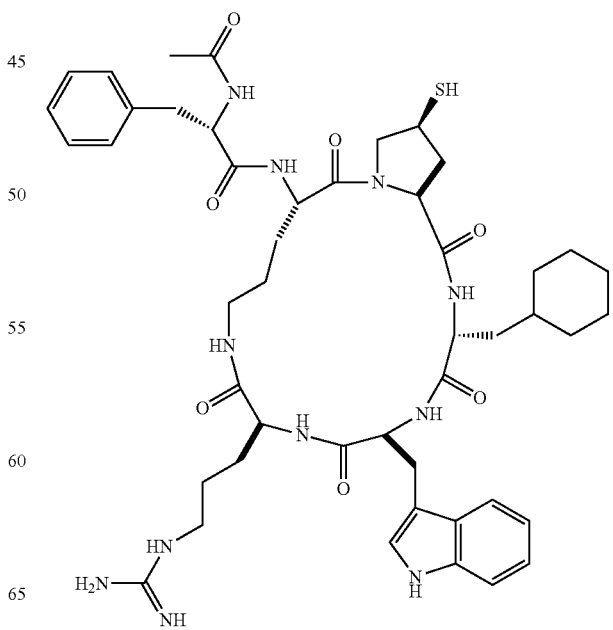

28
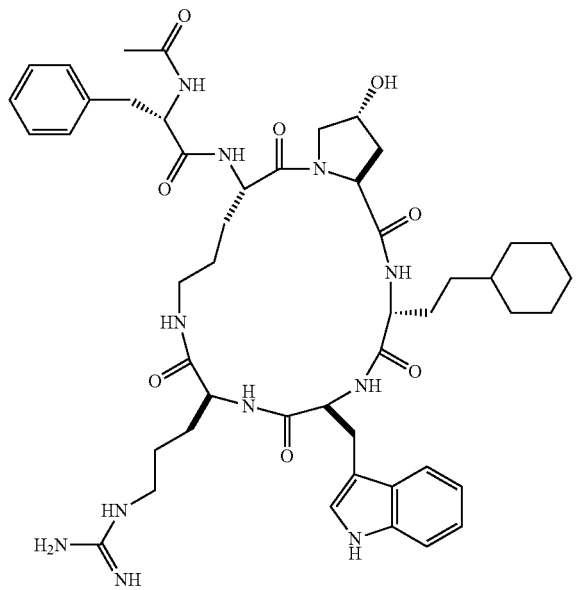
31
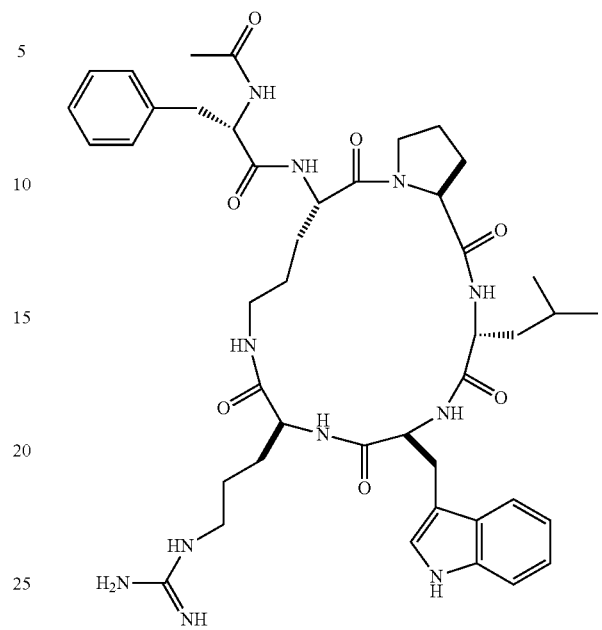
30
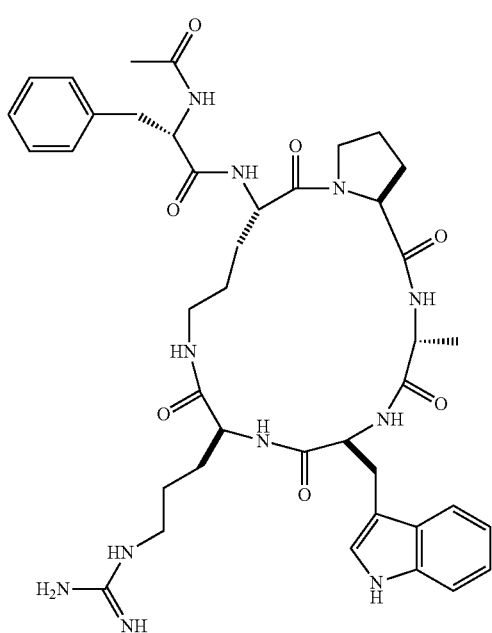
33
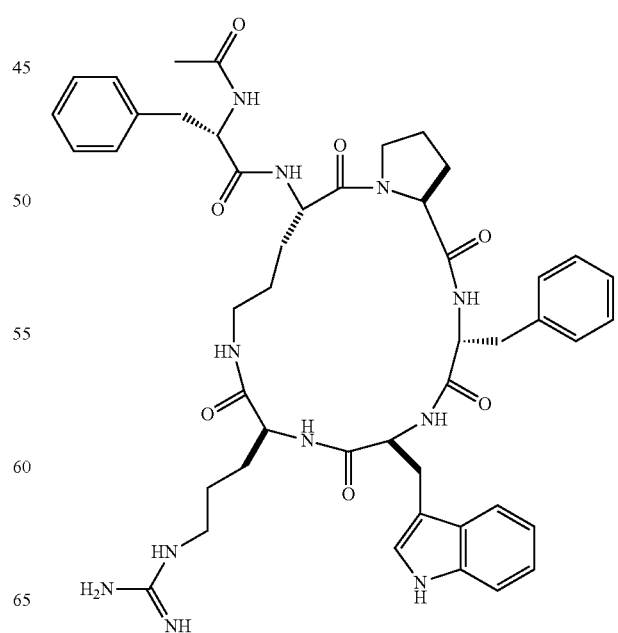

34
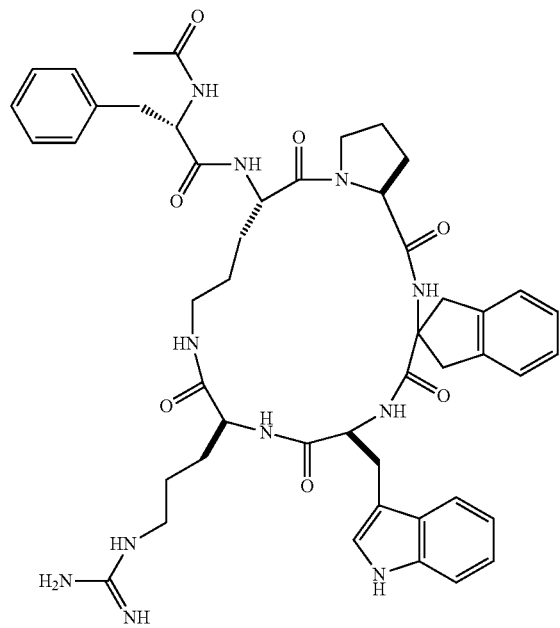
36
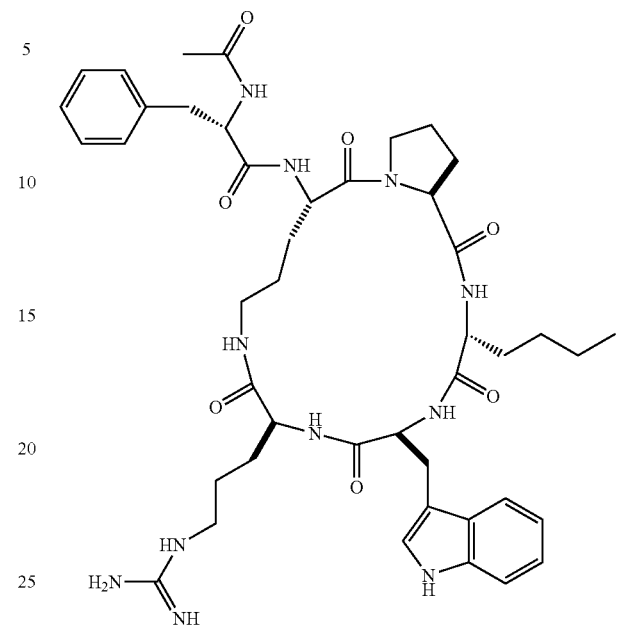
35
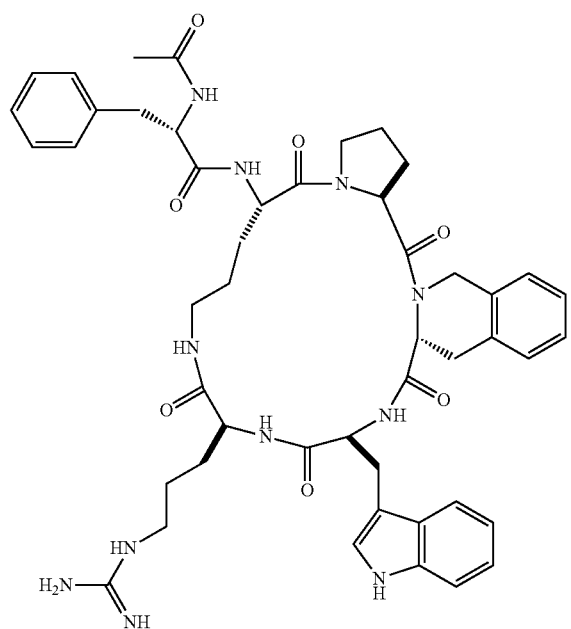
37
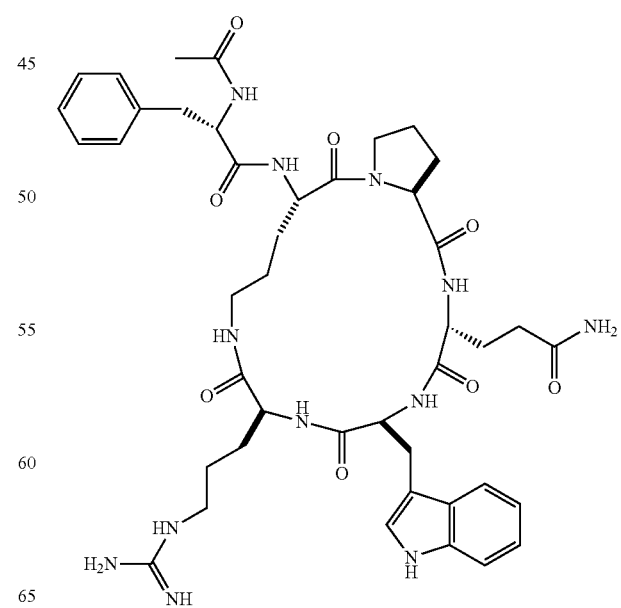

39
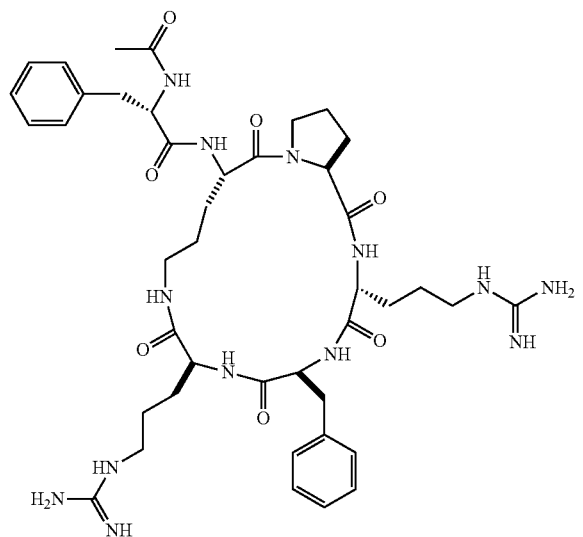
41
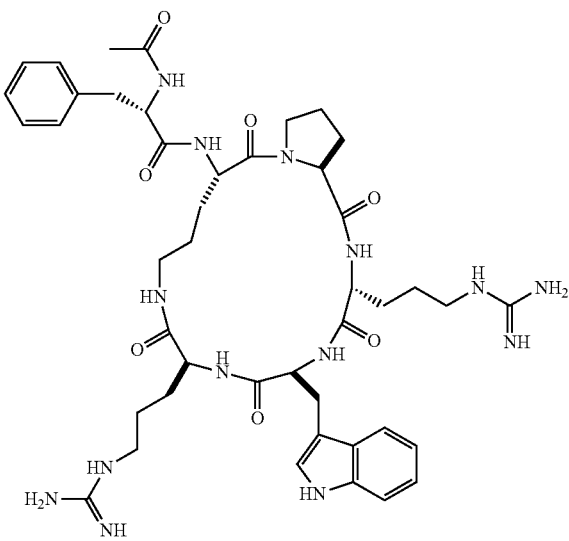
40
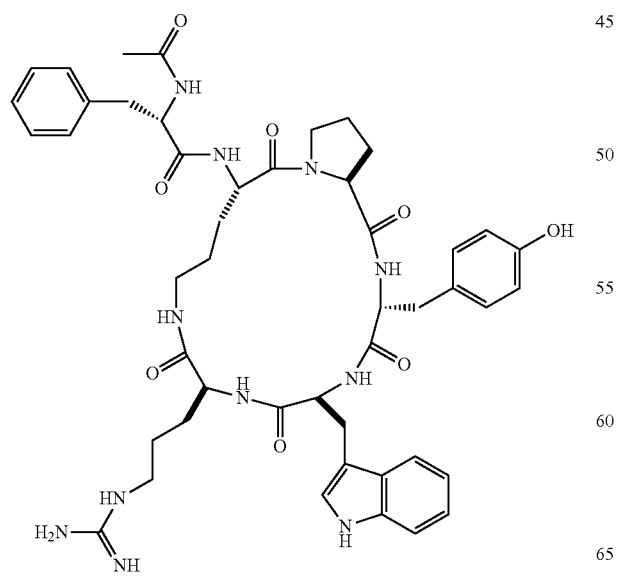
42
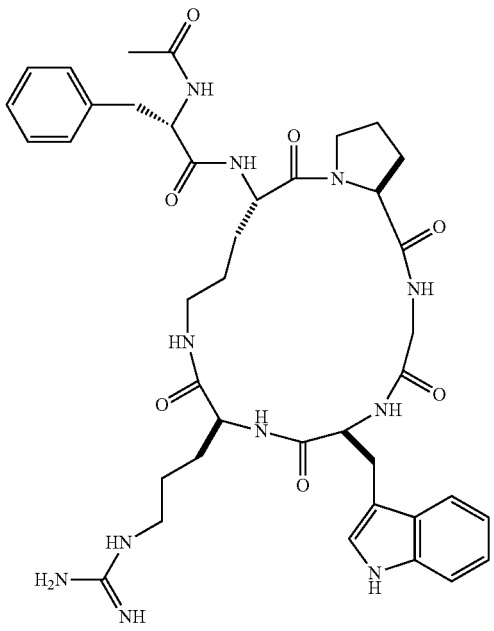

43
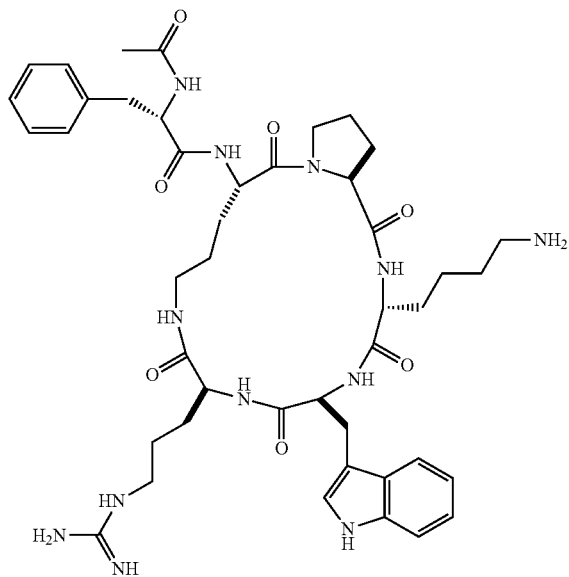
45
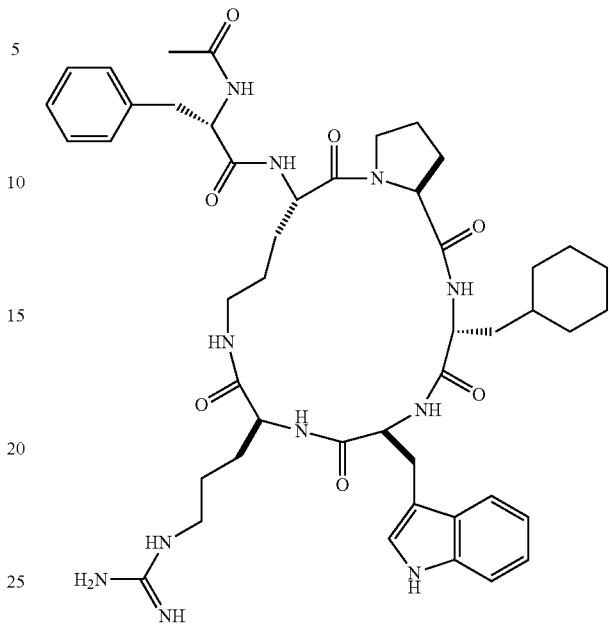
44
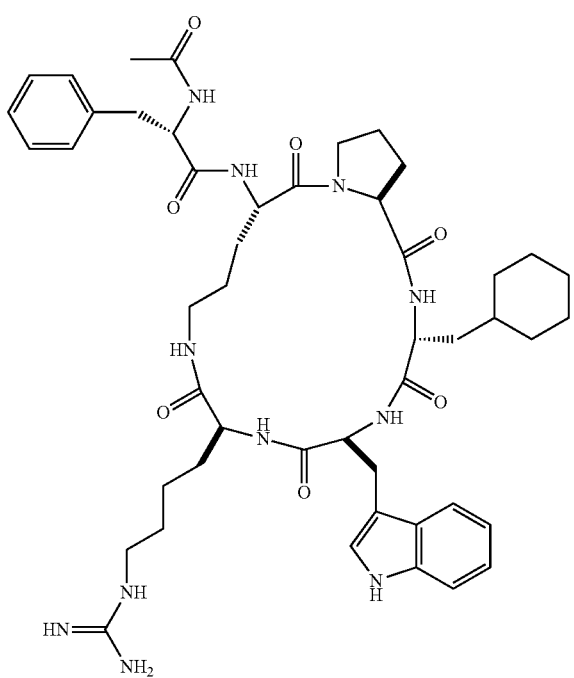
56
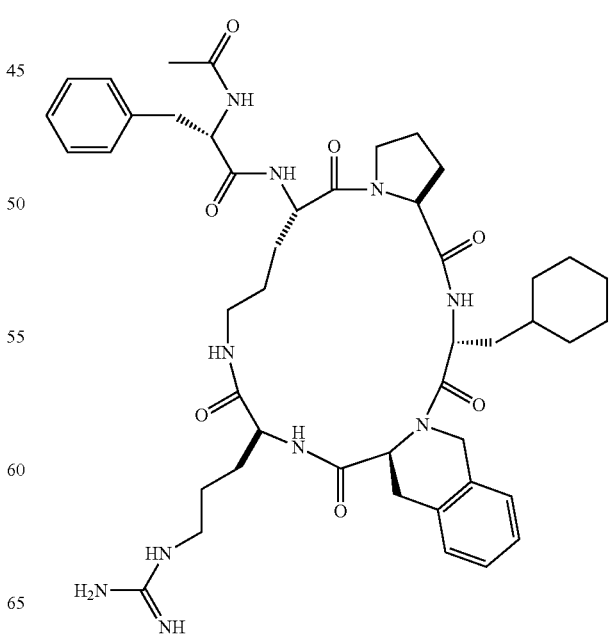

57
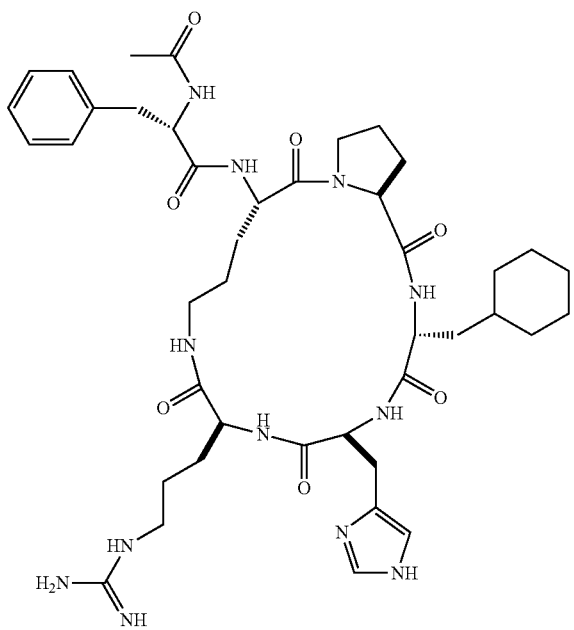
58
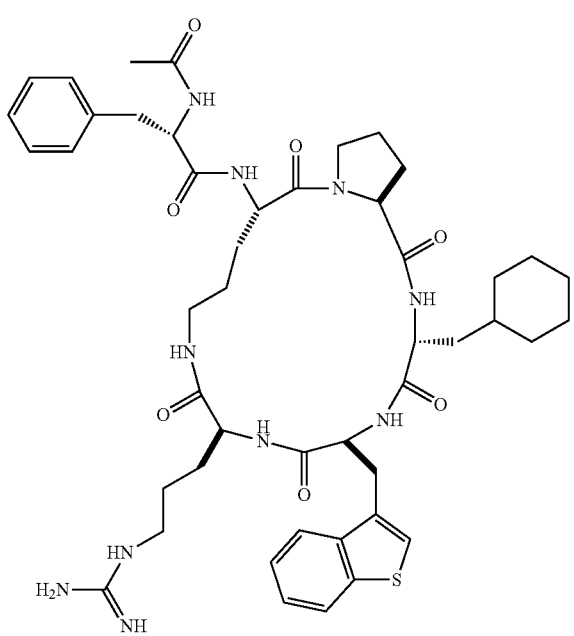
60
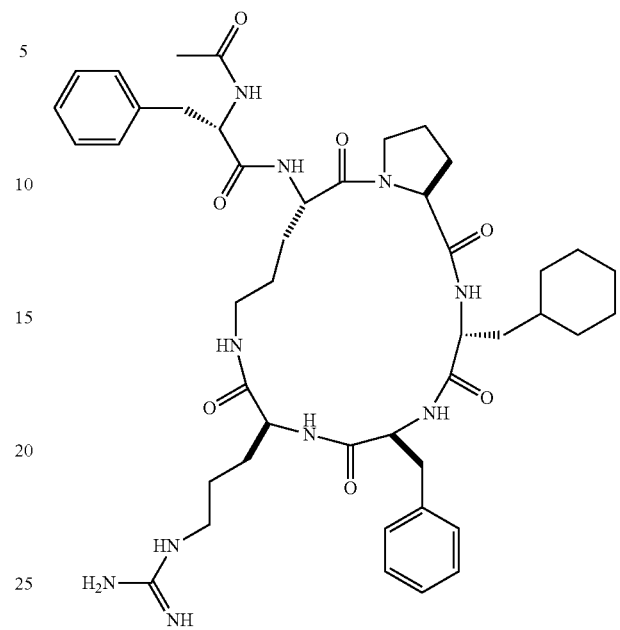
61
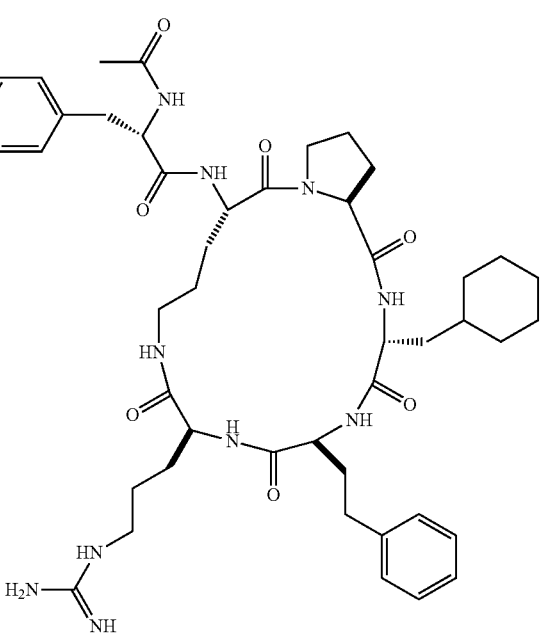

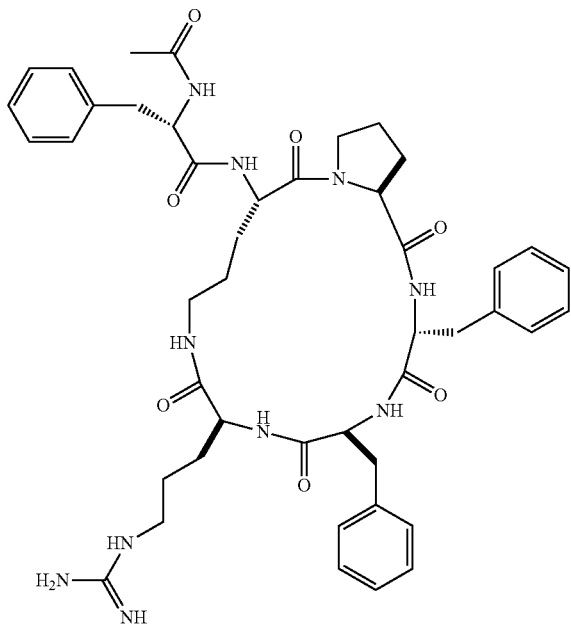
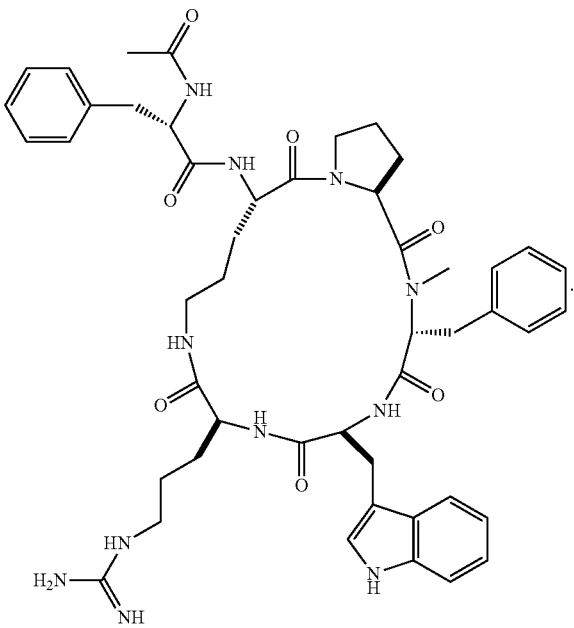
10. A method according to claim 9, in which the antagonist is PMX53 (compound I) AcF-[OP-DCha-WR]), compound 33 (AcF[OP-DPhe-WR]), compound 60 (AcF-[OP-DCha-FR]) or compound 45 (AcF-[OP-DCha-WCit]), wherein the compounds have chemical structures as follows:
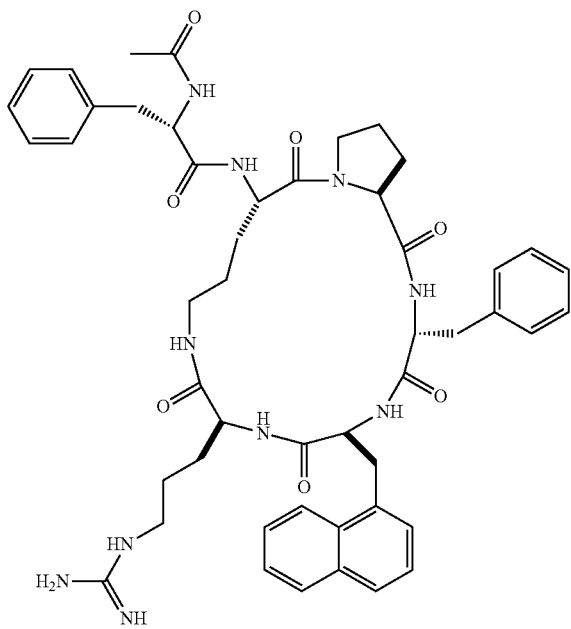
and
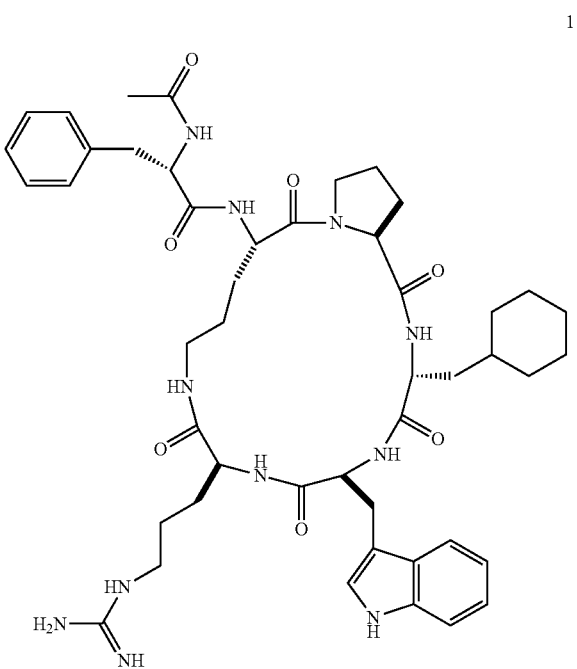

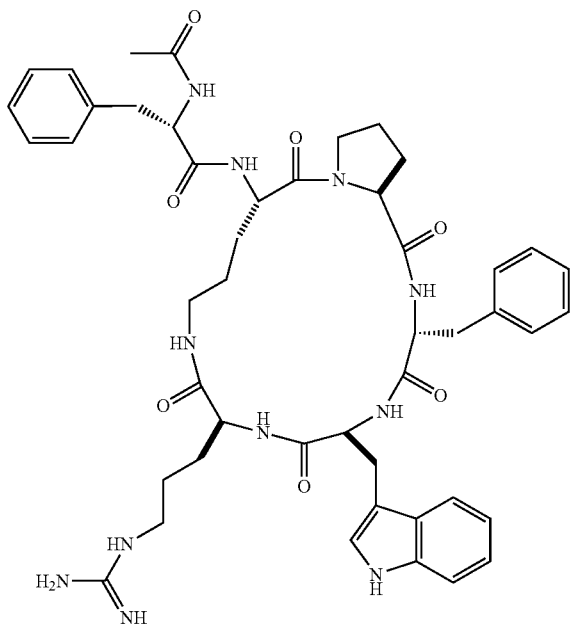
and
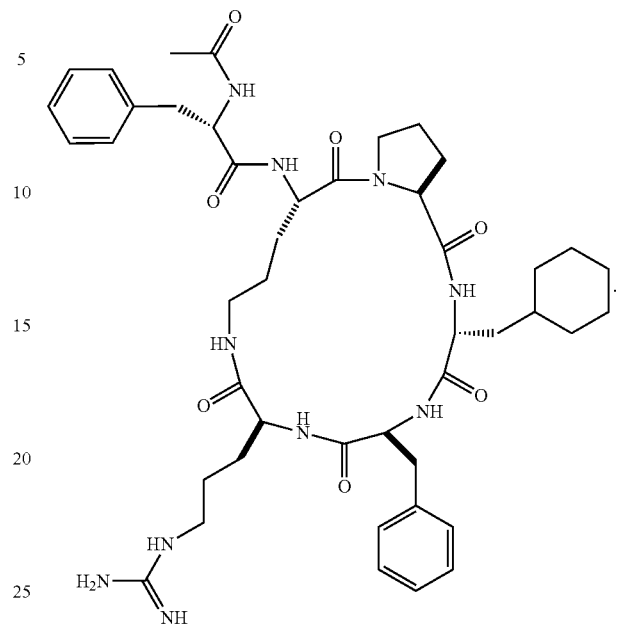
11. A method according to claim 9, in which the antagonist is PMX53, having the formula:
12. A method according to claim 1, in which the retinal disorder is proliferative vitroretinopathy.
13. A method according to claim 1, in which the retinal disorder is macular degeneration.
* * * * *